United States Patent
Kilgore et al.

(10) Patent No.: US 9,707,549 B1
(45) Date of Patent: Jul. 18, 2017

(54) ETHYLENE OLIGOMERIZATION CATALYST SYSTEMS USING CHEMICALLY-TREATED SOLID OXIDES

(71) Applicant: Chevron Phillips Chemical Company LP, The Woodlands, TX (US)

(72) Inventors: Uriah J. Kilgore, Kingwood, TX (US); Steven R. Hutchison, Spring, TX (US); Orson L. Sydora, Houston, TX (US); Steven M. Bischof, Humble, TX (US); Jared T. Fern, Kingwood, TX (US); Max P. McDaniel, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/165,267

(22) Filed: May 26, 2016

(51) Int. Cl.
   - *C08F 10/02* (2006.01)
   - *C07C 2/32* (2006.01)
   - *B01J 31/14* (2006.01)
   - *B01J 31/18* (2006.01)

(52) U.S. Cl.
   CPC .......... *B01J 31/189* (2013.01); *B01J 31/143* (2013.01); *C07C 2/32* (2013.01); *C08F 10/02* (2013.01); *B01J 2231/20* (2013.01); *B01J 2531/62* (2013.01); *C07C 2531/14* (2013.01); *C07C 2531/22* (2013.01); *C08F 2410/01* (2013.01)

(58) Field of Classification Search
   CPC . C08F 10/02; C07C 2/32; B01J 31/143; B01J 31/189
   See application file for complete search history.

(56) References Cited

U.S. PATENT DOCUMENTS

| | | | |
|---|---|---|---|
| 5,340,785 A * | 8/1994 | Reagen | ................... C08F 10/00 502/108 |
| 6,031,145 A | 2/2000 | Commereuc et al. | |
| 6,103,654 A | 8/2000 | Commereuc et al. | |
| 6,107,230 A | 8/2000 | McDaniel et al. | |
| 6,165,929 A | 12/2000 | McDaniel et al. | |
| 6,221,986 B1 | 4/2001 | Commereuc et al. | |
| 6,294,494 B1 | 9/2001 | McDaniel et al. | |

(Continued)

FOREIGN PATENT DOCUMENTS

| | | | |
|---|---|---|---|
| CA | 2837590 A1 * | 6/2015 | ............ B01J 31/143 |
| WO | WO 2008/077908 | 7/2008 | |

(Continued)

OTHER PUBLICATIONS

Modern Plastics Encyclopedia, Mid-Nov. 1995 Issue, vol. 72, No. 12, 3 pages.

(Continued)

*Primary Examiner* — Catherine S Branch
(74) *Attorney, Agent, or Firm* — Merchant & Gould P.C.

(57) ABSTRACT

Disclosed herein are catalyst compositions containing a heteroatomic ligand transition metal compound complex, a chemically-treated solid oxide, and an organoaluminum compound. These catalyst compositions can be used in an ethylene oligomerization process to produce a liquid oligomer product containing hexene and octene, as well as a solid polymer product with a molecular weight sufficiently high to permit easy separation of the liquid oligomer product from the solid polymer product.

20 Claims, 3 Drawing Sheets

(56) References Cited

U.S. PATENT DOCUMENTS

| | | |
|---|---|---|
| 6,300,271 B1 | 10/2001 | McDaniel et al. |
| 6,316,553 B1 | 11/2001 | McDaniel et al. |
| 6,355,594 B1 | 3/2002 | McDaniel et al. |
| 6,376,415 B1 | 4/2002 | McDaniel et al. |
| 6,388,017 B1 | 5/2002 | McDaniel et al. |
| 6,391,816 B1 | 5/2002 | McDaniel et al. |
| 6,395,666 B1 | 5/2002 | McDaniel et al. |
| 6,524,987 B1 | 2/2003 | Collins et al. |
| 6,548,441 B1 | 4/2003 | McDaniel et al. |
| 6,548,442 B1 | 4/2003 | McDaniel et al. |
| 6,576,583 B1 | 6/2003 | McDaniel et al. |
| 6,613,712 B1 | 9/2003 | McDaniel et al. |
| 6,632,894 B1 | 10/2003 | McDaniel et al. |
| 6,667,274 B1 | 12/2003 | Hawley et al. |
| 6,750,302 B1 | 6/2004 | McDaniel et al. |
| 6,828,269 B2 | 12/2004 | Commereuc et al. |
| 6,903,042 B2 | 6/2005 | Drochon et al. |
| 6,911,410 B2 | 6/2005 | Lecocq et al. |
| 6,951,831 B2 | 10/2005 | Lecocq et al. |
| 7,256,152 B2 | 8/2007 | Olivier-Bourbigou et al. |
| 7,294,599 B2 | 11/2007 | Jensen et al. |
| 7,411,105 B2 | 8/2008 | Forestiere et al. |
| 7,601,665 B2 | 10/2009 | McDaniel et al. |
| 7,884,163 B2 | 2/2011 | McDaniel et al. |
| 8,309,485 B2 | 11/2012 | Yang et al. |
| 8,623,973 B1 | 1/2014 | McDaniel et al. |
| 8,680,003 B2 | 3/2014 | Sydora et al. |
| 8,703,886 B1 | 4/2014 | Yang et al. |
| 8,816,147 B2 | 8/2014 | Vinel et al. |
| 9,023,959 B2 | 5/2015 | McDaniel et al. |
| 9,101,919 B2 | 8/2015 | Toulhoat et al. |
| 9,175,109 B1 | 11/2015 | Kreischer et al. |
| 9,260,358 B2 | 2/2016 | Cazaux et al. |
| 9,308,528 B2 | 4/2016 | Boulens et al. |
| 9,309,167 B2 | 4/2016 | Grasset et al. |
| 9,428,531 B2 | 8/2016 | Boulens et al. |
| 2010/0076167 A1 | 3/2010 | McDaniel et al. |
| 2011/0082323 A1* | 4/2011 | Small .................. B01J 21/12 585/18 |
| 2012/0232235 A1 | 9/2012 | Hlavinka |
| 2012/0271018 A1 | 10/2012 | Murray et al. |
| 2012/0309965 A1 | 12/2012 | Sydora et al. |
| 2013/0172497 A1 | 7/2013 | Hlavinka et al. |
| 2013/0331629 A1 | 12/2013 | Sydora et al. |
| 2015/0031914 A1* | 1/2015 | Gao .................... C07C 2/36 564/12 |
| 2015/0087873 A1 | 3/2015 | Overett et al. |

FOREIGN PATENT DOCUMENTS

| | | |
|---|---|---|
| WO | WO 2013/137676 | 9/2013 |
| WO | WO 2014/008964 | 1/2014 |
| WO | WO 2015/094207 | 6/2015 |
| WO | WO 2015/105738 | 7/2015 |

OTHER PUBLICATIONS

Film Extrusion Manual—Process, Materials, Properties, TAPPI Press, 1992, 16 pages.

* cited by examiner

ETHYLENE OLIGOMERIZATION CATALYST SYSTEMS USING CHEMICALLY-TREATED SOLID OXIDES

BACKGROUND OF THE INVENTION

The oligomerization of ethylene to produce hexenes and/or octenes in a homogeneous process often can produce a by-product stream containing an ethylene-based polymer. In some circumstances, the polymer produced can cause reactor fouling, and associated costs, clean-up, and downtime. It would be beneficial to produce hexenes and/or octenes from ethylene using a process that is less susceptible to reactor fouling and its related drawbacks. Accordingly, it is to these ends that the present invention is directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Catalyst systems containing a chemically-treated solid oxide are disclosed and described herein. Such catalyst systems can comprise a heteroatomic ligand transition metal compound complex, a chemically-treated solid oxide, and an organoaluminum compound. Illustrative and non-limiting examples of heteroatomic ligand transition metal compound complexes can include diphosphino amine transition metal compound complexes, $N^2$-phosphinyl amidine transition metal compound complexes, $N^2$-phosphinyl formamidine transition metal compound complexes, and $N^2$-phosphinyl guanidine transition metal compound complexes. Methods for preparing these catalyst systems also are provided herein, and some of these methods can result in unexpected increases in catalyst system activity and productivity.

Embodiments of this invention also are directed to oligomerization processes, and these processes can comprise contacting ethylene, any of the catalyst systems disclosed herein, and an optional organic reaction medium, and forming an oligomer product. The oligomer product can contain a liquid oligomer product and a solid polymer product, and beneficially, the oligomerization processes can be performed without reactor fouling and its related drawbacks.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects and embodiments may be directed to various feature combinations and sub-combinations described in the detailed description.

BRIEF DESCRIPTION OF THE FIGURES

The accompanying drawings, which are incorporated in and constitute a part of this disclosure, illustrate various embodiments of the present invention. In the drawings.

DEFINITIONS

Figure 1:
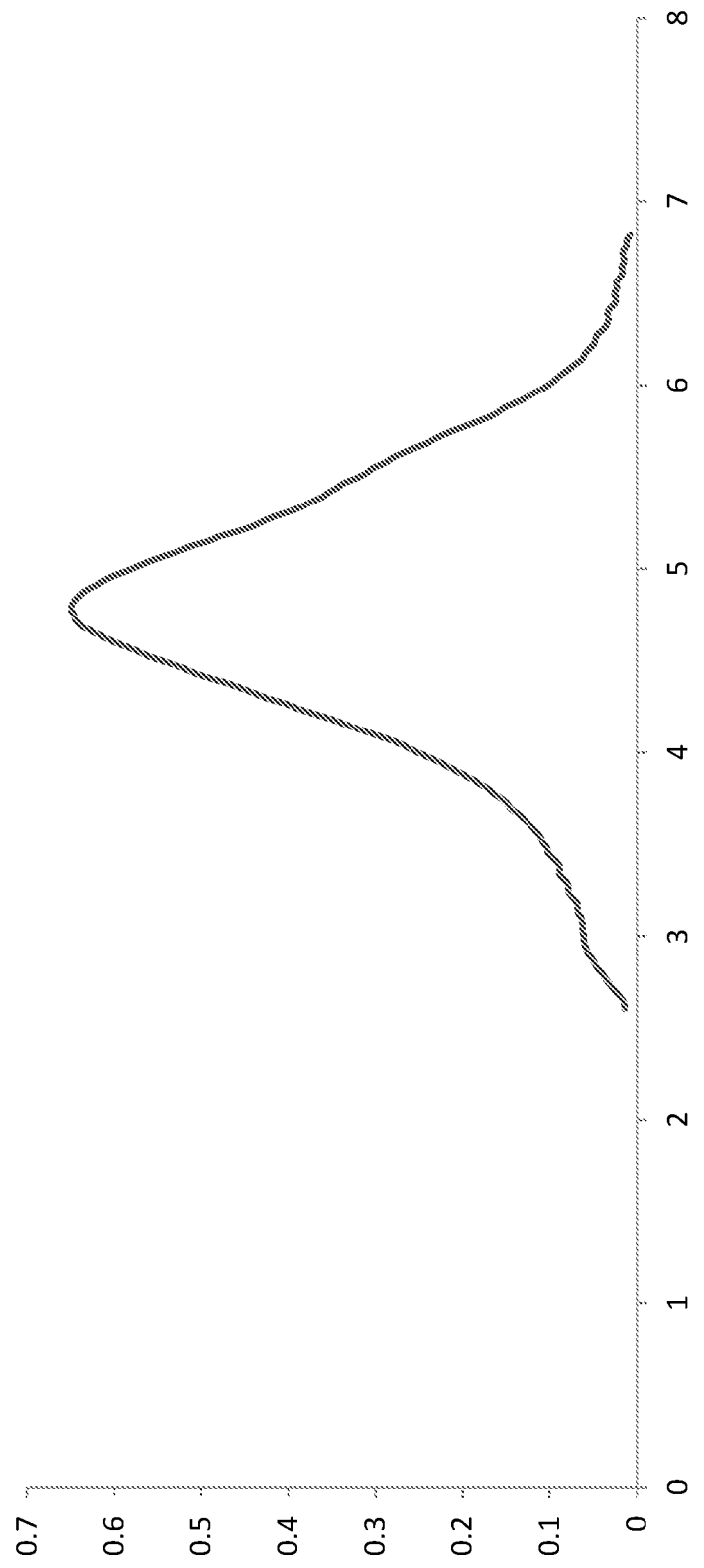
FIG. 1 presents a plot of the molecular weight distribution of the polymer product of Example 10, representative of polymer products produced using a catalyst system containing heteroatomic ligand transition metal compound complex A, a chemically-treated solid oxide, and an organoaluminum compound.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects and/or embodiments, a combination of different features can be envisioned. For each and every aspect, and/or embodiment, and/or feature disclosed herein, all combinations that do not detrimentally affect the designs, compositions, processes, and/or methods described herein are contemplated with or without explicit description of the particular combination. Additionally, unless explicitly recited otherwise, any aspect, and/or embodiment, and/or feature disclosed herein can be combined to describe inventive processes and compositions consistent with the present disclosure.

Regarding claim transitional terms or phrases, the transitional term "comprising," which is synonymous with "including," "containing," "having," or "characterized by," is open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristics of the claimed invention. A "consisting essentially of" claim occupies a middle ground between closed claims that are written in a "consisting of" format and fully open claims that are drafted in a "comprising" format. Absent an indication to the contrary, describing a composition or method as "consisting essentially of" is not to be construed as "comprising," but is intended to describe the recited element that includes materials or steps which do not significantly alter the composition or method to which the term is applied. For example, an olefin feedstock consisting essentially of a material A can include impurities typically present in a commercially produced or commercially available sample of the recited compound or composition. When a claim includes different features and/or feature classes (for example, a method step, olefin feedstock features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize an olefin feedstock consisting of specific components; alternatively, consisting essentially of specific components; or alternatively, comprising the specific components and other non-recited components. While compositions and methods are described in terms of "comprising" various components or steps, the compositions and methods can also "consist essentially of" or "consist of" the various components or steps, unless specifically stated otherwise. For example, a catalyst system consistent with certain embodiments of the present invention can comprise; alternatively, consist essentially of; or alternatively, consist of; a heteroatomic ligand transition metal compound complex, a chemically-treated solid oxide, and an organoaluminum compound.

The terms "a," "an," and "the" are intended to include plural alternatives, e.g., at least one, unless otherwise specified. For instance, the disclosure of "an electron-withdrawing anion" is meant to encompass one, or combinations of more than one, electron-withdrawing anion (e.g., sulfate, chloride, fluoride, etc.), unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; and a general reference to a butyl group includes an n-butyl group, a sec-butyl group, an iso-butyl group, and a t-butyl group.

Within this disclosure, the normal rules of organic nomenclature prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4-position and hydrogens located at the 2, 3, 5, and 6 positions. References to compounds or groups having substitutions at positions in addition to the indicated position can be referenced using comprising or some other alternative language. For example, a reference to a phenyl group comprising a substituent at the 4-position refers to a group having a non-hydrogen substituent at the 4-position and hydrogen or any non-hydrogen substituent at the 2, 3, 5, and 6 positions.

The terms "contact product," "contacting," and the like, are used herein to describe compositions and methods wherein the components are contacted together in any order, in any manner, and for any length of time, unless otherwise specified. For example, the components can be contacted by blending or mixing. Further, unless otherwise specified, the contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Similarly, the term "contacting" is used herein to refer to materials which can be blended, mixed, slurried, dissolved, reacted, treated, or otherwise contacted in some other manner. Hence, "contacting" two or more components can result in a mixture, a reaction product, a reaction mixture, etc.

The terms "catalyst composition," "catalyst mixture," "catalyst system," and the like, do not depend upon the actual product or composition resulting from the contact or reaction of the initial components of the disclosed or claimed catalyst composition/mixture/system, the nature of the active catalytic site, or the fate of the organoaluminum compound, the heteroatomic ligand transition metal compound complex, or the chemically-treated solid oxide, after combining these components. Therefore, the terms "catalyst composition," "catalyst mixture," "catalyst system," and the like, encompass the initial starting components of the composition, as well as whatever product(s) may result from contacting these initial starting components. The terms "catalyst composition," "catalyst mixture," "catalyst system," and the like, may be used interchangeably throughout this disclosure.

The term "hydrocarbon" whenever used in this specification and claims refers to a compound containing only carbon and hydrogen. The term "olefin" as used herein refers to a hydrocarbon that has at least one carbon-carbon double bond that is not part of an aromatic ring or ring system. The term "olefin" includes aliphatic and aromatic, cyclic and acyclic, and/or linear and branched compounds having at least one carbon-carbon double bond that is not part of an aromatic ring or ring system, unless specifically stated otherwise. Olefins having only one, only two, only three, etc., carbon-carbon double bonds can be identified by use of the tem "mono," "di," "tri," etc., within the name of the olefin. The olefins can be further identified by the position of the carbon-carbon double bond(s). The term "alpha olefin" as used herein refers to any olefin that has a double bond between the first and second carbon atom of a contiguous chain of carbon atoms. The term "alpha olefin" includes linear and branched alpha olefins and alpha olefins which have more than one non-aromatic carbon-carbon double bond, unless expressly stated otherwise. The term "normal alpha olefin" as used herein refers to a linear aliphatic hydrocarbon mono-olefin having a double bond between the first and second carbon atom.

An "aromatic compound" refers to a compound containing a cyclically conjugated moiety that follows the Hückel (4n+2) rule and containing (4n+2) pi-electrons, where n is an integer from 1 to about 5. Aromatic compounds can be monocyclic or polycyclic, unless otherwise specified. Non-limiting examples of aromatic compounds include benzene, naphthalene, and toluene, among others.

The term oligomer refers to a product that contains from 2 to 20 monomer units. The terms "oligomerization product" and "oligomer product" include all products made by the "oligomerization" process, including the "oligomers" and products which are not "oligomers" (e.g., products which contain more than 20 monomer units, or solid polymer).

The term "oligomerization," and its derivatives, refers to processes which produce an oligomer product comprising at least 20 wt. %, 35 wt. %, 50 wt. %, or 60 wt. % products comprising from 2 to 20 monomer units. In an example, an "oligomerization" process using ethylene as the monomer produces a mixture of products comprising at least 20 wt. %, 35 wt. %, 50 wt. %, or 60 wt. % oligomers having from 4 to 40 carbon atoms.

The term "trimerization," and it derivatives, refers to a process which produces a mixture of products comprising at least 20 wt. %, 35 wt. %, 50 wt. %, or 60 wt. % products comprising three and only three monomer units. A "trimer" is a product which comprises three and only three monomer units. A "trimerization product" includes all products made by the trimerization process including trimer and product(s) which are not trimer (e.g., dimers or tetramers, solid polymer). In an example, a "trimerization" process using ethylene as the monomer produces a mixture of products comprising at least 20 wt. %, 35 wt. %, 50 wt. %, or 60 wt. % hexenes.

The term "tetramerization," and it derivatives, refers to a process which produces a mixture of products comprising at least 20 wt. %, 35 wt. %, 50 wt. %, or 60 wt. % products comprising four and only four monomer units. A "tetramer" is a product which comprises four and only four monomer units. A "tetramerization product" includes all products made by the tetramerization process including tetramer and product(s) which are not tetramer (e.g., dimers or trimers, solid polymer). In an example, a "tetramerization" process using ethylene as the monomer produces a mixture of products comprising at least 20 wt. %, 35 wt. %, 50 wt. %, or 60 wt. % octenes.

The term "trimerization and tetramerization," and it derivatives, refers to a process which produces a mixture of products comprising at least 20 wt. %, 35 wt. %, 50 wt. %, or 60 wt. % products comprising three and/or four and only three and/or four monomer units. A "trimerization and tetramerization product" includes all products made by the "trimerization and tetramerization" process including trimer, tetramer, and product(s) which are not trimer and tetramer (e.g., dimers, solid polymer). In an example, a "trimerization and tetramerization" process using ethylene as the monomer produces a mixture of products comprising at least 20 wt. %, 35 wt. %, 50 wt. %, or 60 wt. % hexenes and octenes.

Catalyst system productivity is defined as kilograms of a product per gram of transition metal of the heteroatomic ligand transition metal compound complex utilized in the catalyst system. Catalyst system productivity can be stated in terms of various products. For example, in an ethylene oligomerization process utilizing a catalyst system comprising a heteroatomic ligand chromium compound complex, the catalyst system productivities that can be utilized can include (kg oligomer product)/(g Cr), (kg $C_6$ product)/(g Cr), (kg ($C_6+C_8$) product)/(g Cr), and (kg polymer)/(g Cr), among other productivities.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

The present invention is directed generally to new catalyst systems, methods for preparing the catalyst systems, methods for using the catalyst systems to oligomerize olefins, and the liquid oligomer and solid polymer products produced using such catalyst systems. In particular, the present invention relates to catalyst systems containing a heteroatomic ligand transition metal compound complex, a chemically-treated solid oxide, and an organoaluminum compound, and to oligomerization process utilizing these catalyst systems.

As disclosed herein, the heterogeneous catalyst systems and processes of this invention can provide distinct advantages over homogeneous catalyst systems and processes in the ease of separation (e.g., solid-liquid separation techniques) of the liquid oligomer product from solid polymer product and/or from the (solid) components of the catalyst system. Moreover, and while not wishing to be bound by the following theory, it is believed that the processes of this invention can reduce or possibly eliminate reactor fouling. It is further believed, while not wishing to be bound by the following theory, that the processes of this invention produce a solid polymer having sufficiently high molecular weight to reduce its adherence to reactor walls and other surfaces. It is also believed, while not wishing to be bound by the following theory, that the production of a solid polymer having a higher molecular weight, and the reduction of the polymer's adherence to reactor walls and other surfaces, can reduce or possibly eliminate reactor fouling. Further, and while not wishing to be bound by the following theory, it is believed that another beneficial aspect of this invention is that the solid polymer product can be insoluble in the organic reaction medium used in the oligomerization process. Additionally, and while not wishing to be bound by the following theory, it is believed that another beneficial aspect of this invention is that at least a portion of the solid polymer product can comprise solid particles of the chemically-treated solid oxide component of the catalyst system. Each of factors, either individually or in any combination, can lead to the reduction or possible elimination of reactor fouling and/or the ease of separation and recovery of the liquid oligomer product.

Catalyst Systems

Embodiments of this invention are directed to a catalyst system comprising a) a heteroatomic ligand transition metal compound complex, b) a chemically-treated solid oxide, and c) an organoaluminum compound. Generally, the heteroatomic ligand transition metal compound complex, the chemically-treated solid oxide, and the organoaluminum compound are independent elements of the catalyst system and are described independently herein. The independent descriptions of the heteroatomic ligand transition metal compound complex, the chemically-treated solid oxide, and the organoaluminum compound can be utilized without limitation, and in any combination, to further describe any catalyst system comprising a) a heteroatomic ligand transition metal compound complex, b) a chemically-treated solid oxide, and c) an organoaluminum compound.

Heteroatomic Ligand Transition Metal Compound Complexes

Generally, the heteroatomic ligand transition metal compound complex of the catalyst systems described herein is composed of a heteroatomic ligand and a transition metal compound. The heteroatomic ligand and the transition metal compound are independent elements of the heteroatomic ligand transition metal compound complex and are independently described herein. The independent descriptions of the heteroatomic ligand and the transition metal compound can be utilized without limitation, and in any combination, to further describe the heteroatomic ligand transition metal compound complex of the catalyst systems described herein.

In an embodiment, the heteroatomic ligand can comprise, can consist essentially of, or can be, a diphosphino amine, an $N^2$-phosphinyl amidine, an $N^2$-phosphinyl formamidine, an $N^2$-phosphinyl guanidine, or any combination thereof. In some embodiments, the heteroatomic ligand can comprise, can consist essentially of, or can be, a diphosphino amine; alternatively, an $N^2$-phosphinyl amidine, an $N^2$-phosphinyl formamidine, an $N^2$-phosphinyl guanidine, or any combination thereof alternatively, an $N^2$-phosphinyl amidine; alternatively, an $N^2$-phosphinyl formamidine; or alternatively, an $N^2$-phosphinyl guanidine. Consequently, in some embodiments, the heteroatomic ligand transition metal compound complex of the catalyst systems described herein can comprise, can consist essentially of, or can be, a diphosphino amine transition metal compound complex, an $N^2$-phosphinyl amidine transition metal compound complex, an $N^2$-phosphinyl formamidine transition metal compound complex, an $N^2$-phosphinyl guanidine transition metal compound complex, or any combination thereof; alternatively, a diphosphino amine transition metal compound complex; alternatively, an $N^2$-phosphinyl amidine transition metal compound complex, an $N^2$-phosphinyl formamidine transition metal compound complex, an $N^2$-phosphinyl guanidine transition metal compound complex, or any combination thereof; alternatively, an $N^2$-phosphinyl amidine transition metal compound complex; alternatively, an $N^2$-phosphinyl formamidine transition metal compound complex; or alternatively, an $N^2$-phosphinyl guanidine transition metal compound complex.

Transition Metal Compounds

Generally, the transition metal compound of the heteroatomic ligand transition metal compound complex has the formula $MX_p$, where M represents the transition metal, X represents a monoanionic ligand, and p represent the number of monoatomic ligands (and the oxidation state of the transition metal, M). The transition metal (M), the monoanionic ligand (X), and p are independent elements of the transition metal compound and are independently described herein. The independent descriptions of the transition metal (M), the monoanionic ligand (X), and p can be utilized without limitation, and in any combination, to further describe the transition metal compound of the heteroatomic ligand transition metal compound complex.

Generally, the transition metal of the heteroatomic ligand transition metal compound complex can comprise, can consist essentially of, or can be, any transition metal. In an embodiment, the transition metal of the heteroatomic ligand transition metal compound complex can consist essentially of, or can be, a Group 5-10 transition metal; alternatively, a Group 6-10 transition metal; alternatively, a Group 6-9 transition metal; alternatively, a Group 6 transition metal; alternatively, a Group 8 transition metal; alternatively, a Group 9 transition metal; or alternatively, a Group 10 transition metal. In some embodiments, the transition metal compound can comprise vanadium, niobium, tantalum, chromium, molybdenum, tungsten, manganese, iron, cobalt, nickel, palladium, or platinum. In other embodiments, the transition metal compound can comprise chromium, molybdenum, tungsten, iron, cobalt, nickel, palladium, or platinum; alternatively, chromium, iron, cobalt, or nickel; or alternatively, iron or cobalt. In other embodiments, the transition metal compound can comprise chromium.

Generally, the transition metal of the transition metal compound ($MX_p$) can have any positive oxidation state available to the transition metal atom. In an embodiment, the transition metal can have an oxidation state of from +2 to +6; alternatively, from +2 to +4; or alternatively, from +2 to +3. In some embodiments, the transition metal of the transition metal compound ($MX_p$) can have an oxidation state of +1; alternatively, +2; alternatively, +3; or alternatively, +4.

Each monoanionic ligand, X, of the transition metal compound independently can be any suitable monoanionic ligand or any monoanionic ligand disclosed herein. In an embodiment, the monoanionic ligand, X, can be a halide, a carboxylate, a β-diketonate, a hydrocarboxide, a nitrate, or a chlorate. In some embodiments, the monoanionic ligand, X, can be a halide, a carboxylate, a β-diketonate, or a hydrocarboxide. In any aspect or embodiment, the hydrocarboxide can be an alkoxide, an aryloxide, or an aralkoxide. Generally, hydrocarboxide (and subdivisions of hydrocarboxide) are the anion analogues of a hydrocarboxy group. In other embodiments, the monoanionic ligand, X, can be a halide, a carboxylate, a β-diketonate, or an alkoxide; or alternatively, a halide or a β-diketonate. In other embodiments, X can be a halide; alternatively, a carboxylate; alternatively, a β-diketonate; alternatively, a hydrocarboxide; alternatively, an alkoxide; or alternatively, an aryloxide. Generally, the number, p, of monoanions can equal the oxidation state of the metal atom. In an embodiment, the number, p, of monoanionic ligands, X, can be from 2 to 6; alternatively, from 2 to 4; alternatively, from 2 to 3; alternatively, 1; alternatively, 2; alternatively, 3; or alternatively, 4.

Generally, each halide monoanionic ligand, X, independently can be fluorine, chlorine, bromine, or iodine; or alternatively, chlorine, bromine, or iodine. In an embodiment, each halide monoanionic ligand, X, can be chlorine; alternatively, bromine; or alternatively, iodine.

Generally, the carboxylate can be a $C_1$ to $C_{20}$ carboxylate, or alternatively, a $C_1$ to $C_{10}$ carboxylate. In an embodiment, each carboxylate monoanionic ligand independently can be acetate, a propionate, a butyrate, a pentanoate, a hexanoate, a heptanoate, an octanoate, a nonanoate, a decanoate, an undecanoate, or a dodecanoate; or alternatively, a pentanoate, a hexanoate, a heptanoate, an octanoate, a nonanoate, a decanoate, an undecanoate, or a dodecanoate. In some embodiments, each carboxylate monoanionic ligand independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, capronate (n-hexanoate); alternatively, n-heptanoate; alternatively, caprylate (n-octanoate); or alternatively, 2-ethylhexanoate. In some embodiments, the carboxylate monoanionic ligand can be triflate (trifluoroacetate).

Generally, the β-diketonate can be any $C_1$ to $C_{20}$ β-diketonate, or alternatively, any $C_1$ to $C_{10}$ β-diketonate. In an embodiment, each β-diketonate independently can be acetylacetonate (i.e., 2,4-pentanedionate), hexafluoroacetylacetone (i.e., 1,1,1,5,5,5-hexafluoro-2,4-pentanediuonate), or benzoylacetonate; alternatively, acetylacetonate; alternatively, hexafluoroacetylacetone; or alternatively, benzoylacetonate.

Generally, the hydrocarboxide can be any $C_1$ to $C_{20}$ hydrocarboxide, or alternatively, any $C_1$ to $C_{10}$ hydrocarboxide. In an embodiment, each hydrocarboxide can be a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide. In an embodiment, each alkoxide monoanionic ligand independently can be methoxide, ethoxide, a propoxide, or a butoxide. In some embodiments, each alkoxide monoanionic ligand independently can be methoxide, ethoxide, isopropoxide, or tert-butoxide; alternatively, methoxide; alternatively, ethoxide; alternatively, iso-propoxide; or alternatively, tert-butoxide. In an aspect, the aryloxide can be phenoxide.

In a non-limiting aspect, the heteroatomic ligand transition metal compound complex of the catalyst systems described herein can comprise, can consist essentially of, or can be, a heteroatomic ligand chromium compound complex. In some particular non-limiting embodiments, the heteroatomic ligand transition metal compound complex of the catalyst systems described herein can comprise, can consist essentially of, or can be, a diphosphino amine chromium compound complex, an $N^2$-phosphinyl amidine chromium compound complex, an $N^2$-phosphinyl formamidine chromium compound complex, an $N^2$-phosphinyl guanidine chromium compound complex, or any combination thereof; alternatively, a diphosphino amine chromium compound complex; alternatively, an $N^2$-phosphinyl amidine chromium compound complex, an $N^2$-phosphinyl formamidine chromium compound complex, an $N^2$-phosphinyl guanidine chromium compound complex, or any combination thereof; alternatively, an $N^2$-phosphinyl amidine chromium compound complex; alternatively, an $N^2$-phosphinyl formamidine chromium compound complex; or alternatively, an $N^2$-phosphinyl guanidine chromium compound complex.

In a non-limiting embodiment, the chromium compound of any heteroatomic ligand chromium compound complex described herein can comprise, can consist essentially of, or consist of, a chromium(II) halide, a chromium(III) halide, a chromium(II) carboxylate, a chromium(III) carboxylate, a chromium(II) β-diketonate, or a chromium(III) β-diketonate. In some non-limiting embodiments, the chromium compound of any heteroatomic ligand chromium compound complex described herein can comprise, can consist essentially of, or consist of, a chromium(II) halide, a chromium(II) carboxylate, or a chromium(II) β-diketonate; or alternatively, a chromium(III) halide, a chromium(III) carboxylate, or a chromium(III) β-diketonate. In other non-limiting embodiments, the chromium compound of any heteroatomic ligand chromium compound complex described herein can comprise, can consist essentially of, or consist of, a chromium(II) halide; alternatively, a chromium (III) halide; alternatively, a chromium (II) carboxylate; alternatively, a chromium(III) carboxylate; alternatively, a chromium(II) β-diketonate; or alternatively, a chromium(III) β-diketonate.

In a non-limiting embodiment, the chromium compound of any heteroatomic ligand chromium compound complex described herein can comprise, can consist essentially of, or consist of, chromium(II) chloride, chromium(III) chloride, chromium(II) fluoride, chromium(III) fluoride, chromium (II) bromide, chromium(III) bromide, chromium(II) iodide, chromium(III) iodide, chromium(II) acetate, chromium(III) acetate, chromium(II) 2-ethylhexanoate, chromium(III) 2-ethylhexanoate, chromium(II) triflate, chromium(III) triflate, chromium(II) nitrate, chromium(III) nitrate, chromium (II) acetylacetonate, chromium(III) acetylacetonate, chromium(II) hexafluoracetylacetonate, chromium(III) hexafluoracetylacetonate, chromium(III) benzoylacetonate, or chromium(III) benzoylacetonate. In some non-limiting embodiments, the chromium compound of any heteroatomic ligand chromium compound complex described herein can comprise, can consist essentially of, or consist of, chromium (III) chloride, chromium(III) fluoride, chromium(III) bromide, chromium(III) iodide, chromium(III) chloride (THF) complex, chromium(III) acetate, chromium(III) 2-ethylhexanoate, chromium(III) triflate, chromium(III) nitrate, chromium(III) acetylacetonate, chromium(III) hexafluoracetylacetonate, or chromium(III) benzoylacetonate. In further embodiments, the chromium compound can be chromium(III) chloride or chromium(III) acetylacetonate; alternatively, chromium(III) chloride; or alternatively, chromium(III) acetylacetonate.

Diphosphino Amine Transition Metal Complexes

In an aspect, the heteroatomic ligand transition metal compound complex of the catalyst systems described herein can comprise, can consist essentially of, or can be, a diphosphino amine transition metal compound complex having Structure PNPTMC1 or Structure PNPTMC2; alternatively, Structure PNPTMC1; or alternatively, Structure PNPTMC2.

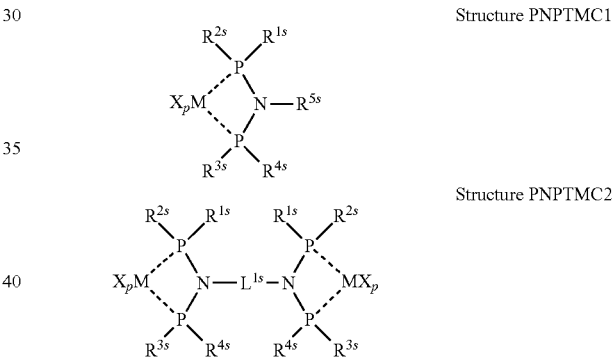

Structure PNPTMC1

Structure PNPTMC2

In the diphosphino amine transition metal compound complex having Structure PNPTMC1 and Structure PNPTMC2, $MX_p$ represents the transition metal compound of the diphosphino amine transition metal compound complex, while $[(R^{1s})(R^{2s})P]N(R^{5s})[P(R^{3s})(R^{4s})]$ and $[(R^{1s})(R^{2s})P][(R^{3s})(R^{4s})P]N(L^{1s})N[P(R^{1s})(R^{2s})P][P(R^{3s})(R^{4s})]$ represent the diphosphino amine of the diphosphino amine transition metal compound complex. Generally, the transition metal compound ($MX_p$) and each $R^{1s}$, $R^{2s}$, $R^{3s}$, $R^{4s}$, $R^{5s}$, and $L^{1s}$ of the respective diphosphino amine of the diphosphino amine transition metal compound complex having Structure PNPTMC1 and Structure PNPTMC2 are independent elements of the diphosphino amine transition metal compound complex having Structure PNPTMC1 and Structure PNPTMC2 and are described independently herein. The independent descriptions of ($MX_p$), $R^{1s}$, $R^{2s}$, $R^{3s}$, $R^{4s}$, $R^{5s}$, and $L^{1s}$ can be utilized without limitation, and in any combination, to further describe any the diphosphino amine transition metal compound complexes having Structure PNPTMC1 and/or Structure PNPTMC2.

Generally, each $R^{1s}$, $R^{2s}$, $R^{3s}$, and $R^{4s}$ of the diphosphino amine having Structure PNPTMC1 and/or Structure PNPTMC2 independently can be an organyl group; alternatively, an organyl group consisting of inert functional groups; or alternatively, a hydrocarbyl group. In an embodiment, the organyl group which can be utilized as $R^{1s}$, $R^{2s}$, $R^{3s}$, and $R^{4s}$ can be a $C_1$ to $C_{30}$, a $C_1$ to $C_{20}$, a $C_1$ to $C_{15}$, a $C_1$ to $C_{10}$, or a $C_1$ to $C_5$ organyl group. In an embodiment, the organyl group consisting of inert functional groups which can be utilized as $R^{1s}$, $R^{2s}$, $R^{3s}$, and $R^{4s}$ can be a $C_1$ to $C_{30}$, a $C_1$ to $C_{20}$, a $C_1$ to $C_{15}$, a $C_1$ to $C_{10}$, or a $C_1$ to $C_5$ organyl group consisting of inert functional groups. In an embodiment, the hydrocarbyl group which can be utilized as $R^{1s}$, $R^{2s}$, $R^{3s}$, and $R^{4s}$ can be a $C_1$ to $C_{30}$, a $C_1$ to $C_{20}$, a $C_1$ to $C_{15}$, a $C_1$ to $C_{10}$, or a $C_1$ to $C_5$ hydrocarbyl group. In further embodiments, $R^{1s}$ and $R^{2s}$, and/or $R^{3s}$ and $R^{4s}$ can be joined to form a ring or a ring system.

In an embodiment, each $R^{1s}$, $R^{2s}$, $R^{3s}$, and $R^{4s}$ of Structure PNPTMC1 and/or Structure PNPTMC2 independently can be an alkyl group, a substituted alkyl group, a cycloalkyl group, a substituted cycloalkyl group, an aryl group, a substituted aryl group, an aralkyl group, or a substituted aralkyl group. In some embodiments, each $R^{1s}$, $R^{2s}$, $R^{3s}$, and $R^{4s}$ of Structure PNPTMC1 and/or Structure PNPTMC2 independently can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, each $R^{1s}$, $R^{2s}$, $R^{3s}$, and $R^{4s}$ of Structure PNPTMC1 and/or Structure PNPTMC2 independently can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, each alkyl group which can be utilized as $R^{1s}$, $R^{2s}$, $R^{3s}$, and $R^{4s}$ independently can be a $C_1$ to $C_{20}$, a $C_1$ to $C_{10}$, or a $C_1$ to $C_5$ alkyl group. In any aspect or embodiment disclosed herein, each substituted alkyl group which can be utilized as $R^{1s}$, $R^{2s}$, $R^{3s}$, and $R^{4s}$ independently can be a $C_1$ to $C_{20}$, a $C_1$ to $C_{10}$, or a $C_1$ to $C_5$ substituted alkyl group. In any aspect or embodiment disclosed herein, each cycloalkyl group which can be utilized as $R^{1s}$, $R^{2s}$, $R^{3s}$, and $R^{4s}$ independently can be a $C_4$ to $C_{20}$, a $C_4$ to $C_{15}$, or a $C_4$ to $C_{10}$ cycloalkyl group. In any aspect or embodiment disclosed herein, each substituted cycloalkyl group which can be utilized as $R^{1s}$, $R^{2s}$, $R^{3s}$, and $R^{4s}$ independently can be a $C_4$ to $C_{20}$, a $C_4$ to $C_{15}$, or a $C_4$ to $C_{10}$ substituted cycloalkyl group. In any aspect or embodiment disclosed herein, each aryl group which can be utilized as $R^{1s}$, $R^{2s}$, $R^{3s}$, and $R^{4s}$ independently can be a $C_6$ to $C_{20}$, a $C_6$ to $C_{15}$, or a $C_6$ to $C_{10}$ aryl group. In any aspect or embodiment disclosed herein, each substituted aryl group which can be utilized as $R^{1s}$, $R^{2s}$, $R^{3s}$, and $R^{4s}$ independently can be a $C_6$ to $C_{20}$, a $C_6$ to $C_{15}$, or a $C_6$ to $C_{10}$ substituted aryl group. In any aspect or embodiment disclosed herein, each aralkyl group which can be utilized as $R^{1s}$, $R^{2s}$, $R^{3s}$, and $R^{4s}$ independently can be a $C_7$ to $C_{20}$, a $C_7$ to $C_{15}$, or a $C_7$ to $C_{10}$ aralkyl group. In any aspect or embodiment disclosed herein, each substituted aryl group which can be utilized as $R^{1s}$, $R^{2s}$, $R^{3s}$, and $R^{4s}$ independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarboxy groups, and substituent hydrocarboxy groups can be utilized without limitation to further describe $R^{1s}$, $R^{2s}$, $R^{3s}$, and/or $R^{4s}$.

In an embodiment, one or more of $R^{1s}$, $R^{2s}$, $R^{3s}$, and $R^{4s}$ can be a methyl group, an ethyl group, a propyl group, a butyl group, a pentyl group, a hexyl group, a heptyl group, or an octyl group. In some embodiments, one or more of $R^{1s}$, $R^{2s}$, $R^{3s}$, and $R^{4s}$ can be a methyl group, an ethyl group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some embodiments, the alkyl groups which can be utilized as $R^{1s}$, $R^{2s}$, $R^{3s}$, and $R^{4s}$ can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group (general or specific) which can be utilized as $R^{1s}$, $R^{2s}$, $R^{3s}$, and/or $R^{4s}$.

In an embodiment, one or more of $R^{1s}$, $R^{2s}$, $R^{3s}$, and $R^{4s}$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an embodiment, the substituted cycloalkyl group, which can be utilized for one of more of $R^{1s}$, $R^{2s}$, $R^{3s}$, and $R^{4s}$, can be a 2-substituted cyclohexyl group, a 2,6-disubstituted cyclohexyl group, a 2-substituted cyclopentyl group, or a 2,6-disubstituted cyclopentyl group; alternatively, a 2-substituted cyclohexyl group or a 2,6-disubstituted cyclohexyl group; alternatively, a 2-substituted cyclopentyl group or a 2,6-disubstituted cyclopentyl group; alternatively, a 2-substituted cyclohexyl group or a 2-substituted cyclopentyl group; alternatively, a 2,6-disubstituted cyclohexyl group or a 2,6-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,6-disubstituted cyclopentyl group. In an embodiment, one or more substituents of a multi-substituted cycloalkyl group utilized as $R^{1s}$, $R^{2s}$, $R^{3s}$, and/or $R^{4s}$ can be the same or different; alternatively, all the substituents of a multi-substituted cycloalkyl group can be the same; or alternatively, all the substituents of a multi-substituted cycloalkyl group can be different. Each substituent of a substituted cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^{1s}$, $R^{2s}$, $R^{3s}$, and/or $R^{4s}$.

In a non-limiting embodiment, any one or more of $R^{1s}$, $R^{2s}$, $R^{3s}$, and $R^{4s}$ can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^{1s}$, $R^{2s}$, $R^{3s}$, and $R^{4s}$. Generally, the alkyl substituents of a disubstituted cyclohexyl or cyclopentyl group can be the same, or alternatively, the alkyl substituents can be different. In some non-limiting embodiments, any one or more of $R^{1s}$, $R^{2s}$, $R^{3s}$, and $R^{4s}$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting embodiments, one or more of $R^{1s}$, $R^{2s}$, $R^{3s}$, and $R^{4s}$ can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an embodiment, one or more of $R^{1s}$, $R^{2s}$, $R^{3s}$, and $R^{4s}$ can be a phenyl group or a substituted phenyl group; alternatively, a phenyl group; or alternatively, a substituted phenyl group. In an embodiment, the substituted phenyl group which can be utilized for one or more of $R^{1s}$, $R^{2s}$, $R^{3s}$, and $R^{4s}$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an embodiment, one or more substituents of a multi-substituted phenyl group utilized as $R^{1s}$, $R^{2s}$, $R^{3s}$, and/or $R^{4s}$ can be the same or different; alternatively, all the substituents can be the same; or alternatively, all the substituents can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy group can be utilized without limitation to further describe a substituted phenyl group (general or specific) which can be utilized as $R^{1s}$, $R^{2s}$, $R^{3s}$, and/or $R^{4s}$.

In a non-limiting embodiment, one or more of $R^{1s}$, $R^{2s}$, $R^{3s}$, and $R^{4s}$ can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^{1s}$, $R^{2s}$, $R^{3s}$, and/or $R^{4s}$. Generally, the alkyl substituents of dialkylphenyl groups (general or specific) or trialkylphenyl groups (general or specific) can be the same, or alternatively, the alkyl substituents can be different. In some non-limiting embodiments, one or more of $R^{1s}$, $R^{2s}$, $R^{3s}$, and $R^{4s}$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; or alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting embodiment, one or more of $R^{1s}$, $R^{2s}$, $R^{3s}$, and $R^{4s}$ can be a phenyl group, a 2-alkoxyphenyl group, or a 4-alkoxyphenyl group. In some non-limiting embodiments, one or more of $R^{1s}$, $R^{2s}$, $R^{3s}$, and $R^{4s}$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group.

In a non-limiting embodiment, one or more of $R^{1s}$, $R^{2s}$, $R^{3s}$, and $R^{4s}$ can be a phenyl group, a 2-halophenyl group, a 4-halophenyl group, or a 2,6-dihalophenyl group. Generally, the halides of a dihalophenyl group can be the same, or alternatively, the halides can be different. In some embodiments, one or more of $R^{1s}$, $R^{2s}$, $R^{3s}$, and $R^{4s}$ can be a phenyl group, a 2-fluorophenyl group, a 4-fluorophenyl group, or a 2,6-difluorophenyl group.

In an embodiment, one or more of $R^{1s}$, $R^{2s}$, $R^{3s}$, and $R^{4s}$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group (general or specific) which can be utilized as $R^{1s}$, $R^{2s}$, $R^{3s}$, and/or $R^{4s}$.

Generally, $R^{5s}$ of the diphosphino amine transition metal compound having Structure PNPTMC1 can be an organyl group; alternatively, an organyl group consisting of inert functional groups; or alternatively, a hydrocarbyl group. In an embodiment, the organyl group which can be utilized as $R^{5s}$ can be a $C_1$ to $C_{20}$, a $C_1$ to $C_{15}$, a $C_1$ to $C_{10}$, or a $C_1$ to $C_5$ organyl group. In an embodiment, the organyl group consisting of inert functional groups which can be utilized as $R^{5s}$ can be a $C_1$ to $C_{20}$, a $C_1$ to $C_{15}$, a $C_1$ to $C_{10}$, or a $C_1$ to $C_5$ organyl group consisting of inert functional groups. In an embodiment, the hydrocarbyl group which can be utilized as $R^{5s}$ can be a $C_1$ to $C_{20}$, a $C_1$ to $C_{15}$, a $C_1$ to $C_{10}$, or a $C_1$ to $C_5$ hydrocarbyl group.

In an embodiment, $R^{5s}$ of Structure PNPTMC1 can be an alkyl group, a substituted alkyl group, a cycloalkyl group, a substituted cycloalkyl group, an aryl group, a substituted aryl group, an aralkyl group, or a substituted aralkyl group. In some embodiments, $R^{5s}$ of Structure PNPTMC1 can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^{5s}$ of Structure PNPTMC1 can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, the alkyl group which can be utilized as $R^{5s}$ can be a $C_1$ to $C_{20}$, a $C_1$ to $C_{10}$, or a $C_1$ to $C_5$ alkyl group. In any aspect or embodiment disclosed herein, the substituted alkyl group which can be utilized as $R^{5s}$ can be a $C_1$ to $C_{30}$, a $C_1$ to $C_{20}$, a $C_1$ to $C_{10}$, or a $C_1$ to $C_5$ substituted alkyl group. In any aspect or embodiment disclosed herein, the cycloalkyl group which can be utilized as $R^{5s}$ can be a $C_4$ to $C_{20}$, a $C_4$ to $C_{15}$, or a $C_4$ to $C_{10}$ cycloalkyl group. In any aspect or embodiment disclosed herein, the substituted cycloalkyl group which can be utilized as $R^{5s}$ can be a $C_4$ to $C_{20}$, a $C_4$ to $C_{15}$, or a $C_4$ to $C_{10}$ substituted cycloalkyl group. In any aspect or embodiment disclosed herein, the aryl group which can be utilized as $R^{5s}$ can be a $C_6$ to $C_{20}$, a $C_6$ to $C_{15}$, or a $C_6$ to $C_{10}$ aryl group. In any aspect or embodiment disclosed herein, the substituted aryl group which can be utilized as $R^{5s}$ can be a $C_6$ to $C_{20}$, a $C_6$ to $C_{15}$, or a $C_6$ to $C_{10}$ substituted aryl group. In any aspect or embodiment disclosed herein, each aralkyl group which can be utilized as $R^{5s}$ can be a $C_7$ to, a $C_7$ to $C_{15}$, or a $C_7$ to $C_{10}$ aralkyl group. In any aspect or embodiment disclosed herein, the substituted aryl group which can be utilized as $R^{5s}$ can be a $C_7$ to $C_{20}$, a $C_7$ to, or a $C_7$ to $C_{10}$ substituted aralkyl group. Each substituent of a substituted alkyl group (general or specific), substituted cycloalkyl group (general or specific), substituted aryl group (general or specific), and/or substituted aralkyl group (general or specific) can be a halogen, hydrocarbyl group, or a hydrocarboxy group; alternatively, a halogen or a hydrocarbyl group; alternatively, a halogen or a hydrocarboxyl group; alternatively, a hydrocarbyl group or a hydrocarboxy group; alternatively, a halogen; alternatively, a hydrocarbyl group; or alternatively, a hydrocarboxy group. Substituent halogens, hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted $R^{5s}$ group.

In an embodiment, $R^{5s}$ can be a methyl group, an ethyl group, a propyl group, a butyl group, a pentyl group, a hexyl group, a heptyl group, or an octyl group. In some embodiments, $R^{5s}$ can be a methyl group, an ethyl group, an n-propyl (1-propyl) group, an isopropyl (2-propyl) group, an n-butyl (1-butyl) group, a sec-butyl (2-butyl) group, an isobutyl (2-methyl-1-propyl) group, a tert-butyl (2-methyl-2-propyl) group, an n-pentyl (1-pentyl) group, a 2-pentyl group, a 3-pentyl group, a 2-methyl-1-butyl group, a tert-pentyl (2-methyl-2-butyl) group, a 3-methyl-1-butyl group, a 3-methyl-2-butyl group, or a neo-pentyl (2,2-dimethyl-1-propyl) group; alternatively, a methyl group, an ethyl group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some embodiments, the alkyl groups which can be utilized as $R^{5s}$ can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently described herein and these substituent groups can be utilized without limitation to further describe a substituted alkyl group (general or specific) which can be utilized as $R^{5s}$.

In an embodiment, $R^{5s}$ can be a cyclopentyl group, a substituted cyclopentyl group, a cyclohexyl group, a substituted cyclohexyl group; alternatively, a cyclopentyl group or a substituted cyclopentyl group; alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In further embodiments, $R^{5s}$ can be a 2-substituted cyclohexyl group, a 2,6-disubstituted cyclohexyl group, a 2-substituted cyclopentyl group, or a 2,6-disubstituted cyclopentyl group; alternatively, a 2-substituted cyclohexyl group or a 2,6-disubstituted cyclohexyl group; alternatively, a 2-substituted cyclohexyl group or a 2,6-disubstituted cyclohexyl group; alternatively, a 2-substituted cyclopentyl group or a 2,6-disubstituted cyclopentyl group; alternatively, a 2-substituted cyclohexyl group or a 2-substituted cyclopentyl group; alternatively, a 2,6-disubstituted cyclohexyl group or a 2,6-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,6-disubstituted cyclopentyl group. In an embodiment, one or more substituents of a multi-substituted cycloalkyl group utilized as $R^{5s}$ can be the same or different; alternatively, all the substituents of a multi-substituted cycloalkyl group can be the same; or alternatively, all the substituents of a multi-substituted cycloalkyl group can be different. Each substituent of a cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently described herein and these substituent groups can be utilized without limitation to further describe a substituted cycloalkyl group (general or specific) which can be utilized as $R^{5s}$.

In a non-limiting embodiment, $R^{5s}$ can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^{5s}$. Generally, the alkyl substituents of a disubstituted cyclohexyl or cyclopentyl group can be the same, or alternatively, the alkyl substituents can be different. In some non-limiting embodiments, $R^5$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting embodiments, $R^{5s}$ can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group. In an embodiment, $R^{5s}$ can be a cyclopentyl group, a 2-methylcyclopentyl group, a cyclohexyl group, or a 2-methylcyclohexyl group; alternatively, a cyclopentyl group or a cyclohexyl group; or alternatively, a 2-methylcyclopentyl group or a 2-methylcyclohexyl group.

In an embodiment, $R^5$ can be a phenyl group or a substituted phenyl group; alternatively, a phenyl group; or alternatively, a substituted phenyl group. In some embodiments, $R^{5s}$ can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,4-disubstituted phenyl group or a 2,6-disubstituted phenyl group; alternatively, a 2-substituted phenyl group; alternatively, a 4-substituted phenyl group; alternatively, a 2,4-disubstituted phenyl group; alternatively, a 2,6-disubstituted phenyl group; or alternatively, a 2,4,6-trisubstituted phenyl group. In an embodiment, one or more substituents of a multi-substituted phenyl group utilized as $R^{5s}$ can be the same or different; alternatively, all the substituents can be the same, or alternatively, all the substituents can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently described herein and these substituent groups can be utilized without limitation to further describe a substituted phenyl group (general or specific) which can be utilized as $R^{5s}$ In a non-limiting embodiment, $R^{5s}$ can be a phenyl group, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group, a 2,4-dialkylphenyl group, a 2,6-dialkylphenyl group, or a 2,4,6-trialkylphenyl group. Alkyl substituent groups (general and specific) are independently described herein and these alkyl substituent groups can be utilized, without limitation, to further describe any alkyl substituted phenyl group which can be utilized as $R^{5s}$. Generally, the alkyl substituents of dialkylphenyl groups (general of specific) or trialkylphenyl groups (general or specific) can be the same, or alternatively, the alkyl substituents can be different. In some non-limiting embodiments, $R^5$ can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2,6-dimethylphenyl group, or a 2,4,6-trimethylphenyl group.

Generally, $L^{1s}$ of the diphosphino amine having Structure PNPTMC2 can be an organylene group; alternatively, an organylene group consisting of inert functional groups; or alternatively, a hydrocarbylene group. In an embodiment, the organylene group which can be utilized as $L^{1s}$ can be a $C_1$ to $C_{20}$, a $C_1$ to $C_{15}$, or a $C_1$ to $C_{10}$ organylene group. In an embodiment, the organylene group consisting of inert functional groups which can be utilized as $L^{1s}$ can be a $C_1$ to $C_{20}$, a $C_1$ to $C_{15}$, or a $C_1$ to $C_{10}$ organylene group consisting of inert functional groups. In an embodiment, the hydrocarbylene group which can be utilized as $L^{1s}$ can be a $C_1$ to $C_{20}$, a $C_1$ to $C_{15}$, or a $C_1$ to $C_{10}$ hydrocarbylene group. In an embodiment, $L^{1s}$ of the diphosphino amine having Structure PNPTMC2 can be a $C_1$ to $C_{20}$ alkylene group, or alternatively, a $C_1$ to $C_{10}$ alkylene group.

In an embodiment, $L^{1s}$ of the diphosphino amine having Structure PNPTMC2 can be $-(CR^PR^{P'})_m-$ where each $R^P$ and $R^{P'}$ can independently be hydrogen, methyl, ethyl, propyl, isopropyl, or butyl groups and m can be an integer from 1 to 12. In some embodiments, $L^{1s}$ can be a methylene group (—CH₂—), an ethylene group (—CH₂CH₂—), a propylene group (—CH₂CH₂CH₂—), a —CH(CH₃)CH₂— group, —C(CH₃)₂— group, a butylene group (—CH₂CH₂CH₂—CH₂—), or a —CH₂CH(CH₃)—CH₂— group. In other embodiments, $L^{1s}$ can be a methylene group (—CH₂—), an ethylene group (—CH₂CH₂—), or a —CH(CH₃)CH₂— group; alternatively, a methylene group (—CH₂—); alternatively, an ethylene group (—CH₂CH₂—); alternatively, a propylene group (—CH₂CH₂CH₂—); alternatively, a —CH(CH₃)CH₂— group; alternatively, a —C(CH₃)₂— group; or alternatively, a —CH₂CH(CH₃)—CH₂— group.

In an embodiment, $L^{1s}$ of the diphosphino amine having Structure PNPTMC2 can be 1,2-cyclohexylene, a substituted 1,2-cyclohexylene, 1,3-cyclohexylene, a substituted 1,3-cyclohexylene, 1,4-cyclohexylene, a substituted 1,4-cyclohexylene, 3,3'-bicyclohexylene, a substituted 3,3'-bicyclohexylene, 4,4'-bicyclohexylene, a substituted 4,4'-bicyclohexylene, bis(3-cyclohexylene)methane, a substituted bis(3-cyclohexylene)methane, bis(4-cyclohexylene)methane, a substituted bis(4-cyclohexylene)methane, 1,2-bis(3-cyclohexylene)ethane, a substituted 1,2-bis(3-cyclohexylene)ethane, 1,2-bis(4-cyclohexylene)ethane, a substituted 1,2-bis(4-cyclohexylene)ethane, 1,2-bis(3-cyclohexylene)propane, a substituted 1,2-bis(3-cyclohexylene)propane, 1,2-bis(4-cyclohexylene)propane, a substituted 1,2-bis(4-cyclohexylene)propane, 2,2-bis(3-cyclohexylene)-propane, a substituted 2,2-bis(3-cyclohexylene)propane, 2,2-bis(4-cyclohexylene)propane, or a substituted 2,2-bis(4-cyclohexylene)propane. In some embodiments, $L^{1s}$ of the diphosphino amine having Structure PNPTMC2 can be a substituted 1,2-cyclohexylene, a substituted 1,3-cyclohexylene, a substituted 1,4-cyclohexylene, a substituted 3,3'-bicyclohexylene, a substituted 4,4'-bicyclohexylene, a substituted bis(3-cyclohexylene)methane, a substituted bis(4-cyclohexylene)methane, a substituted 1,2-bis(3-cyclohexylene)ethane, a substituted 1,2-bis(4-cyclohexylene)ethane, a substituted 1,2-bis(3-cyclohexylene)propane, a substituted 1,2-bis(4-cyclohexylene)propane, a substituted 2,2-bis(3-cyclohexylene)propane, or a substituted 2,2-bis(4-cyclohexylene)propane. In an embodiment, each substituent of a substituted cyclohexylene, a substituted bis(cyclohexylene)methane, a substituted bis(cyclohexylene)ethane, or a substituted 1,2-bis(3-cyclohexylene)propane which can be utilized as $L^{1s}$ can be a hydrocarbyl group. Substituent groups (general and specific) are independently disclosed herein and can be utilized without limitation to further describe a substituted cyclohexylene (general or specific), a substituted bis(cyclohexylene)methane (general or specific), a substituted bis(cyclohexylene)ethane (general or specific), or a substituted 1,2-bis(3-cyclohexylene)propane (general or specific) which can be utilized as $L^{1s}$.

In an embodiment, $L^{1s}$ of the diphosphino amine having Structure PNPTMC2 can be 1,2-phenylene, a substituted 1,2-phenylene, 1,3-phenylene, a substituted 1,3-phenylene, 1,4-phenylene, a substituted 1,4-phenylene, 3,3'-biphenylene, a substituted 3,3'-biphenylene, 4,4'-biphenylene, a substituted 4,4'-biphenylene, bis(3-phenylene)methane, a substituted bis(3-phenylene)methane, bis(4-phenylene)methane, a substituted bis(4-phenylene)methane, 1,2-bis(3-phenylene)ethane, a substituted 1,2-bis(3-phenylene)ethane, 1,2-bis(4-phenylene)ethane, a substituted 1,2-bis(4-phenylene)ethane, 1,2-bis(3-phenylene)propane, a substituted 1,2-bis(3-phenylene)propane, 1,2-bis(4-phenylene)propane, a substituted 1,2-bis(4-phenylene)propane, 2,2-bis(3-phenylene)propane, a substituted 2,2-bis(3-phenylene)propane, 2,2-bis(4-phenylene)propane, or a substituted 2,2-bis(4-phenylene)propane. In some embodiments, $L^{1s}$ of the diphosphino amine having Structure PNPTMC2 can be a substituted 1,2-phenylene, a substituted 1,3-phenylene, a substituted 1,4-phenylene, a substituted 3,3'-biphenylene, a substituted 4,4'-biphenylene, a substituted bis(3-phenylene)methane, a substituted bis(4-phenylene)methane, a substituted 1,2-bis(3-phenylene)ethane, a substituted 1,2-bis(4-phenylene)ethane, a substituted 1,2-bis(3-phenylene)propane, a substituted 1,2-bis(4-phenylene)propane, a substituted 2,2-bis(3-phenylene)propane, or a substituted 2,2-bis(4-phenylene)propane. In an embodiment, each substituent of a substituted phenylene (general or specific), a substituted biphenylene (general or specific), a substituted bis(phenylene)methane (general or specific), a substituted bis(phenylene)ethane (general or specific), and/or a substituted bis(phenylene)propane (general or specific) which can be utilized as $L^{1s}$ can be a hydrocarbyl group. Substituent hydrocarbyl groups (general and specific) are independently disclosed herein and can be utilized without limitation to further describe a substituted phenylene (general or specific), a substituted biphenylene (general or specific), a substituted bis(phenylene)methane (general or specific), a substituted bis(phenylene)ethane (general or specific), and/or a substituted bis(phenylene)propane (general or specific) which can be utilized as $L^{1s}$.

In some particular embodiments, the heteroatomic ligand transition metal compound complex of the catalyst systems described herein can comprise, can consist essentially of, or can be, a diphosphino amine chromium compound complex, having Structure PNPCrC1 or Structure PNPCr2; alternatively, Structure PNPCr1; or alternatively, Structure PNPCr2. Generally, $R^{1s}$, $R^{2s}$, $R^{3s}$, $R^{4s}$, $R^{5s}$, $L^{1s}$, X, and p for the diphosphino amine chromium compound complexes can be any group disclosed herein for the respective diphosphino amine transition metal compound complexes having Structure PNPTMC1 and/or Structure PNPTMC2.

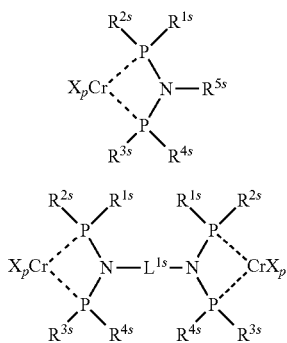

Structure PNPCr1

Structure PNPCr2

In a non-limiting embodiment, the diphosphinoamine ligand of the diphosphino amine transition metal compound complex can be any one or more of PNP 1, PNP 2, PNP 3, PNP 4, PNP 5, and PNP 6 (Ph is phenyl). In some non-limiting embodiments, the diphosphino amine transition metal compound complex can be a chromium compound complex of any one or more of PNP 1, PNP 2, PNP 3, PNP 4, PNP 5, and PNP 6. In other non-limiting embodiments, the diphosphino amine transition metal compound complex can be a chromium(III) chloride or chromium(III) acetylacetonate complex of any one or more of PNP 1, PNP 2, PNP 3, PNP 4, PNP 5, and PNP 6.

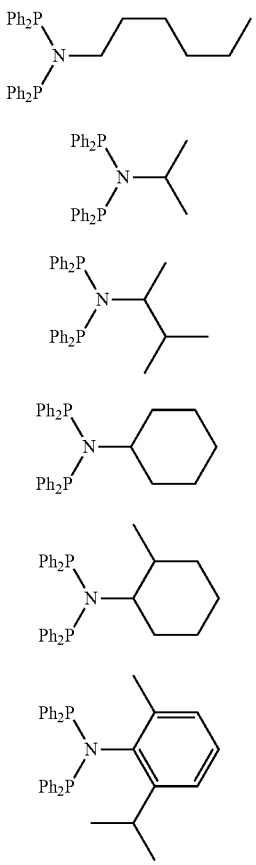

PNP 1

PNP 2

PNP 3

PNP 4

PNP 5

PNP 6

$N^2$-Phosphinyl Amidine, $N^2$-Phosphinyl Formamidine, and $N^2$-Phosphinyl Guanidine Ligands In an aspect, the heteroatomic ligand transition metal compound complex of the catalyst systems described herein can comprise, can consist essentially of, or can be, an $N^2$-phosphinyl formamidine transition metal compound complex having the Structure NPFTMC1, an $N^2$-phosphinyl amidine transition metal compound complex having the Structure NPATMC1, or an $N^2$-phosphinyl guanidine transition metal compound complex having the Structure GuTMC1, GuTMC2, GuTMC3, GuTMC4, or GuTMC5. In an embodiment, the heteroatomic ligand transition metal compound complex of the catalyst systems described herein can comprise, can consist essentially of, or can be, an $N^2$-phosphinyl formamidine transition metal compound complex having the Structure NPFTMC1; alternatively, an $N^2$-phosphinyl amidine transition metal compound complex having the Structure NPATMC1; or alternatively, an $N^2$-phosphinyl guanidine transition metal compound complex having the Structure GuTMC1, GuTMC2, GuTMC3, GuTMC4, or GuTMC5; alternatively, an $N^2$-phosphinyl guanidine transition metal compound complex having the Structure GuTMC1; alternatively, an $N^2$-phosphinyl guanidine transition metal compound complex having the Structure GuTMC2; alternatively, an $N^2$-phosphinyl guanidine transition metal compound complex having the Structure GuTMC3; alternatively, an $N^2$-phosphinyl guanidine transition metal compound complex having the Structure GuTMC4; or alternatively, an $N^2$-phosphinyl guanidine transition metal compound complex having the Structure GuTMC5.

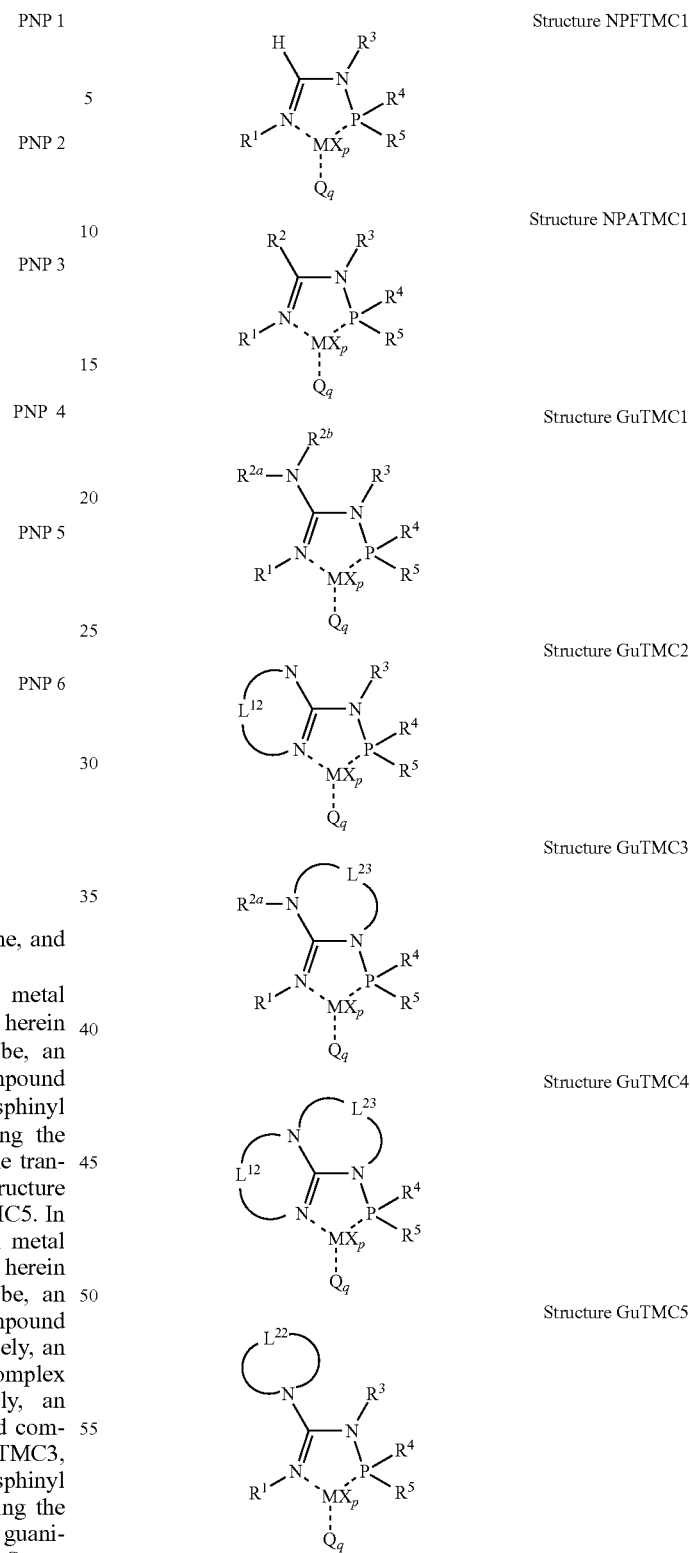

Structure NPFTMC1

Structure NPATMC1

Structure GuTMC1

Structure GuTMC2

Structure GuTMC3

Structure GuTMC4

Structure GuTMC5

Within the $N^2$-phosphinyl formamidine transition metal compound complexes and the $N^2$-phosphinyl amidine transition metal compound complexes, the nitrogen participating in a double bond with the central carbon atom is referred to as the $N^1$ nitrogen and the nitrogen atom participating in a single bond with the central carbon atom is referred to as the $N^2$ nitrogen. Similarly, within the $N^2$-phosphinyl guanidine transition metal compound complexes, the nitrogen participating in a double bond with the central carbon atom of the guanidine core is referred to as the $N^1$ nitrogen, the nitrogen atom participating in a single bond with the central carbon atom of the guanidine core and a bond with the phosphorus atom of the phosphinyl group is referred to as the $N^2$ nitrogen, and the remaining nitrogen atom participating in a single bond with the central carbon atom of the guanidine core is referred to as the $N^3$ nitrogen. It should be noted that the guanidine group of the guanidine in the $N^2$-phosphinyl guanidine transition metal complexes can be a portion of a larger group which does not contain guanidine in its name. For example, while the compound 7-dimethylphosphinylimidazo[1,2-a]imidazole could be classified as a compound having an imidazo[1,2-a]imidazole core (or a compound having a phosphinylimidazo[1,2-a]imidazole group), 7-dimethylphosphinylimidazo[1,2-a]imidazole would still be classified as a compound having a guanidine core (or as a compound having a guanidine group), since it contains the defined general structure of the guanidine compound.

$R^1$, $R^3$, $R^4$, and $R^5$ within the $N^2$-phosphinyl formamidine transition metal complexes having Structure NPFTMC1, the $N^2$-phosphinyl amidine transition metal complexes having Structure NPATMC1, and the $N^2$-phosphinyl guanidine transition metal complexes having the Structures GuTMC1, GuTMC2, GuTMC3, GuTMC4, and/or GuTMC5 are independently described herein and can be utilized without limitation to further describe the $N^2$-phosphinyl formamidine transition metal complexes having Structure NPFTMC1, the $N^2$-phosphinyl amidine transition metal complexes having Structure NPATMC1, and/or the $N^2$-phosphinyl guanidine transition metal complexes having the Structures GuTMC1, GuTMC2, GuTMC3, GuTMC4, and/or GuTMC5. Similarly, $R^2$ within the $N^2$-phosphinyl amidine chromium compound complexes having Structure NPACr1 are independently described herein and can be utilized without limitation to further describe the $N^2$-phosphinyl amidine chromium compound complexes having Structure NPACr1. Similarly, $R^{2a}$, $R^{2b}$, $L^{12}$, $L^{22}$, and $L^{23}$ within the $N^2$-phosphinyl guanidine transition metal complexes having the Structures GuTMC1, GuTMC2, GuTMC3, GuTMC4, or GuTMC5 are independently described herein and can be utilized without limitation to further describe the $N^2$-phosphinyl guanidine transition metal complexes having the Structures GuTMC1, GuTMC2, GuTMC3, GuTMC4, and/or GuTMC5. $MX_p$, Q, and q of the $N^2$-phosphinyl formamidine transition metal complexes, the $N^2$-phosphinyl amidine transition metal complexes, and the $N^2$-phosphinyl guanidine transition metal complexes are independently described herein and can be utilized in any combination, and without limitation, to further describe the $N^2$-phosphinyl formamidine transition metal complexes, the $N^2$-phosphinyl amidine transition metal complexes, and the $N^2$-phosphinyl guanidine transition metal complexes. Additionally, $MX_p$, Q, and q can be combined, without limitation, with the independently described $R^1$, $R^2$, $R^3$, $R^4$, $R^5$, $R^{2a}$, $R^{2b}$, $L^{12}$, $L^{12}$, and $L^{23}$ to further describe the $N^2$-phosphinyl formamidine transition metal complexes, the $N^2$-phosphinyl amidine transition metal complexes, and the $N^2$-phosphinyl guanidine transition metal complexes which have an $R^1$, $R^2$, $R^3$, $R^4$, $R^5$, $R^{2a}$, $R^{2b}$, $L^{12}$, $L^{12}$, and/or $L^{23}$ group.

Generally, $R^1$ of the $N^2$-phosphinyl formamidine transition metal complexes, the $N^2$-phosphinyl amidine transition metal complexes, and/or the $N^2$-phosphinyl guanidine transition metal complexes which have an $R^1$ group can be an organyl group; alternatively, an organyl group consisting essentially of inert functional groups; or alternatively, a hydrocarbyl group. In an embodiment, the $R^1$ organyl group of the $N^2$-phosphinyl formamidine transition metal complexes, the $N^2$-phosphinyl amidine transition metal complexes, and/or the $N^2$-phosphinyl guanidine transition metal complexes, which have an $R^1$ group, can be a $C_1$ to $C_{20}$, a $C_1$ to $C_{15}$, a $C_1$ to $C_{10}$, or a $C_1$ to $C_5$ organyl group. In an embodiment, the $R^1$ organyl group consisting essentially of inert functional groups of the $N^2$-phosphinyl formamidine transition metal complexes, the $N^2$-phosphinyl amidine transition metal complexes, and/or the $N^2$-phosphinyl guanidine transition metal complexes, which have an $R^1$ group, can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, the $R^1$ hydrocarbyl group of the $N^2$-phosphinyl formamidine transition metal complexes, the $N^2$-phosphinyl amidine transition metal complexes, and/or the $N^2$-phosphinyl guanidine transition metal complexes, which have an $R^1$ group, can be a $C_1$ to $C_{20}$, a $C_1$ to $C_{15}$, a $C_1$ to $C_{10}$, or a $C_1$ to $C_5$ hydrocarbyl group.

In an embodiment, $R^1$ of the $N^2$-phosphinyl formamidine transition metal complexes, the $N^2$-phosphinyl amidine transition metal complexes, and/or the $N^2$-phosphinyl guanidine transition metal complexes, which have an $R^1$ group, can be an alkyl group, a substituted alkyl group, a cycloalkyl group, a substituted cycloalkyl group, an aryl group, a substituted aryl group, an aralkyl group, or a substituted aralkyl group. In some embodiments, $R^1$ of the $N^2$-phosphinyl formamidine transition metal complexes, the $N^2$-phosphinyl amidine transition metal complexes, and/or the $N^2$-phosphinyl guanidine transition metal complexes, which have an $R^1$ group, can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^1$ of the $N^2$-phosphinyl formamidine transition metal complexes, the $N^2$-phosphinyl amidine transition metal complexes, and/or the $N^2$-phosphinyl guanidine transition metal complexes, which have an $R^1$ group, can be an alkyl group; alternatively, a substituted alkyl group; alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, the alkyl group which can be utilized as $R^1$ can be a $C_1$ to $C_{20}$, a $C_1$ to $C_{10}$, or a $C_1$ to $C_5$ alkyl group. In any aspect or embodiment disclosed herein, the substituted alkyl group which can be utilized as $R^1$ can be a $C_1$ to $C_{20}$, a $C_1$ to $C_{10}$, or a $C_1$ to $C_5$ substituted alkyl group. In any aspect or embodiment disclosed herein, the cycloalkyl group which can be utilized as $R^1$ can be a $C_4$ to $C_{20}$, a $C_4$ to $C_{15}$, or a $C_4$ to $C_{10}$ cycloalkyl group. In any aspect or embodiment disclosed herein, the substituted cycloalkyl group which can be utilized as $R^1$ can be a $C_4$ to $C_{20}$, a $C_4$ to $C_{15}$, or a $C_4$ to $C_{10}$ substituted cycloalkyl group. In any aspect or embodiment disclosed herein, the aryl group which can be utilized as $R^1$ can be a $C_6$ to $C_{20}$, a $C_6$ to $C_{15}$, or a $C_6$ to $C_{10}$ aryl group. In any aspect or embodiment disclosed herein, the substituted aryl group which can be utilized as $R^1$ can be a $C_6$ to $C_{20}$, a $C_6$ to $C_{15}$, or a $C_6$ to $C_{10}$ substituted aryl group. In any aspect or embodiment disclosed herein, the aralkyl group which can be utilized as $R^1$ can be a $C_7$ to $C_{20}$, a $C_7$ to $C_{15}$, or a $C_7$ to $C_{10}$ aralkyl group. In any aspect or embodiment disclosed herein, the substituted aralkyl group which can be utilized as $R^1$ can be a $C_7$ to $C_{20}$ substituted aralkyl group; alternatively, a $C_7$ to $C_{15}$ substituted aralkyl group; or alternatively, a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarboxy groups, and substituent hydrocarboxy groups can be utilized without limitation to further describe $R^1$.

In an embodiment, $R^1$ can be a methyl group, an ethyl group, a propyl group, a butyl group, a pentyl group, a hexyl group, a heptyl group, or an octyl group. In some embodiments, $R^1$ can be a methyl group, an ethyl group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some embodiments, the alkyl groups which can be utilized as $R^1$ can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group (general or specific) which can be utilized as $R^1$.

In an embodiment, $R^1$ can be a cyclopentyl group, a substituted cyclopentyl group, a cyclohexyl group, or a substituted cyclohexyl group; alternatively, a cyclopentyl group or a substituted cyclopentyl group; alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an embodiment, the substituted cycloalkyl group, which can be utilized as $R^1$, can be a 2-substituted cyclohexyl group, a 2,6-disubstituted cyclohexyl group, a 2-substituted cyclopentyl group, or a 2,6-disubstituted cyclopentyl group; alternatively, a 2-substituted cyclohexyl group or a 2,6-disubstituted cyclohexyl group; alternatively, a 2-substituted cyclopentyl group or a 2,6-disubstituted cyclopentyl group; alternatively, a 2-substituted cyclohexyl group or a 2-substituted cyclopentyl group; alternatively, a 2,6-disubstituted cyclohexyl group or a 2,6-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,6-disubstituted cyclopentyl group. In an embodiment, one or more substituents of a multi-substituted cycloalkyl group utilized as $R^1$ can be the same or different; alternatively, all the substituents can be the same, or alternatively, all the substituents can be different. Each substituent of a substituted cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^1$.

In a non-limiting embodiment, $R^1$ can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, a 2,5-dialkylcyclopentyl group. Alkyl substituent groups (general and specific) are independently described herein and these alkyl substituent groups can be utilized, without limitation, to further describe alkylcyclohexyl (general and specific), dialkylcyclohexyl (general and specific), alkylcyclopentyl (general and specific), and/or dialkylcyclopentyl (general and specific) groups which can be utilized as $R^1$. Generally, the alkyl substituents of a disubstituted cyclohexyl or cyclopentyl group can be the same, or alternatively, the alkyl substituents can be different. In some non-limiting embodiments, $R^1$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting embodiments, $R^1$ can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an embodiment, $R^1$ can be a phenyl group or a substituted phenyl group; alternatively, a phenyl group; or alternatively, a substituted phenyl group. In an embodiment, the substituted phenyl group which can be utilized as $R^1$ can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an embodiment, one or more substituents of a multi-substituted phenyl group utilized as $R^1$ can be the same or different; alternatively, all the substituents can be the same, or alternatively, all the substituents can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy group can be utilized without limitation to further describe a substituted phenyl group (general or specific) which can be utilized as $R^1$.

In a non-limiting embodiment, $R^1$ can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^1$. Generally, the alkyl substituents of dialkylphenyl groups (general or specific) or trialkylphenyl groups (general or specific) can be the same, or alternatively, the alkyl substituents can be different. In some non-limiting embodiments, $R^1$ can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; or alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In an embodiment, $R^1$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl which can be utilized as $R^1$.

Generally, $R^2$ of the $N^2$-phosphinyl amidine transition metal compound complexes can be an organyl group; alternatively, an organyl group consisting essentially of inert functional groups; or alternatively, a hydrocarbyl group. In an embodiment, $R^2$ of the $N^2$-phosphinyl amidine transition metal complexes can be a $C_1$ to $C_{20}$, a $C_1$ to $C_{15}$, a $C_1$ to, or a $C_1$ to $C_5$ organyl group. In an embodiment, $R^2$ of the $N^2$-phosphinyl amidine transition metal compound complexes can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, $R^2$ of the $N^2$-phosphinyl amidine transition metal compound complexes can be a $C_1$ to $C_{20}$, a $C_1$ to $C_{15}$, a $C_1$ to $C_{10}$, or a $C_1$ to $C_5$ hydrocarbyl group.

In an embodiment, $R^2$ of the $N^2$-phosphinyl amidine transition metal compound complexes can be an alkyl group, a substituted alkyl group, a cycloalkyl group, a substituted cycloalkyl group, an aryl group, a substituted aryl group, an aralkyl group, or a substituted aralkyl group. In some embodiments, $R^2$ can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^2$ can be an alkyl group; alternatively, a substituted alkyl group; alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, $R^2$ can be a $C_1$ to $C_{20}$, a $C_1$ to $C_{10}$, or a $C_1$ to $C_5$ alkyl group. In any aspect or embodiment disclosed herein, the substituted alkyl group which can be utilized as $R^2$ can be a $C_1$ to $C_{20}$, a $C_1$ to $C_{10}$, or a $C_1$ to $C_5$ substituted alkyl group. In any aspect or embodiment disclosed herein, the cycloalkyl group which can be utilized as $R^2$ can be a $C_4$ to $C_{20}$, a $C_4$ to $C_{15}$, or a $C_4$ to $C_{10}$ cycloalkyl group. In any aspect or embodiment disclosed herein, the substituted cycloalkyl group which can be utilized as $R^2$ can be a $C_4$ to $C_{20}$, a $C_4$ to $C_{15}$, or a $C_4$ to $C_{10}$ substituted cycloalkyl group. In any aspect or embodiment disclosed herein, the aryl group which can be utilized as $R^2$ can be a $C_6$ to $C_{20}$, a $C_6$ to $C_{15}$, or a $C_6$ to $C_{10}$ aryl group. In any aspect or embodiment disclosed herein, the substituted aryl group which can be utilized as $R^2$ can be a $C_6$ to $C_{20}$, a $C_6$ to $C_{15}$, or a $C_6$ to $C_{10}$ substituted aryl group. In any aspect or embodiment disclosed herein, the aralkyl group which can be utilized as $R^2$ can be a $C_7$ to $C_{20}$, a $C_7$ to $C_{15}$, or a $C_7$ to $C_{10}$ aralkyl group. In any aspect or embodiment disclosed herein, the substituted aryl group which can be utilized as $R^2$ can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarboxy groups, and substituent hydrocarboxy groups can be utilized without limitation to further describe $R^2$.

In an embodiment, $R^2$ can be a methyl group, an ethyl group, a propyl group, a butyl group, a pentyl group, a hexyl group, a heptyl group, or an octyl group. In some embodiments, $R^2$ can be a methyl group, an ethyl group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some embodiments, the alkyl groups which can be utilized as $R^2$ can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as $R^2$.

In an embodiment, $R^2$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an embodiment, the substituted cycloalkyl group, which can be utilized as $R^2$, can be a 2-substituted cyclohexyl group, a 2,6-disubstituted cyclohexyl group, a 2-substituted cyclopentyl group, or a 2,6-disubstituted cyclopentyl group; alternatively, a 2-substituted cyclohexyl group or a 2,6-disubstituted cyclohexyl group; alternatively, a 2-substituted cyclopentyl group or a 2,6-disubstituted cyclopentyl group; alternatively, a 2-substituted cyclohexyl group or a 2-substituted cyclopentyl group; alternatively, a 2,6-disubstituted cyclohexyl group or a 2,6-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,6-disubstituted cyclopentyl group. In an embodiment, one or more substituents of a multi-substituted cycloalkyl group utilized as $R^2$ can be the same or different; alternatively, all the substituents of a multi-substituted cycloalkyl group can be the same; or alternatively, all the substituents of a multi-substituted cycloalkyl group can be different. Each substituent of a cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^2$.

In a non-limiting embodiment, $R^2$ can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^2$. Generally, the alkyl substituents of a disubstituted cyclohexyl or cyclopentyl group can be the same, or alternatively, the alkyl substituents can be different. In some non-limiting embodiments, $R^2$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting embodiments, $R^2$ can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an embodiment, $R^2$ can be a phenyl group or a substituted phenyl group; alternatively, a phenyl group; or alternatively, a substituted phenyl group. In an embodiment, the substituted phenyl group can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an embodiment, one or more substituents of a multi-substituted phenyl group utilized as $R^2$ can be the same or different; alternatively, all the substituents can be the same, or alternatively, all the substituents can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^2$.

In a non-limiting embodiment, $R^2$ can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^2$. Generally, the alkyl substituents of dialkylphenyl groups (general or specific) or trialkylphenyl groups (general or specific) can be the same, or alternatively, the alkyl substituents can be different. In some non-limiting embodiments, $R^2$ can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; or alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting embodiment, $R^2$ can be a phenyl group, a 2-alkoxyphenyl group, or a 4-alkoxyphenyl group. In some non-limiting embodiments, $R^2$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group.

In a non-limiting embodiment, $R^2$ can be a phenyl group, a 2-halophenyl group, a 4-halophenyl group, or a 2,6-dihalophenyl group. Generally, the halides of a dihalophenyl group can be the same, or alternatively, the halides can be different. In some embodiments, $R^2$ can be a phenyl group, a 2-fluorophenyl group, 4-fluorophenyl group, or a 2,6-difluorophenyl group.

In an embodiment, $R^2$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy group can be utilized without limitation to further describe a substituted benzyl which can be utilized as $R^2$.

Generally, $R^{2a}$ and/or $R^{2b}$ of the $N^2$-phosphinyl guanidine transition metal compound complexes which have an $R^{2a}$ and/or $R^{2b}$ group independently can be hydrogen or an organyl group; alternatively, hydrogen; or alternatively, an organyl group. In another aspect, $R^{2a}$ and/or $R^{2b}$ independently can be hydrogen or an organyl group consisting essentially of inert functional groups; alternatively, hydrogen; or alternatively, an organyl group consisting essentially of inert functional groups. In yet another aspect, $R^{2a}$ and/or $R^{2b}$ independently can be hydrogen or a hydrocarbyl group; alternatively, hydrogen; or alternatively, a hydrocarbyl group.

In an embodiment, the $R^{2a}$ and $R^{2b}$ organyl groups of the $N^2$-phosphinyl guanidine transition metal compound complexes, which have an $R^{2a}$ and/or $R^{2b}$ organyl group, independently can be a $C_1$ to $C_{20}$ organyl group; alternatively, a $C_1$ to $C_{15}$, a $C_1$ to $C_{10}$, or a $C_1$ to $C_5$ organyl group. In some embodiments, the $R^{2a}$ and/or $R^{2b}$ organyl groups consisting of inert functional group of the $N^2$-phosphinyl guanidine transition metal complexes, which have an $R^{2a}$ and/or $R^{2b}$ organyl consisting of inert functional groups, independently can be a $C_1$ to $C_{20}$, a $C_1$ to $C_{15}$, a $C_1$ to $C_{10}$, or a $C_1$ to $C_5$ organyl group consisting essentially of inert functional groups. In other embodiments, the $R^{2a}$ and/or $R^{2b}$ hydrocarbyl groups of the $N^2$-phosphinyl guanidine transition metal compound complexes, which have an $R^{2a}$ and/or $R^{2b}$ hydrocarbyl group, independently can be a $C_1$ to $C_{20}$, a $C_1$ to $C_{15}$, a $C_1$ to $C_{10}$, or a $C_1$ to $C_5$ hydrocarbyl group.

In an embodiment, $R^{2a}$ and $R^{2b}$ of the $N^2$-phosphinyl guanidine transition metal compound complexes independently can be an alkyl group, a substituted alkyl group, a cycloalkyl group, a substituted cycloalkyl group, an aryl group, a substituted aryl group, an aralkyl group, or a substituted aralkyl group. In some embodiments, $R^{2a}$ and $R^{2b}$ can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^{2a}$ and $R^{2b}$ independently can be an alkyl group; alternatively, a substituted alkyl group; alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, $R^{2a}$ and $R^{2b}$ independently can be $C_1$ to $C_{20}$, a $C_1$ to $C_{10}$, or a $C_1$ to $C_5$ alkyl group. In any aspect or embodiment disclosed herein, the cycloalkyl group which can be utilized as $R^{2a}$ and/or $R^{2b}$ independently can be a $C_4$ to $C_{20}$, a $C_4$ to $C_{15}$, or a $C_4$ to $C_{10}$ cycloalkyl group. In any aspect or embodiment disclosed herein, the substituted cycloalkyl group which can be utilized as $R^{2a}$ and/or $R^{2b}$ independently can be a $C_4$ to $C_{20}$, a $C_4$ to $C_{15}$, or a $C_4$ to $C_{10}$ substituted cycloalkyl group. In any aspect or embodiment disclosed herein, the aryl group which can be utilized as $R^{2a}$ and/or $R^{2b}$ independently can be a $C_6$ to $C_{20}$, a $C_6$ to $C_{15}$, or a $C_6$ to $C_{10}$ aryl group. In any aspect or embodiment disclosed herein, the substituted aryl group which can be utilized as $R^{2a}$ and/or $R^{2b}$ independently can be a $C_6$ to $C_{20}$, a $C_6$ to $C_{15}$, or a $C_6$ to $C_{10}$ substituted aryl group. Each substituent of a substituted cycloalkyl group (general or specific) and/or a substituted aryl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific)

are independently disclosed herein. These substituent halogens, substituent hydrocarboxy groups, and substituent hydrocarboxy groups can be utilized without limitation to further describe $R^{2a}$ and/or $R^{2b}$.

In an aspect, $R^1$ and $R^{2a}$ of the $N^2$-phosphinyl guanidine transition metal complexes can be joined to form a group, $L^{12}$, wherein $L^{12}$, the $N^1$ nitrogen atom, and the $N^3$ nitrogen atom can form a ring or a ring system. In another aspect, $R^3$ and $R^{2b}$ of the $N^2$-phosphinyl guanidine transition metal compound complexes can be joined to form a group, $L^{23}$, wherein $L^{23}$, the $N^2$ nitrogen atom, and the $N^3$ nitrogen atom can form a ring or a ring system. In an embodiment, $L^{12}$ and/or $L^{23}$ independently can be an organylene group; alternatively, an organylene group consisting of inert functional groups; or alternatively, a hydrocarbylene group. The organylene group which can be utilized as $L^{12}$ and/or $L^{23}$ independently can be a $C_2$ to $C_{20}$, a $C_2$ to $C_{15}$, a $C_2$ to $C_{10}$, or a $C_2$ to $C_5$ organylene group. The organylene group consisting of inert functional groups which can be utilized as $L^{12}$ and/or $L^{23}$ independently can be a $C_2$ to $C_{20}$, a $C_2$ to $C_{15}$, a $C_2$ to $C_{10}$, or a $C_2$ to $C_5$ organylene group consisting of inert functional groups. The hydrocarbylene group which can be utilized as $L^{12}$ and/or $L^{23}$ independently can be a $C_2$ to $C_{20}$, a $C_2$ to $C_{15}$, a $C_2$ to $C_{10}$, or a $C_2$ to $C_5$ hydrocarbylene group.

In an embodiment, $L^{12}$ and/or $L^{23}$ can have any structure provided in Table 1. In some embodiments, $L^{12}$ and/or $L^{23}$ can have Structure 1L, Structure 2L, Structure 3L, Structure 4L, or Structure 5L. In some embodiments, $L^{12}$ and/or $L^{23}$ can have Structure 2L or Structure 3L; alternatively, Structure 4L or Structure 5L. In other embodiments, $L^{12}$ and/or $L^{23}$ can have Structure 1L; alternatively, Structure 2L; alternatively, Structure 3L; alternatively, Structure 4L; or alternatively, Structure 5L. In some embodiments, $L^{12}$ and/or $L^{23}$ can have Structure 6L. It should be noted that when $L^{12}$ has Structure 6L, the corresponding $R^{2b}$ is null because of the double bond link (depicted as real but can be delocalized through aromatic resonance) with the $N^3$ nitrogen atom of the $N^2$-phosphinyl guanidine metal complex.

$R^{L27}$, $R^{L28}$, and $R^{L29}$ of the linking group having Structure 6L independently can be a hydrogen or a non-hydrogen substituent group; or alternatively, hydrogen. Non-hydrogen substituent groups (general and specific) are independently disclosed herein and can be utilized without limitation to further describe the linking group having Structure 1L, Structure 2L, Structure 3L, Structure 4L, and/or Structure 5L. In an embodiment, $L^{12}$ and/or $L^{23}$ can be an eth-1,2-ylene group (—CH$_2$CH$_2$—), an ethen-1,2-ylene group (—CH═CH—), a prop-1,3-ylene group (—CH$_2$CH$_2$CH$_2$—), a 1-methylethen-1,2-ylene group (—C(CH$_3$)═CH—), a but-1,3-ylene group (—CH$_2$CH$_2$CH(CH$_3$)—), a 3-methylbut-1,3-ylene group (—CH$_2$CH$_2$C(CH$_3$)$_2$—), or a phen-1,2-ylene group. In some non-limiting embodiments, $L^{12}$ and/or $L^{23}$ be an eth-1,2-ylene group (—CH$_2$CH$_2$—), a prop-1,3-ylene group (—CH$_2$CH$_2$CH$_2$—), a 1-methylethen-1,2-ylene group (—C(CH$_3$)═CH—), a but-1,3-ylene group (—CH$_2$CH$_2$CH(CH$_3$)—), or a 3-methylbut-1,3-ylene group (—CH$_2$CH$_2$C(CH$_3$)$_2$—); alternatively, an eth-1,2-ylene group (—CH$_2$CH$_2$—), an ethen-1,2-ylene group (—CH═CH—), a prop-1,3-ylene group (—CH$_2$CH$_2$CH$_2$—), or a phen-1,2-ylene group; alternatively, an eth-1,2-ylene group (—CH$_2$CH$_2$—) or a prop-1,3-ylene group (—CH$_2$CH$_2$CH$_2$—); alternatively, an ethen-1,2-ylene group (—CH═CH—) or a phen-1,2-ylene group. In other embodiments, $L^{12}$ and/or $L^{23}$ can be an eth-1,2-ylene group (—CH$_2$CH$_2$—); alternatively, an ethen-1,2-ylene group (—CH═CH—); alternatively, a prop-1,3-ylene group (—CH$_2$CH$_2$CH$_2$—); alternatively, a 1-methylethen-1,2-ylene group (—C(CH$_3$)═CH—); alternatively, a but-,3-ylene group (—CH$_2$CH$_2$CH(CH$_3$)—); alternatively, a 3-methylbut-1,3-ylene group (—CH$_2$CH$_2$C(CH$_3$)$_2$—); or alternatively, a phen-1,2-ylene group. In some embodiments, $L^{12}$ and/or $L^{23}$ can be a —CH═CH—CH═group.

In an embodiment, $L^{12}$ can have a structure that can comprise at least one substituent located on the carbon atom attached to the $N^1$ nitrogen atom of the $N^2$-phosphinyl guanidine transition metal compound complex; alterna-

TABLE 1

Structures for Linking Groups $L^{12}$ and/or $L^{23}$.

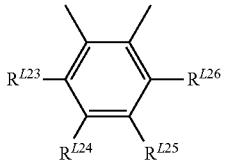

| —(CR$^{L1}$R$^{L2}$)$_m$— | —CR$^{L3}$R$^{L4}$  CR$^{L5}$R$^{L6}$$_m$— | —CR$^{L3}$R$^{L4}$  CR$^{L7}$R$^{L8}$  CR$^{L5}$R$^{L6}$— |
| --- | --- | --- |
| Structure 1L | Structure 2L | Structure 3L |
| —CR$^{1L}$═CR$^{12L}$— | | ═CR$^{L27}$—CR$^{L28}$═CR$^{L29}$— |
| Structure 4L | Structure 5L | Structure 6L |

Within the structures of Table 1, the undesignated valencies represent the points at which $L^{12}$ and/or $L^{23}$, when present, attach to the respective nitrogen atoms of the $N^2$-phosphinyl guanidine transition metal compound complex. Generally, m can be an integer ranging from 2 to 5. In further embodiments, m can be 2 or 3; alternatively, m can be 2; or alternatively, m can be 3. $R^{L1}$ and $R^{L2}$ of the linking group having Structure 1L, $R^{L3}$, $R^{L4}$, $R^{L5}$, and $R^{L6}$ of the linking group having Structure 2L, $R^{L3}$, $R^{L4}$, $R^{L5}$, $R^{L6}$, $R^{L7}$, and $R^{L8}$ of the linking group having Structure 3L, $R^{L11}$ and $R^{L12}$ of the linking group having Structure 4L, $R^{L23}$, $R^{L24}$, $R^{L25}$, and $R^{L26}$ of the linking group having Structure 5L, and tively, can comprise only one substituent located on the carbon atom attached to the $N^1$ nitrogen atom of the $N^2$-phosphinyl guanidine transition metal compound complex; or alternatively, can comprise two substituents located on the carbon atom attached to the $N^1$ nitrogen atom of the $N^2$-phosphinyl guanidine transition metal compound complex. In another embodiment, $L^{12}$ can have a structure that can consist of one substituent located on the carbon atom attached to the $N^1$ nitrogen atom of the $N^2$-phosphinyl guanidine transition metal compound complex; or alternatively, can consist of two substituents located on the carbon atom attached to the $N^1$ nitrogen atom of the $N^2$-phosphinyl guanidine transition metal compound complex.

In an embodiment, $R^{2a}$ and $R^{2b}$ of the $N^2$-phosphinyl guanidine transition metal compound complexes can be joined to form a group, $L^{22}$, wherein $R^{2a}$, $R^{2b}$, and the $N^3$ nitrogen (or $L^{22}$ and the $N^3$ nitrogen) form a ring or ring system. In an embodiment, $L^{22}$ of the $N^2$-phosphinyl guanidine transition metal compound complexes having an $L^{22}$ group can be an organylene group; alternatively, an organylene group consisting of inert functional groups; or alternatively, a hydrocarbylene group. The organylene group which can be utilized as $L^{22}$ can be a $C_3$ to $C_{20}$, a $C_3$ to $C_{15}$, or a $C_3$ to $C_{10}$ organylene group. The organylene group consisting of inert functional groups which can be utilized as $L^{22}$ can be a $C_3$ to $C_{20}$, a $C_3$ to $C_{15}$, or a $C_3$ to $C_{10}$ organylene group consisting of inert functional groups. The hydrocarbylene group which can be utilized as $L^{22}$ can be a $C_4$ to $C_{20}$, a $C_4$ to $C_{15}$, or a $C_4$ to $C_{10}$ hydrocarbylene group.

In an embodiment, $L^{22}$ can have any structure provided in Table 2. In some embodiments, $L^{22}$ can have Structure 11L, Structure 12L, Structure 13L, Structure 14L, or Structure 15L. In other embodiments, $L^{22}$ can have Structure 11L; alternatively, Structure 12L; alternatively, Structure 13L; alternatively, Structure 14L; or alternatively, Structure 15L.

TABLE 2

Structures for Linking Group $L^{22}$.

$—(CR^{L31}R^{L32})_n—$
Structure 11L
$—CR^{L41}R^{L42}—CR^{L45}R^{L46}\ CR^{L47}R^{L48}\ CR^{L43}R^{L44}—$
Structure 12L
$—CR^{L41}R^{L42}—CR^{L45}R^{L46}—CR^{L49}R^{L50}—CR^{L47}R^{L48}—CR^{L43}R^{L44}—$
Structure 13L
$—CR^{L41}R^{L42}—CR^{L45}R^{L46}—O—CR^{L47}R^{L48}—CR^{L43}R^{L44}—$
Structure 14L
$—CR^{L51}=CR^{L53}—CR^{L54}=CR^{L52}—$
Structure 15L Within the structures of Table 2, the undesignated valencies represent the points at which $L^{22}$ of the $N^2$-phosphinyl guanidine transition metal compound complexes, when present, attach to the $N^3$ nitrogen atom of the $N^2$-phosphinyl guanidine transition metal compound complex. Generally, n can be an integer ranging from 4 to 7. In further embodiments, n can be 4 or 5; alternatively, n can be 4; or alternatively, n can be 5. $R^{L31}$ and $R^{L32}$ of the linking group having Structure 11L, $R^{L41}$, $R^{L42}$, $R^{L43}$, $R^{L44}$, $R^{L45}$, $R^{L46}$, $R^{L47}$, and $R^{L48}$ of the linking group having Structure 12L, $R^{L41}$, $R^{L42}$, $R^{L43}$, $R^{L44}$, $R^{L45}$, $R^{L46}$, $R^{L47}$, $R^{L48}$, $R^{L49}$, and $R^{L50}$ of the linking group having Structure 13L, $R^{L41}$, $R^{L42}$, $R^{L43}$, $R^{L44}$, $R^{L45}$, $R^{L46}$, $R^{L47}$, and $R^{L48}$ of the linking group having Structure 14L, and $R^{L41}$, $R^{L42}$, $R^{L43}$, $R^{L44}$, $R^{L45}$, $R^{L46}$, $R^{L47}$, and $R^{L48}$ of the linking group having Structure 15L, independently can be a hydrogen or a non-hydrogen substituent group; or alternatively, hydrogen. Non-hydrogen substituent groups (general and specific) are independently disclosed herein and can be utilized without limitation to further describe the linking group having Structure 11L, Structure 12L, Structure 13L, Structure 14L, and/or Structure 15L. In an embodiment, $L^{22}$ can be a but-1,4-ylene group, a pent-1,4-ylene group, a pent-1,5-ylene group, a hex-2,5-ylene group, a hex-1,5-ylene group, a hept-2,5-ylene group, a buta-1,3-dien-1,4-ylene group, or a bis(eth-2-yl)ether group; alternatively, a but-1,4-ylene group, a pent-1,5-ylene group, or a bis(eth-2-yl)ether group; alternatively, a but-1,4-ylene group; alternatively, a pent-1,5-ylene group; alternatively, a buta-1,3-dien-1,4-ylene group; or alternatively, a bis(eth-2-yl)ether group.

Generally, $R^3$ of the $N^2$-phosphinyl formamidine transition metal compound complexes, the $N^2$-phosphinyl amidine transition metal compound complexes, and/or the $N^2$-phosphinyl guanidine transition metal compound complexes which have an $R^3$ group can be hydrogen or an organyl group; alternatively, hydrogen or an organyl group consisting essentially of inert functional groups; alternatively, hydrogen or a hydrocarbyl group; alternatively, hydrogen; alternatively, an organyl group; alternatively, an organyl group consisting essentially of inert functional groups; or alternatively, a hydrocarbyl group. In an embodiment, the organyl group which can utilized as $R^3$ can be a $C_1$ to $C_{30}$, a $C_1$ to $C_{20}$, a $C_1$ to $C_{15}$, a $C_1$ to $C_{10}$, or a $C_1$ to $C_5$ organyl group. In an embodiment, the organyl group consisting of inert functional groups which can utilized as $R^3$ can be a $C_1$ to $C_{30}$, a $C_1$ to $C_{20}$, a $C_1$ to $C_{15}$, a $C_1$ to $C_{10}$, or a $C_1$ to $C_5$ organyl group consisting essentially of inert functional groups. In an embodiment, the hydrocarbyl group which can utilized as $R^3$ can be a $C_1$ to $C_{30}$, a $C_1$ to $C_{20}$, a $C_1$ to $C_{15}$, a $C_1$ to $C_{10}$, or a $C_1$ to $C_5$ hydrocarbyl group. In other embodiments, $R^3$ can be a $C_1$ to $C_{30}$, a $C_1$ to $C_{20}$, a $C_1$ to $C_{15}$, a $C_1$ to $C_{10}$, or a $C_1$ to $C_5$ alkyl group. In yet other embodiments, $R^3$ can be a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. Substituent groups (general and specific) are provided herein and these general substituent groups can be utilized to further describe the substituted phenyl groups which can be utilized as $R^3$.

Generally, $R^4$ and/or $R^5$ of the $N^2$-phosphinyl formamidine transition metal compound complexes, the $N^2$-phosphinyl amidine transition metal compound complexes, and/or the $N^2$-phosphinyl guanidine transition metal compound complexes independently can be an organyl group; alternatively, an organyl group consisting essentially of inert functional groups; or alternatively, a hydrocarbyl group. In an embodiment, the $R^4$ and/or $R^5$ organyl groups independently can be a $C_1$ to $C_{20}$, a $C_1$ to $C_{15}$, a $C_1$ to $C_{10}$, or a $C_1$ to $C_5$ organyl group. In an embodiment, the $R^4$ and/or $R^5$ organyl group consisting essentially of inert functional groups independently can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, the $R^4$ and/or $R^5$ hydrocarbyl groups independently can be a $C_1$ to $C_{30}$ hydrocarbyl group; alternatively, a $C_1$ to $C_{20}$, a $C_1$ to $C_{15}$, a $C_1$ to $C_{10}$, or a $C_1$ to $C_5$ hydrocarbyl group. In further embodiments, $R^4$ and/or $R^5$ can be joined to form a ring or a ring system.

In an embodiment, $R^4$ and/or $R^5$ of the $N^2$-phosphinyl formamidine transition metal compound complexes, the $N^2$-phosphinyl amidine transition metal compound complexes, and/or the $N^2$-phosphinyl guanidine transition metal compound complexes independently can be an alkyl group, a substituted alkyl group, a cycloalkyl group, a substituted cycloalkyl group, an aryl group, a substituted aryl group, an aralkyl group, or a substituted aralkyl group. In some embodiments, $R^4$ and/or $R^5$ independently can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^4$ and/or $R^5$ independently can be an alkyl group; alternatively, a substituted alkyl group; alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, each alkyl group which can be utilized as $R^4$ and $R^5$ independently can be a $C_1$ to $C_{20}$, a $C_1$ to $C_{10}$, or a $C_1$ to $C_5$ alkyl group. In any aspect or embodiment disclosed herein, each substituted alkyl group which can be utilized as $R^4$ and $R^5$ independently can be a $C_1$ to $C_{20}$, a $C_1$ to $C_{10}$, or a $C_1$ to $C_5$ substituted alkyl group. In any aspect or embodiment disclosed herein, each cycloalkyl group which can be utilized as $R^4$ and $R^5$ independently can be a $C_4$ to $C_{20}$, a $C_4$ to $C_{15}$, or a $C_4$ to $C_{10}$ cycloalkyl group. In any aspect or embodiment disclosed herein, each substituted cycloalkyl group which can be utilized as $R^4$ and $R^5$ independently can be a $C_4$ to $C_{20}$, a $C_4$ to $C_{15}$, or a $C_4$ to $C_{10}$ substituted cycloalkyl group. In any aspect or embodiment disclosed herein, each aryl group which can be utilized as $R^4$ and $R^5$ independently can be a $C_6$ to $C_{20}$, a $C_6$ to $C_{15}$, or a $C_6$ to $C_{10}$ aryl group. In any aspect or embodiment disclosed herein, each substituted aryl group which can be utilized as $R^4$ and $R^5$ independently can be a $C_6$ to $C_{20}$, a $C_6$ to $C_{15}$, or a $C_6$ to $C_{10}$ substituted aryl group. In any aspect or embodiment disclosed herein, each aralkyl group which can be utilized $R^4$ and $R^5$ independently can be a $C_7$ to $C_{20}$, a $C_7$ to $C_{15}$, or a $C_7$ to $C_{10}$ aralkyl group. In any aspect or embodiment disclosed herein, each substituted aryl group which can be utilized as $R^4$ and $R^5$ independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^4$ and/or $R^5$.

In an embodiment, $R^4$ and $R^5$ independently can be a methyl group, an ethyl group, a propyl group, a butyl group, a pentyl group, a hexyl group, a heptyl group, or an octyl group. In some embodiments, $R^4$ and $R^5$ independently can be a methyl group, an ethyl group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some embodiments, the alkyl groups which can be utilized as $R^4$ and $R^5$ can be substituted. Each substituent of a substituted alkyl group independently can be a halogen or a hydrocarboxy group; alternatively, a halogen; or alternatively, a hydrocarboxy group. Substituent halogens and substituent hydrocarboxy groups are independently disclosed herein. These substituent halogens and substituent hydrocarboxy groups (general and specific) can be utilized without limitation to further describe a substituted alkyl group which can be utilized as $R^4$ and/or $R^5$ independently.

In an embodiment, $R^4$ and $R^5$ independently can be a cyclopentyl group, a substituted cyclopentyl group, a cyclohexyl group, or a substituted cyclohexyl group; alternatively, a cyclopentyl group or a substituted cyclopentyl group; alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an embodiment, the substituted cycloalkyl group which can be utilized for $R^4$ and $R^5$ can be a 2-substituted cyclohexyl group, a 2,6-disubstituted cyclohexyl group, a 2-substituted cyclopentyl group, or a 2,6-disubstituted cyclopentyl group; alternatively, a 2-substituted cyclohexyl group or a 2,6-disubstituted cyclohexyl group; alternatively, a 2-substituted cyclopentyl group or a 2,6-disubstituted cyclopentyl group; alternatively, a 2-substituted cyclohexyl group or a 2-substituted cyclopentyl group; alternatively, a 2,6-disubstituted cyclohexyl group or a 2,6-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,6-disubstituted cyclopentyl group. In an embodiment, one or more substituents of a multi-substituted cycloalkyl group utilized as $R^4$ and $R^5$ can be the same or different; alternatively, all the substituents can be the same, or alternatively, all the substituents can be different. Each substituent of a cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^4$ and/or $R^5$.

In a non-limiting embodiment, $R^4$ and $R^5$ independently can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^4$ and $R^5$. Generally, the alkyl substituents of a disubstituted cyclohexyl or cyclopentyl group can be the same, or alternatively, the alkyl substituents can be different. In some non-limiting embodiments, $R^4$ and $R^5$ independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting embodiments, $R^4$ and $R^5$ independently can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an embodiment, $R^4$ and $R^5$ independently can be a phenyl group or a substituted phenyl group; alternatively, a phenyl group; or alternatively, a substituted phenyl group. In an embodiment, the substituted phenyl group which can be utilized for $R^4$ and $R^5$ can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an embodiment, one or more substituents of a multi-substituted phenyl group utilized as $R^4$ and $R^5$ can be the same or different; alternatively, all the substituents can be the same, or alternatively, all the substituents can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^4$ and/or $R^5$.

In a non-limiting embodiment, $R^4$ and $R^5$ independently can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^4$ and $R^5$. Generally, the alkyl substituents of dialkylphenyl groups (general or specific) or trialkylphenyl groups (general or specific) can be the same, or alternatively, the alkyl substituents can be different. In some non-limiting embodiments, $R^4$ and $R^5$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; or alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting embodiment, $R^4$ and/or $R^5$ can be a phenyl group, a 2-alkoxyphenyl group, or a 4-alkoxyphenyl group. In some non-limiting embodiments, $R^4$ and/or $R^5$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group.

In a non-limiting embodiment, $R^4$ and $R^5$ independently can be a phenyl group, a 2-halophenyl group, a 4-halophenyl group, or a 2,6-dihalophenyl group. Generally, the halides of a dihalophenyl group can be the same, or alternatively, the halides can be different. In some embodiments, $R^4$ and $R^5$ independently can be a phenyl group, a 2-fluorophenyl group, a 4-fluorophenyl group, or a 2,6-difluorophenyl group.

In an embodiment, $R^4$ and $R^5$ independently can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general or specific), and substituent hydrocarboxy groups (general or specific) are independently disclosed herein. These substituent halogens, substituent hydrocarbyl groups, and substituent hydrocarboxy groups can be utilized without limitation to further describe a substituted benzyl which can be utilized as $R^4$ and/or $R^5$.

Generally, the neutral ligand, Q, of the $N^2$-phosphinyl formamidine transition metal compound complexes, the $N^2$-phosphinyl amidine transition metal compound complexes, and/or the $N^2$-phosphinyl guanidine transition metal compound complexes, if present, independently can be any neutral ligand that forms an isolatable compound with the $N^2$-phosphinyl formamidine transition metal compound complex, the $N^2$-phosphinyl amidine transition metal compound complex, and/or the $N^2$-phosphinyl guanidine transition metal compound complex. In an aspect, each neutral ligand independently can be a nitrile or an ether; alternatively, a nitrile; or alternatively, an ether. The number of neutral ligands, q, can be any number that forms an isolatable compound with the $N^2$-phosphinyl formamidine transition metal compound complexes, the $N^2$-phosphinyl amidine transition metal compound complexes, and/or the N²-phosphinyl guanidine transition metal compound complexes. In an aspect, the number of neutral ligands can be from 0 to 6; alternatively, from 0 to 3; alternatively, 0; alternatively, 1; alternatively, 2; alternatively, 3; or alternatively, 4.

Generally, each nitrile ligand independently can be a $C_2$ to $C_{20}$ or a $C_2$ to $C_{10}$ nitrile. In an embodiment, each nitrile ligand independently can be a $C_2$ to $C_{20}$ aliphatic nitrile, a $C_7$ to $C_{20}$ aromatic nitrile, a $C_8$ to $C_{20}$ aralkane nitrile, or any combination thereof; alternatively, a $C_2$ to $C_{20}$ aliphatic nitrile; alternatively, a $C_7$ to $C_{20}$ aromatic nitrile; or alternatively, a $C_8$ to $C_{20}$ aralkane nitrile. In some embodiments, each nitrile ligand independently can be a $C_2$ to $C_{10}$ aliphatic nitrile, a $C_7$ to $C_{10}$, aromatic nitrile, a $C_8$ to $C_{10}$ aralkane nitrile, or any combination thereof; alternatively, a $C_1$ to $C_{10}$ aliphatic nitrile; alternatively, a $C_7$ to $C_{10}$ aromatic nitrile; or alternatively, a $C_8$ to $C_{10}$ aralkane nitrile. In an embodiment, each aliphatic nitrile independently can be acetonitrile, propionitrile, a butyronitrile, benzonitrile, or any combination thereof; alternatively, acetonitrile; alternatively, propionitrile; alternatively, a butyronitrile; or alternatively, benzonitrile.

Generally, each ether ligand independently can be a $C_2$ to $C_{40}$, a $C_2$ to $C_{30}$, or a $C_2$ to $C_{20}$ ether. In an embodiment, each ether ligand independently can be a $C_2$ to $C_{40}$ aliphatic ether, a $C_3$ to $C_{40}$ aliphatic cyclic ether, a $C_4$ to $C_{40}$ aromatic cyclic ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; or alternatively, a $C_4$ to $C_{40}$ aromatic cyclic ether. In some embodiments, each ether ligand independently can be a $C_2$ to $C_{30}$ aliphatic ether, a $C_3$ to $C_{30}$ aliphatic cyclic ether, a $C_4$ to $C_{30}$ aromatic cyclic ether; alternatively, a $C_2$ to $C_{30}$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other embodiments, each ether ligand independently can be a $C_2$ to $C_{20}$ aliphatic ether, a $C_3$ to $C_{20}$ aliphatic cyclic ether, or a $C_4$ to $C_{20}$ aromatic cyclic ether; alternatively, a $C_2$ to $C_{20}$ aliphatic acyclic ether or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In some embodiments, each ether ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, isobenzofuran, dibenzofuran, diphenyl ether, a ditolyl ether, or any combination thereof; alternatively, dimethyl ether, diethyl ether, a dipropyl ether, a dibutyl ether, methyl ethyl ether, a methyl propyl ether, a methyl butyl ether, or any combination thereof; alternatively, tetrahydrofuran, a dihydrofuran, 1,3-dioxolane, tetrahydropyran, a dihydropyran, a pyran, a dioxane, or any combination thereof; alternatively, furan, benzofuran, isobenzofuran, isobenzofuran, dibenzofuran, or any combination thereof; alternatively, diphenyl ether, a ditolyl ether, or any combination thereof; alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, isobenzofuran; alternatively, dibenzofuran; alternatively, diphenyl ether; or alternatively, a ditolyl ether.

In some particular embodiments, the heteroatomic ligand transition metal compound complex can comprise, can consist essentially of, or can be, an N²-phosphinyl formamidine chromium compound complex having the Structure NPFCr1, an N²-phosphinyl amidine chromium compound complex having the Structure NPACr1, or an N²-phosphinyl guanidine chromium compound complex having the Structure GuCr1, GuCr2, GuCr3, GuCr4, or GuCr5; alternatively, an N²-phosphinyl formamidine chromium compound complex having the Structure NPFCr1; alternatively, an N²-phosphinyl amidine chromium compound complex having the Structure NPACr1; or alternatively, an N²-phosphinyl guanidine chromium compound complex having the Structure GuCr1, GuCr2, GuCr3, GuCr4, or GuCr5; alternatively, an N²-phosphinyl guanidine chromium compound complex having the Structure GuCr1; alternatively, an N²-phosphinyl guanidine chromium compound complex having the Structure GuCr2; alternatively, an N²-phosphinyl guanidine chromium compound complex having the Structure GuCr3; alternatively, an N²-phosphinyl guanidine chromium compound complex having the Structure GuCr4; or alternatively, an N²-phosphinyl guanidine chromium compound complex having the Structure GuCr5.

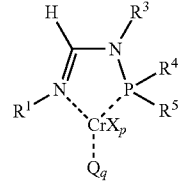

Structure NPFCr1

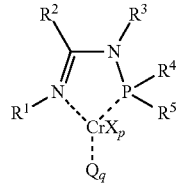

Structure NPACr1

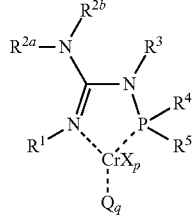

Structure GuCr1

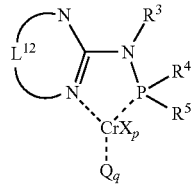

Structure GuCr2

-continued

Structure GuCr3

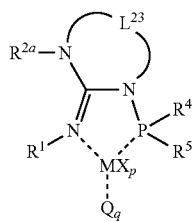

Structure GuCr4

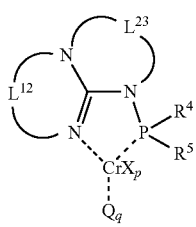

Structure GuCr5

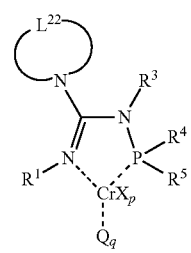

Generally, $R^1$, $R^2$, $R^{2a}$, $R^{2b}$, $R^3$, $R^4$, $R^5$, $L^{12}$, $L^{23}$, $L^{23}$, X, p, Q, and q for the $N^2$-phosphinyl formamidine chromium compound complexes, $N^2$-phosphinyl amidine chromium compound complexes, and $N^2$-phosphinyl guanidine chromium compound complexes can be any group disclosed herein for the respective $N^2$-phosphinyl formamidine transition metal compound complexes, $N^2$-phosphinyl amidine transition metal compound complexes, and $N^2$-phosphinyl guanidine transition metal compound complexes.

In a non-limiting embodiment, the $N^2$-phosphinyl formamidine chromium compound complex can be any one or more of NPFCr I, NPFCr II, NPFCrR III, NPFCr IV, NPFCr V, and NPFCr VI. In a non-limiting embodiment, the $N^2$-phosphinyl amidine chromium compound complex can be any one or more of NPACR I, NPACR II, NPACr III, NPACr IV, NPACr V, NPACr VI, NPACr VII, NPACr VIII, NPACr IX, NPACr X, NPACr XI, and NPACr XII. In a non-limiting embodiment, the $N^2$-phosphinyl guanidine chromium compound complex can be any one or more of GuFCr I, GuCr II, GuCr III, GuCr IV, GuCr V, and GuCr VI.

NPFCr I

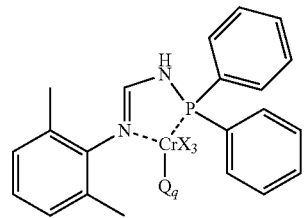

NPFCr II

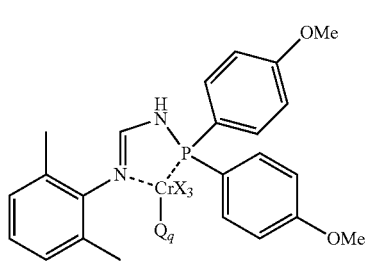

NPFCr III

NPFCr IV

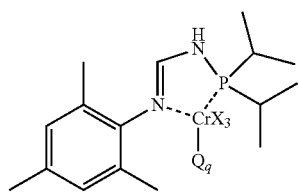

NPFCr V

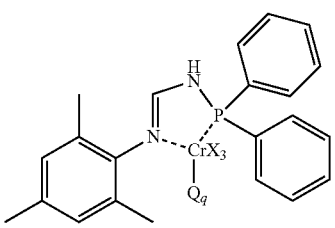

NPFCr VI

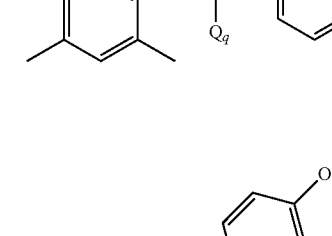

NPACr I

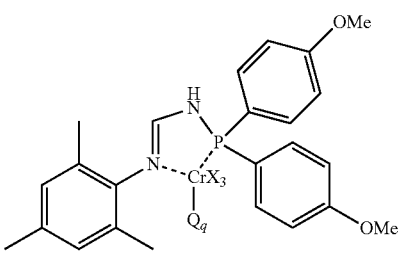

NPACr II
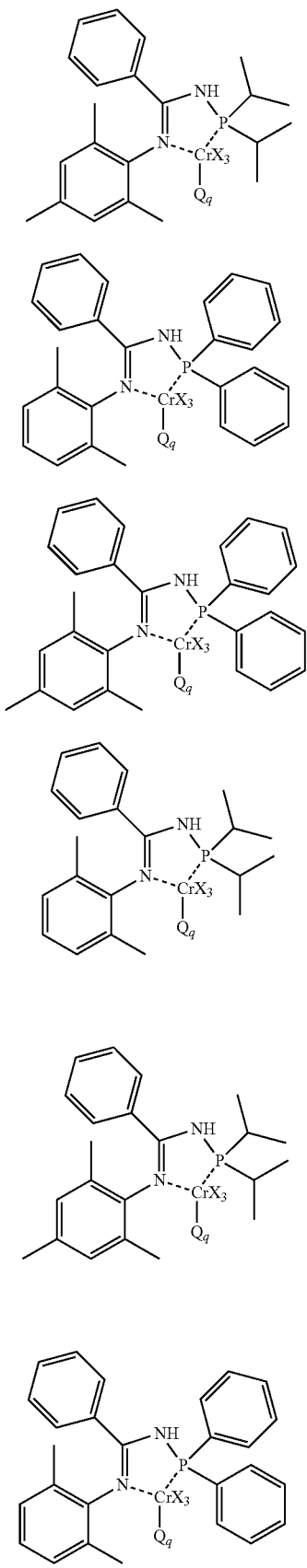
NPACr III
NPACr IV
NPACr V
NPACr VI
NPACr VII
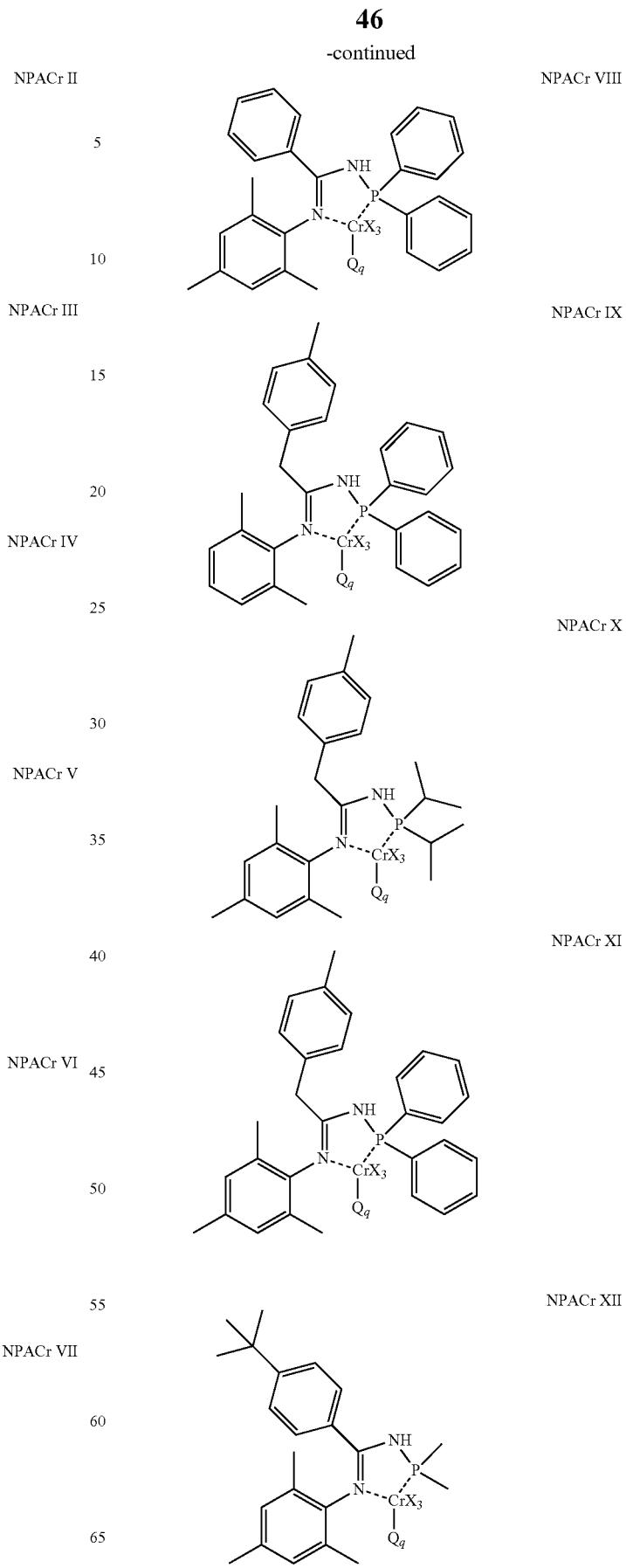
NPACr VIII
NPACr IX
NPACr X
NPACr XI
NPACr XII

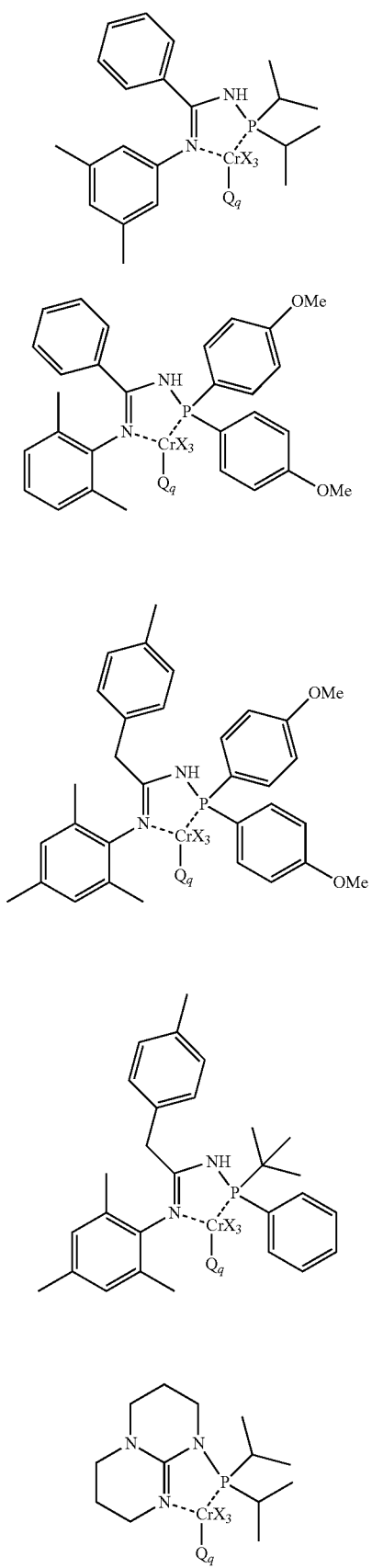

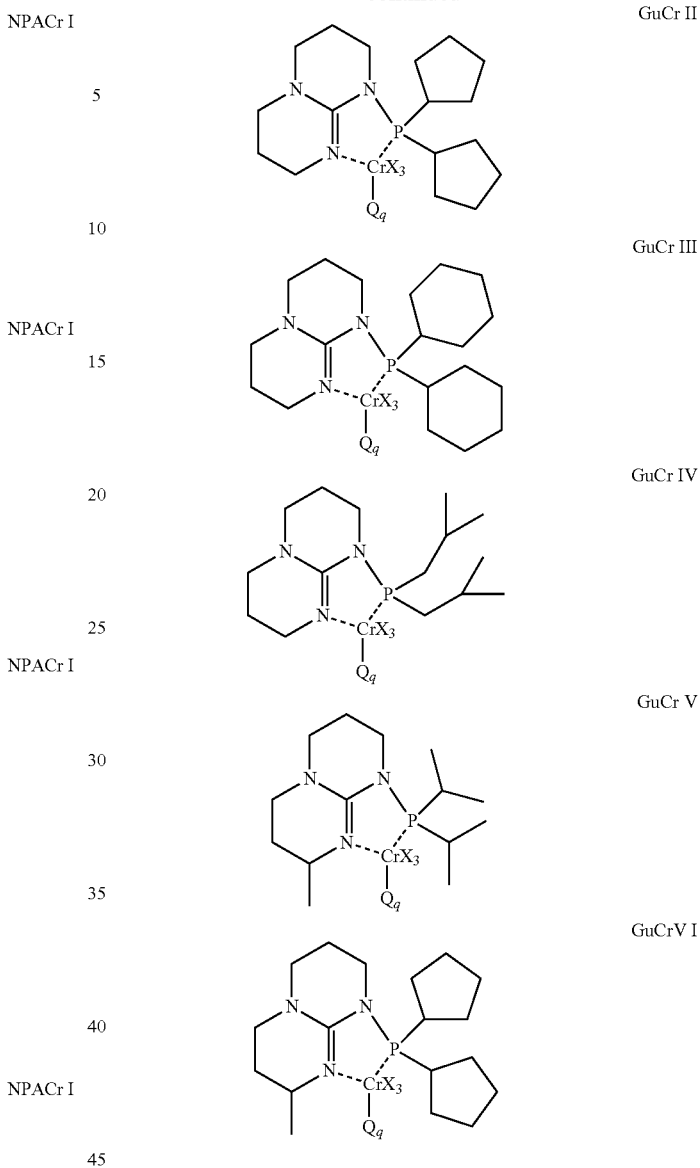

In a non-limiting embodiments, the chromium compound, $CrX_3$, of any of NPFCr I, NPFCr II, NPFCrR III, NPFCr IV, NPFCr V, NPFCr VI, NPACR I, NPACR II, NPACr III, NPACr IV, NPACr V, NPACr VI, NPACr VII, NPACr VIII, NPACr IX, NPACr X, NPACr XI, NPACr XII, GuFCr I, GuCr II, GuCr III, GuCr IV, GuCr V, and GuCr VI can be chromium(III) chloride or chromium(III) acetylacetonate; alternatively, chromium(III) chloride; or alternatively, chromium(III) acetylacetonate.

Chemically-Treated Solid Oxides

In the catalyst systems and oligomerization processes disclosed herein, any suitable chemically-treated solid oxide can be employed, whether one chemically-treated solid oxide or a mixture or combination of two or more different chemically-treated solid oxides. In one embodiment, the chemically-treated solid oxide can comprise a solid oxide treated with an electron-withdrawing anion. Alternatively, in another embodiment, the chemically-treated solid oxide can comprise a solid oxide treated with an electron-withdrawing anion, the solid oxide containing a Lewis-acidic metal ion. Non-limiting examples of suitable chemically-treated solid oxides are disclosed in, for instance, U.S. Pat. Nos. 7,294,599, 7,601,665, 7,884,163, 8,309,485, 8,623,973, 8,703,886, and 9,023,959.

The solid oxide can encompass oxide materials such as alumina, "mixed oxides" thereof such as silica-alumina, coatings of one oxide on another, and combinations and mixtures thereof. The mixed oxides such as silica-alumina can be single or multiple chemical phases with more than one metal combined with oxygen to form the solid oxide. Examples of mixed oxides that can be used to form a chemically-treated solid oxide, either singly or in combination, can include, but are not limited to, silica-alumina, silica-titania, silica-zirconia, alumina-titania, alumina-zirconia, zinc-aluminate, alumina-boria, silica-boria, aluminophosphate-silica, and titania-zirconia. The solid oxide used herein also can encompass oxide materials such as silica-coated alumina, as described in U.S. Pat. No. 7,884,163 (e.g., Sasol Siral® 28, Sasol Siral® 40, etc.)

Accordingly, in one embodiment, the solid oxide can comprise silica, alumina, silica-alumina, silica-coated alumina, aluminum phosphate, aluminophosphate, heteropolytungstate, titania, silica-titania, zirconia, silica-zirconia, magnesia, boria, zinc oxide, any mixed oxide thereof, or any combination thereof. In another embodiment, the solid oxide can comprise alumina, silica-alumina, silica-coated alumina, aluminum phosphate, aluminophosphate, heteropolytungstate, titania, silica-titania, zirconia, silica-zirconia, magnesia, boria, or zinc oxide, as well as any mixed oxide thereof, or any mixture thereof. The solid oxides contemplated herein can have any suitable surface area, pore volume, and particle size, as would be recognized by those of skill in the art. In another embodiment, the solid oxide can comprise silica, alumina, titania, zirconia, magnesia, boria, zinc oxide, any mixed oxide thereof, or any combination thereof. In yet another embodiment, the solid oxide can comprise silica-alumina, silica-coated alumina, silica-titania, silica-zirconia, alumina-boria, or any combination thereof. In still another embodiment, the solid oxide can comprise silica, alumina, silica-alumina, silica-coated alumina, or any mixture thereof; alternatively, silica; alternatively, alumina; alternatively, silica-alumina; or alternatively, silica-coated alumina.

The silica-coated alumina solid oxide materials which can be used in the catalyst systems and oligomerization processes often are alumina-rich, for instance, the weight ratio of alumina to silica (alumina:silica) in the silica-coated alumina can be in a range from 1.05:1 to 50:1, from 1.1:1 to 50:1, or from 1.2:1 to 50:1. In one embodiment, the weight ratio of alumina:silica in the silica-coated alumina can be in a range from 1.05:1 to 25:1; alternatively, from 1.05:1 to 12:1; alternatively, from 1.05:1 to 6:1; or alternatively, from 1.05:1 to 4:1. In another embodiment, the weight ratio of alumina:silica in the silica-coated alumina can be in a range from 1.1:1 to 25:1; alternatively, from 1.1:1 to 12:1; alternatively, from 1.1:1 to 7:1; or alternatively, from 1.1:1 to 3:1. In yet another embodiment, the weight ratio of alumina:silica in the silica-coated alumina can be in a range from 1.2:1 to 25:1; alternatively, from 1.2:1 to 12:1; alternatively, from 1.2:1 to 6:1; alternatively, from 1.2:1 to 4:1; or alternatively, from 1.2:1 to 3:1. In still another embodiment, the weight ratio of alumina:silica in the silica-coated alumina can be in a range from 1.3:1 to 25:1; alternatively, from 1.3:1 to 12:1; alternatively, from 1.3:1 to 6:1; alternatively, from 1.3:1 to 4:1; or alternatively, from 1.3:1 to 3:1.

The electron-withdrawing component used to treat the solid oxide can be any component that can increase the Lewis or Brønsted acidity of the solid oxide upon treatment (as compared to the solid oxide that is not treated with at least one electron-withdrawing anion). According to one embodiment, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, acetate, fluorophosphate, trifluoroacetate, triflate, fluorozirconate, fluorotitanate, phospho-tungstate, tungstate, and molybdate, including mixtures and combinations thereof. In addition, other ionic or non-ionic compounds that serve as sources for these electron-withdrawing anions also can be employed. It is contemplated that the electron-withdrawing anion can be, or can comprise, fluoride, chloride, bromide, phosphate, triflate, bisulfate, or sulfate, or any combination thereof, in some embodiments provided herein. In other embodiments, the electron-withdrawing anion can comprise sulfate, bisulfate, fluoride, chloride, bromide, iodide, fluorosulfate, fluoroborate, phosphate, acetate, fluorophosphate, trifluoroacetate, triflate, fluorozirconate, fluorotitanate, or combinations thereof. Yet, in other embodiments, the electron-withdrawing anion can comprise sulfate, fluoride, chloride, or combinations thereof; alternatively, sulfate; alternatively, fluoride and chloride; or alternatively, fluoride.

The chemically-treated solid oxide generally can contain from 1 to 30 wt. % of the electron-withdrawing anion, based on the weight of the chemically-treated solid oxide. In particular embodiments provided herein, the chemically-treated solid oxide can contain from 1 to 20 wt. %, from 2 to 20 wt. %, from 3 to 20 wt. %, from 2 to 15 wt. %, from 3 to 15 wt. %, from 3 to 12 wt. %, from 4 to 10 wt. %, or from 5 to 9 wt. %, of the electron-withdrawing anion, based on the total weight of the chemically-treated solid oxide.

In an embodiment, the chemically-treated solid oxide can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, or phosphated silica-coated alumina, as well as any mixture or combination thereof. In another embodiment, the chemically-treated solid oxide employed in the catalyst systems and oligomerization processes described herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, fluorided-chlorided silica-coated alumina, or sulfated silica-coated alumina, as well as combinations thereof. In yet another embodiment, the chemically-treated solid oxide can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; alternatively, sulfated silica-coated alumina; alternatively, fluorided-chlorided silica-coated alumina; or alternatively, fluorided silica-coated alumina. In some embodiments, the chemically-treated solid oxide can comprise a fluorided solid oxide, while in other embodiments, the chemically-treated solid oxide can comprise a sulfated solid oxide.

Various processes can be used to form chemically-treated solid oxides useful in the present invention. Methods of contacting the solid oxide with the electron-withdrawing component, suitable electron withdrawing components and addition amounts, impregnation with metals or metal ions (e.g., zinc, nickel, vanadium, titanium, silver, copper, gallium, tin, tungsten, molybdenum, zirconium, or combinations thereof), various calcining procedures and conditions (e.g., calcining temperatures in a range from 300° C. to 900° C., from 400° C. to 800° C., or from 500° C. to 700° C.), calcination times (e.g., calcination times in a range from 1 minute to 24 hours, from 5 minutes to 10 hours, or from 20 minutes to 6 hours), calcination equipment (e.g., calcination equipment such as a rotary kiln, muffle furnace, or fluidized bed, among other methods of conveying heat), and calcination atmospheres (e.g., dry or humid calcination atmospheres, oxidizing calcination atmospheres such as air or oxygen, reducing calcination atmospheres such as carbon monoxide or hydrogen, or non-reactive calcination atmospheres like nitrogen or argon) are disclosed in, for example, U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, 6,750,302, 7,294,599, 7,601,665, 7,884,163, and 8,309,485. Other suitable processes and procedures for preparing chemically-treated solid oxides (e.g., chemically-treated silica-coated aluminas, such as fluorided silica-coated alumina) are well known to those of skill in the art.

Organoaluminum Compounds

Generally, the organoaluminum compound utilized in the catalyst systems disclosed herein can be any organoaluminum compound which can catalyze the formation of an oligomer product. In an aspect, the organoaluminum compound can comprise an aluminoxane, an alkylaluminum compound, or a combination thereof; alternatively, an aluminoxane; or alternatively, an alkylaluminum compound. In an embodiment, the alkylaluminum compound can be a trialkylaluminum, an alkylaluminum halide, an alkylaluminum alkoxide, or any combination thereof. In some embodiments, the alkylaluminum compound can be a trialkylaluminum, an alkylaluminum halide, or any combination thereof; alternatively, a trialkylaluminum, an alkylaluminum halide, or any combination thereof; or alternatively, a trialkylaluminum. In other embodiments, the alkylaluminum compound can be a trialkylaluminum; alternatively, an alkylaluminum halide; or alternatively, an alkylaluminum alkoxide.

In an aspect, each alkyl group of any alkylaluminum compound disclosed herein (trialkylaluminum, alkylaluminum halide, or alkylaluminum alkoxide) independently can be, comprise, or consist essentially of, a $C_1$ to $C_{20}$ alkyl group; alternatively, a $C_1$ to $C_{10}$ alkyl group; or alternatively, a $C_1$ to $C_6$ alkyl group. In an embodiment, each alkyl group of any alkylaluminum compound disclosed herein independently can be, comprise, or consist essentially of, a methyl group, an ethyl group, a propyl group, a butyl group, a pentyl group, a hexyl group, a heptyl group, or an octyl group; alternatively, a methyl group, an ethyl group, a butyl group, a hexyl group, or an octyl group. In some embodiments, each alkyl group independently can be, comprise, or consist essentially of, a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, each halide of any alkylaluminum halide disclosed herein can be, comprise, or consist essentially of, chloride, bromide, or iodide. In some embodiments, each halide of any alkylaluminum halide disclosed herein can be, comprise, or consist essentially of, chloride or bromide; or alternatively, chloride.

In an aspect, each alkoxide group of any alkylaluminum alkoxide disclosed herein independently can be, comprise, or consist essentially of, a $C_1$ to $C_{20}$ alkoxy group; alternatively, a $C_1$ to $C_{10}$ alkoxy group; or alternatively, a $C_1$ to $C_6$ alkoxy group. In an embodiment, each alkoxide group of any alkylaluminum alkoxide disclosed herein independently can be, comprise, or consist essentially of, a methoxy group, an ethoxy group, a propoxy group, a butoxy group, a pentoxy group, a hexoxy group, a heptoxy group, or an octoxy group; alternatively, a methoxy group, an ethoxy group, a butoxy group, a hexoxy group, or an octoxy group. In some embodiments, each alkoxide group of any alkylaluminum alkoxide disclosed herein independently can be, comprise, or consist essentially of, a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In a non-limiting embodiment, the trialkylaluminum compound can be, comprise, or consist essentially of, trimethylaluminum, triethylaluminum, tripropylaluminum, tributylaluminum, trihexylaluminum, trioctylaluminum, or mixtures thereof. In some non-limiting embodiments, the trialkylaluminum compound can be, comprise, or consist essentially of, trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting embodiments, the trialkylaluminum compound can be, comprise, or consist essentially of, trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting embodiment, the alkylaluminum halide can be, comprise, or consist essentially of, diethylaluminum chloride, diethylaluminum bromide, ethylaluminum dichloride, ethylaluminum sesquichloride, or mixtures thereof. In some non-limiting embodiments, the alkylaluminum halide can be, comprise, or consist essentially of, diethylaluminum chloride, ethylaluminum dichloride, ethylaluminum sesquichloride, or mixtures thereof. In other non-limiting embodiments, the alkylaluminum halide can be, comprise, or consist essentially of, diethylaluminum chloride; alternatively, diethylaluminum bromide; alternatively, ethylaluminum dichloride; or alternatively, ethylaluminum sesquichloride.

In particular aspects of this invention, the organoaluminum compound can comprise trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum (TNOA), diisobutylaluminum hydride, diethylaluminum ethoxide, diethylaluminum chloride, or combinations thereof.

Aluminoxanes

In a non-limiting embodiment, the aluminoxane can have a repeating unit characterized by the Formula I:

(Formula I)

wherein R' is a linear or branched alkyl group. Alkyl groups for the aluminoxane compounds are independently described herein and can be utilized without limitation to further describe the aluminoxanes having Formula I. Generally, n of Formula I can be greater than 1, or alternatively, greater than 2. In an embodiment, n can range from 2 to 15, or alternatively, n can range from 3 to 10.

In a non-limiting embodiment, the aluminoxane can be, comprise, or consist essentially of, methylaluminoxane (MAO), ethylaluminoxane, modified methylaluminoxane (MMAO), n-propylaluminoxane, iso-propyl-aluminoxane, n-butylaluminoxane, sec-butylaluminoxane, iso-butylaluminoxane, t-butylaluminoxane, 1-pentyl-aluminoxane, 2-pentyl-aluminoxane, 3-pentyl-aluminoxane, iso-pentyl-aluminoxane, neopentylaluminoxane, or mixtures thereof. In some non-limiting embodiments, the aluminoxane can be, comprise, or consist essentially of, methylaluminoxane (MAO), modified methylaluminoxane (MMAO), isobutyl aluminoxane, t-butyl aluminoxane, or mixtures thereof. In other non-limiting embodiments, the aluminoxane can be, comprise, or consist essentially of, methylaluminoxane (MAO); alternatively, ethylaluminoxane; alternatively, modified methylaluminoxane (MMAO); alternatively, n-propylaluminoxane; alternatively, iso-propyl-aluminoxane; alternatively, n-butylaluminoxane; alternatively, sec-butylaluminoxane; alternatively, iso-butylaluminoxane; alternatively, t-butyl aluminoxane; alternatively, 1-pentyl-aluminoxane; alternatively, 2-pentylaluminoxane; alternatively, 3-pentyl-1aluminoxane; alternatively, iso-pentyl-aluminoxane; or alternatively, neopentylaluminoxane.

Processes for Preparing the Catalyst Systems

Generally, the process for preparing the catalyst system can comprise (or consist essentially of, or consist of) contacting a heteroatomic ligand transition metal compound complex, a chemically-treated solid oxide, and an organoaluminum compound to form a catalyst system mixture. In some embodiments the catalyst system mixture can be aged for a period of time. Typically, the minimum aging time can be 5 seconds, 10 seconds, 30 seconds, 1 minute, 5 minutes, 10 minutes, or 20 minutes; additionally or alternatively, the maximum aging time can be 48 hours, 36 hours, 24 hours, 18 hours, 12 hours, 6 hours, 4 hours, or 2 hours. Generally, the aging time can be in a range from any minimum time disclosed herein to any maximum time disclosed herein. Accordingly, suitable non-limiting ranges for the aging time can include the following: from 5 seconds to 48 hours, from 10 seconds to 36 hours, from 30 seconds to 24 hours, from 1 minute to 18 hours, from 5 minutes to 6 hours, from 10 minutes to 4 hours, or from 20 minutes to 2 hours. Other appropriate ranges for the aging time are readily apparent from this disclosure. In further embodiments, the heteroatomic ligand transition metal compound complex, the chemically-treated solid oxide, and the organoaluminum compound can be contacted and/or aged at any suitable temperature, ranging from sub-ambient temperatures, to ambient temperature (approximately 25° C.), to elevated temperatures. While not limited thereto, the heteroatomic ligand transition metal compound complex, the chemically-treated solid oxide, and the organoaluminum compound can be contacted and/or aged at a temperature in a range from 0° C. to 100° C., from 10° C. to 75° C., from 15° C. to 60° C., or from 20° C. to 40° C. In these and other embodiments, these temperature ranges also are meant to encompass circumstances where the heteroatomic ligand transition metal compound complex, the chemically-treated solid oxide, and the organoaluminum compound can be contacted and/or the catalyst system aged at a series of different temperatures, instead of at a single fixed temperature, falling within the respective ranges.

Various catalyst system preparation processes relating to how the heteroatomic ligand transition metal compound complex (one or more), the chemically-treated solid oxide (one or more), and the organoaluminum compound (one or more) can be contacted are disclosed and described herein. While these processes for preparing the catalyst systems may be referred to as a first process, second process, third process etc., these designations do not imply that there is any preference or advantage to the process for preparing the catalyst system. A first process for preparing the catalyst system can comprise (or consist essentially of, or consist of): (i) contacting a chemically-treated solid oxide and an organoaluminum compound for a first period of time to form a precontacted mixture; and (ii) contacting the precontacted mixture with a heteroatomic ligand transition metal compound complex for a second period of time to form the catalyst system.

A second process for preparing a catalyst system in accordance with this invention can comprise: (i) contacting a heteroatomic ligand transition metal compound complex and an organoaluminum compound for a first period of time to form a precontacted mixture; and (ii) contacting the precontacted mixture with a chemically-treated solid oxide for a second period of time to form the catalyst system.

Generally, the features of any of the first and second processes for preparing the catalyst system disclosed herein (e.g., the heteroatomic ligand transition metal compound complex, the chemically-treated solid oxide, the organoaluminum compound, the first period of time, and the second period of time, among others) are independently described herein, and these features can be combined in any combination to further describe the disclosed first and second processes for preparing the catalyst system. Moreover, other process steps can be conducted before, during, and/or after any of the steps listed in the disclosed first and second processes for preparing the catalyst system, unless stated otherwise. Additionally, catalyst systems produced in accordance with the disclosed first and second processes for preparing the catalyst system are within the scope of this disclosure and are encompassed herein.

The duration of the precontacting step (the first period of time) in the first and second processes for preparing the catalyst system is not limited to any particular period of time. Likewise, assuming that the catalyst system is not intended for long term storage, which could extend for days or weeks, the second period of time in not limited to any particular period of time. The appropriate first period of time and second period of time independently can depend upon, for example, the relative amounts of the respective catalyst system components, the temperatures at which the components are contacted, the presence of diluents or solvents in the contacting steps, and the degree of mixing, among other variables. Typically, however, the minimum first period of time and second period of time, independently, can be 5 seconds, 10 seconds, 30 seconds, 1 minute, 5 minutes, 10 minutes, or 20 minutes; additionally or alternatively, the maximum first period of time and second period of time, independently, can be 48 hours, 36 hours, 24 hours, 18 hours, 12 hours, 6 hours, 4 hours, or 2 hours. Generally, the first period of time and the second period of time can be in a range from any minimum time disclosed herein to any maximum time disclosed herein. Accordingly, suitable non-limiting ranges for the first period of time and the second period of time independently can include the following: from 5 seconds to 48 hours, from 10 seconds to 36 hours, from 30 seconds to 24 hours, from 1 minute to 18 hours, from 5 minutes to 6 hours, from 10 minutes to 4 hours, or from 20 minutes to 2 hours. Other appropriate ranges for the first period of time and the second period of time are readily apparent from this disclosure.

Steps (i) and (ii) of the first and second processes for preparing the catalyst system can be conducted at any suitable temperature, ranging from sub-ambient temperatures, to ambient temperature (approximately 25° C.), to elevated temperatures. While not limited thereto, step (i) and step (ii), independently can be conducted at a temperature in a range from 0° C. to 100° C., from 10° C. to 75° C., from 15° C. to 60° C., or from 20° C. to 40° C. In these and other embodiments, these temperature ranges also are meant to encompass circumstances where step (i) or step (ii) is conducted at a series of different temperatures, instead of at a single fixed temperature, falling within the respective ranges.

In the first and second processes for preparing the catalyst system, the respective catalyst system components can be in any suitable phase and contacted in any manner. For instance, the chemically-treated solid oxide can be contacted with the other catalyst system components as a dry solid, or alternatively, as a slurry in a suitable diluent. Likewise, the organoaluminum compound can be contacted with the other catalyst system components as a neat liquid, or alternatively, as a solution in a suitable diluent.

A third process for preparing a catalyst system in accordance with this invention can comprise: (i) contacting a chemically-treated solid oxide and a first organoaluminum compound for a first period of time to form a first mixture; (ii) contacting a heteroatomic ligand transition metal compound complex and a second organoaluminum compound for a second period of time to form a second mixture; and (iii) contacting the first mixture with the second mixture for a third period of time to form the catalyst system.

Generally, the features of the third process for preparing the catalyst system (e.g., the heteroatomic ligand transition metal compound complex, the chemically-treated solid oxide, the organoaluminum compound, the first period of time, the second period of time, and the third period of time, among others) are independently described herein, and these features can be combined in any combination to further describe the third process for preparing the catalyst system. Moreover, other process steps can be conducted before, during, and/or after any of the steps listed in the disclosed third process for preparing the catalyst system, unless stated otherwise. Additionally, catalyst systems produced in accordance with this process are within the scope of this disclosure and are encompassed herein.

The duration of the organoaluminum precontacting steps (the first period of time and the second period of time) in the process for preparing the catalyst system is not limited to any particular period of time. Likewise, assuming that the catalyst system is not intended for long term storage, which could extend for days or weeks, the third period of time in not limited to any particular period of time. The appropriate first period of time, second period of time, and third period of time independently can depend upon, for example, the relative amounts of the respective catalyst system components, the temperatures at which the components are contacted, the presence of diluents or solvents in the contacting steps, and the degree of mixing, among other variables. Typically, however, the minimum first period of time, second period of time, and third period of time, independently, can be 5 seconds, 10 seconds, 30 seconds, 1 minute, 5 minutes, 10 minutes, or 20 minutes; additionally or alternatively, the maximum first period of time, second period of time, and third period of time, independently, can be 48 hours, 36 hours, 24 hours, 18 hours, 12 hours, 6 hours, 4 hours, or 2 hours. Generally, the first period of time, the second period of time, and the third period of time independently can be in a range from any minimum time disclosed herein to any maximum time disclosed herein. Accordingly, suitable non-limiting ranges for the first period of time, the second period of time, and the third period of time can include the following: from 5 seconds to 48 hours, from 10 seconds to 36 hours, from 30 seconds to 24 hours, from 1 minute to 18 hours, from 5 minutes to 6 hours, from 10 minutes to 4 hours, or from 20 minutes to 2 hours. Other appropriate ranges for the first period of time, the second period of time, and the third period of time are readily apparent from this disclosure.

As with the other processes for preparing catalyst systems in accordance with this invention, steps (i), (ii), and (iii) of the third process for preparing the catalyst system can be conducted at any suitable temperature, and the respective catalyst system components can be in any suitable phase and contacted in any manner, as would be recognized by one of skill in the art. Moreover, the first organoaluminum compound in step (i) can be the same as or different from the second organoaluminum compound in step (ii).

A fourth process for preparing the catalyst system can comprise (or consist essentially of, or consist of): i) contacting the chemically-treated solid oxide and the heteroatomic ligand transition metal compound complex for a first period of time to form a precontacted mixture, ii) contacting the precontacted mixture with the organoaluminum compound for a second period of time to form the catalyst system. Generally, the features of the fourth process for preparing the catalyst system (e.g., the heteroatomic ligand transition metal compound complex, the chemically-treated solid oxide, the organoaluminum compound, the first period of time, and the second period of time, among others) are independently described herein, and these features can be combined in any combination to further describe the fourth process for preparing the catalyst system. Moreover, other process steps can be conducted before, during, and/or after any of the steps listed in the disclosed fourth process for preparing the catalyst system, unless stated otherwise. Additionally, catalyst systems produced in accordance with this process are within the scope of this disclosure and are encompassed herein.

The duration of the first period of time and the second period of time in the fourth process for preparing the catalyst system is not limited to any particular period of time. Likewise, assuming that the catalyst system is not intended for long term storage, which could extend for days or weeks, the second period of time in not limited to any particular period of time. The appropriate first period of time and second period of time independently can depend upon, for example, the relative amounts of the respective catalyst system components, the temperatures at which the components are contacted, the presence of diluents or solvents in the contacting steps, and the degree of mixing, among other variables. Typically, however, the minimum first period of time and second period of time, independently, can be 5 seconds, 10 seconds, 30 seconds, 1 minute, 5 minutes, 10 minutes, or 20 minutes; additionally or alternatively, the maximum first period of time and second period of time, independently, can be 48 hours, 36 hours, 24 hours, 18 hours, 12 hours, 6 hours, 4 hours, or 2 hours. Generally, the first period of time and the second period of time independently can be in a range from any minimum time disclosed herein to any maximum time disclosed herein. Accordingly, suitable non-limiting ranges for the first period of time and the second period of time, independently, can include the following: from 5 seconds to 48 hours, from 10 seconds to 36 hours, from 30 seconds to 24 hours, from 1 minute to 18 hours, from 5 minutes to 6 hours, from 10 minutes to 4 hours, or from 20 minutes to 2 hours. Other appropriate ranges for the first period of time and the second period of time are readily apparent from this disclosure.

Steps (i) and (ii) of the fourth processes for preparing the catalyst system can be conducted at any suitable temperature, ranging from sub-ambient temperatures, to ambient temperature (approximately 25° C.), to elevated temperatures. While not limited thereto, step (i) and step (ii), independently can be conducted at a temperature in a range from 0° C. to 100° C., from 10° C. to 75° C., from 15° C. to 60° C., or from 20° C. to 40° C. In these and other embodiments, these temperature ranges also are meant to encompass circumstances where step (i) or step (ii) is conducted at a series of different temperatures, instead of at a single fixed temperature, falling within the respective ranges.

In the fourth process for preparing the catalyst system, the respective catalyst system components can be in any suitable phase and contacted in any manner. For instance, the chemically-treated solid oxide can be contacted with the other catalyst system components as a dry solid, or alternatively, as a slurry in a suitable diluent. Likewise, the organoaluminum compound can be contacted with the other catalyst system components as a neat liquid, or alternatively, as a solution in a suitable diluent.

A fifth process for preparing the catalyst system can comprise (or consist essentially of, or consist of) simultaneously contacting the chemically-treated solid oxide, the organoaluminum compound, and the heteroatomic ligand transition metal compound complex for a period of time to form the catalyst system. Generally, the features of the fifth process for preparing the catalyst system (e.g., the heteroatomic ligand transition metal compound complex, the chemically-treated solid oxide, the organoaluminum compound, and the period of time, among others) are independently described herein, and these features can be combined in any combination to further describe the fifth process for preparing the catalyst system. Moreover, other process steps can be conducted before, during, and/or after any of the steps listed in the disclosed fifth process for preparing the catalyst system, unless stated otherwise. Additionally, catalyst systems produced in accordance with this process are within the scope of this disclosure and are encompassed herein.

The duration of the period of time in the fifth process for preparing the catalyst system is not limited to any particular period of time. Likewise, assuming that the catalyst system is not intended for long term storage, which could extend for days or weeks, the period of time in not limited to any particular period of time. The appropriate period of time can depend upon, for example, the relative amounts of the respective catalyst system components, the temperatures at which the components are contacted, the presence of diluents or solvents in the contacting steps, and the degree of mixing, among other variables. Typically, however, the minimum period of time can be 5 seconds, 10 seconds, 30 seconds, 1 minute, 5 minutes, 10 minutes, or 20 minutes; additionally or alternatively, the maximum period of time can be 48 hours, 36 hours, 24 hours, 18 hours, 12 hours, 6 hours, 4 hours, or 2 hours. Generally, the period of time can be in a range from any minimum time disclosed herein to any maximum time disclosed herein. Accordingly, suitable non-limiting ranges for the period of time can include the following: from 5 seconds to 48 hours, from 10 seconds to 36 hours, from 30 seconds to 24 hours, from 1 minute to 18 hours, from 5 minutes to 6 hours, from 10 minutes to 4 hours, or from 20 minutes to 2 hours. Other appropriate ranges for the period of time are readily apparent from this disclosure.

In the fifth processes for preparing the catalyst system can be formed at any suitable temperature, ranging from sub-ambient temperatures, to ambient temperature (approximately 25° C.), to elevated temperatures. While not limited thereto, the catalyst system can be formed at a temperature in a range from 0° C. to 100° C., from 10° C. to 75° C., from 15° C. to 60° C., or from 20° C. to 40° C. In these and other embodiments, these temperature ranges also are meant to encompass circumstances where the catalyst system is formed at a series of different temperatures, instead of at a single fixed temperature, falling within the respective ranges.

In the fifth process for preparing the catalyst system, the respective catalyst system components can be in any suitable phase and contacted in any manner. For instance, the chemically-treated solid oxide can be contacted with the other catalyst system components as a dry solid, or alternatively, as a slurry in a suitable diluent. Likewise, the organoaluminum compound can be contacted with the other catalyst system components as a neat liquid, or alternatively, as a solution in a suitable diluent.

Unexpectedly, these processes for preparing catalyst systems can result in improvements in catalyst activity. For instance, the productivity of the catalyst system prepared by any of these three processes (in kg $(C_6+C_8)$/g transition metal, kg $(C_6+C_8)$/g transition metal/hr, or kg $(C_6+C_8)$/g Al) can be greater (e.g., by at least 10%, at least 25%, at least 50%, at least 100%, from 10% to 500% greater, from 25% to 200% greater, from 50% to 300% greater, etc.) than that of a catalyst system obtained by contacting the chemically-treated solid oxide and the heteroatomic ligand transition metal compound complex to form a first mixture, and then contacting the first mixture with the organoaluminum compound, or a catalyst system obtained by simultaneously contacting the chemically-treated solid oxide, the heteroatomic ligand transition metal compound complex, and the organoaluminum compound. This comparison is meant to be at the same oligomerization conditions (e.g., oligomerization temperature, ethylene pressure, etc.) and with the same catalyst system components (e.g., same amount/type of heteroatomic ligand transition metal compound, same amount/type of organoaluminum, same amount/type of chemically-treated solid oxide, such as fluorided silica-coated alumina or sulfated alumina, etc.). The same oligomerization conditions refer to using cyclohexane as a diluent, with an oligomerization temperature of 70° C., an ethylene pressure of 875 psig, and a hydrogen pressure of 50 psig. Hence, the only difference is the method used to produce the catalyst system, i.e., the order or sequence of contacting the respective catalyst components.

Generally, in the catalyst systems and methods of their preparation disclosed herein, the weight ratio of chemically-treated solid oxide(s) to organoaluminum compound(s) can be in a range from 1:10 to 1000:1, or from 1:5 to 1000:1. If more than one organoaluminum compound and/or more than one chemically-treated solid oxide are employed, this ratio is based on the total weight of each respective component. In an embodiment, the weight ratio of the chemically-treated solid oxide to the organoaluminum compound can be in a range from 1:1 to 500:1, from 1:1 to 200:1, or from 1:1 to 100:1.

Likewise, the weight ratio of transition metal(s) of the heteroatomic ligand transition metal compound complex(es) to chemically-treated solid oxide(s) can be in a range from 1:1 to 1:1,000,000, or from 1:5 to 1:250,000. If more than one transition metal (or heteroatomic ligand transition metal compound complex) and/or more than one chemically-treated solid oxide are employed, this ratio is based on the total weight of each respective component. In an embodiment, the weight ratio of the transition metal of the heteroatomic ligand transition metal compound complex to the chemically-treated solid oxide can be in a range from 1:10 to 1:10,000, or from 1:20 to 1:1000.

In some embodiments, the catalyst systems and methods of their preparation are substantially free of aluminoxane compounds. In these embodiments, the catalyst system has catalyst activity or productivity, as discussed herein, in the substantial absence of an aluminoxane. For example, a catalyst system of the present invention can consist essentially of a heteroatomic ligand transition metal compound complex, a chemically-treated solid oxide, and an organoaluminum compound, wherein no other materials are present in the catalyst system which would increase/decrease the activity or productivity of the catalyst system by more than about 10% from the catalyst activity or productivity of the catalyst system in the absence of said materials (e.g., aluminoxane materials).

Herein, substantially free of aluminoxane compounds or the substantial absence of an aluminoxane means that the catalyst system contain less than 5 wt. %, 2.5 wt. %, 1 wt. %, 0.5 wt. %, 0.25 wt. %, or 0.1 wt. % aluminoxane, based upon the total amount of organoaluminum compound in the catalyst system.

Processes for Preparing an Oligomer Product

Embodiments of this invention are directed to ethylene oligomerization processes, the production of an oligomer product, and the formation and recovery of a liquid oligomer product; or alternatively, the production of an oligomer product, and the formation and recovery of a liquid oligomer product and a solid polymer product. Typical properties for the liquid oligomer, portions of the liquid oligomer product, and the solid polymer product are disclosed herein and can be used without limitation to further describe the ethylene oligomerization processes describe herein. One such process can comprise (or consist essentially of, or consist of) (a) contacting ethylene, any of the catalyst systems disclosed herein, and an optional organic reaction medium, and (b) forming an oligomer product. Another process consistent with this invention can comprise (or consist essentially of, or consist of) (a) preparing a catalyst system in accordance with any method disclosed herein, (b) contacting the catalyst system prepared in step (a) with ethylene and an optional organic reaction medium, and (c) forming an oligomer product. In an embodiment of the ethylene oligomerization process described herein, the oligomer product can be formed in a reaction zone.

Generally, the features of the processes described herein (e.g., the catalyst system, the method of preparing the catalyst system, the organic reaction medium, the materials comprising and/or features of the oligomer product, the oligomerization (trimerization, tetramerization, or trimerization and tetramerization) conditions under which the oligomer (trimerization, tetramerization, or trimerization and tetramerization) product is formed, the reaction zone, among others) are independently described herein, and these features can be combined without limitation, and in any combination, to further describe the disclosed processes. Moreover, additional process steps can be performed before, during, and/or after any of the steps of any of the processes disclosed herein, unless stated otherwise.

In some embodiments, the oligomer product can be formed in the presence of an organic reaction medium. When employed, any suitable organic reaction medium can be used. In an embodiment, the organic reaction medium can be a hydrocarbon. Hydrocarbons can include, for example, aliphatic hydrocarbons, aromatic hydrocarbons, petroleum distillates, or combinations thereof; alternatively, aliphatic hydrocarbons; or alternatively, aromatic hydrocarbons. Aliphatic hydrocarbons which can be used as an organic reaction medium include $C_3$ to $C_{20}$ aliphatic hydrocarbons; alternatively $C_4$ to $C_{15}$ aliphatic hydrocarbons; or alternatively, $C_5$ to $C_{10}$ aliphatic hydrocarbons. The aliphatic hydrocarbons can be cyclic or acyclic and/or can be linear or branched, unless otherwise specified. In some embodiments, the aliphatic hydrocarbon which can be utilized as the organic reaction medium can be a hydrocarbon olefin (linear or branched, or terminal or internal). Non-limiting examples of suitable acyclic aliphatic hydrocarbon reaction medium that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or a mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), or combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or a mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), or combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), or combinations thereof; alternatively, propane; alternatively, iso-butane; alternatively, n-butane; alternatively, butane (n-butane or a mixture of linear and branched $C_4$ acyclic aliphatic hydrocarbons); alternatively, pentane (n-pentane or a mixture of linear and branched $C_5$ acyclic aliphatic hydrocarbons); alternatively, hexane (n-hexane or a mixture of linear and branched $C_6$ acyclic aliphatic hydrocarbons); alternatively, heptane (n-heptane or a mixture of linear and branched $C_7$ acyclic aliphatic hydrocarbons); or alternatively, octane (n-octane or a mixture of linear and branched $C_8$ acyclic aliphatic hydrocarbons). In other embodiments, the acyclic aliphatic reaction medium can be a product of the oligomerization (1-hexene and/or 1-octene). Non-limiting examples of suitable cyclic aliphatic hydrocarbon reaction medium include cyclohexane and methyl cyclohexane; alternatively, cyclohexane; or alternatively, methylcyclohexane. Aromatic hydrocarbons which can be useful as an organic reaction medium include $C_6$ to $C_{20}$ aromatic hydrocarbons, or alternatively, $C_6$ to $C_{10}$ aromatic hydrocarbons. Non-limiting examples of suitable aromatic hydrocarbons that can be utilized singly or in any combination include benzene, toluene, xylene (including ortho-xylene, meta-xylene, para-xylene, or mixtures thereof), and ethylbenzene, or combinations thereof; alternatively, benzene; alternatively, toluene; alternatively, xylene (including ortho-xylene, meta-xylene, para-xylene or mixtures thereof); or alternatively, ethylbenzene.

The oligomer product can be formed at any suitable temperature or a temperature in any range disclosed herein. Often, the oligomer product can be formed at a minimum temperature of 0° C., 20° C., 30° C., 40° C., 45° C., or 50° C.; additionally or alternatively, at a maximum temperature of 165° C., 160° C., 150° C., 140° C., 130° C., 115° C., 100° C., or 90° C. Generally, the temperature at which the oligomer product is formed can be in a range from any minimum temperature disclosed herein to any maximum temperature disclosed herein. Accordingly, suitable non-limiting ranges can include the following: from 0° C. to 165° C., from 20° C. to 160° C., from 20° C. to 115° C., from 40° C. to 160° C., from 40° C. to 140° C., from 50° C. to 150° C., from 50° C. to 140° C., from 50° C. to 130° C., from 50° C. to 100° C., from 45° C. to 115° C., from 45° C. to 100° C., or from 45° C. to 90° C. Other appropriate temperatures and temperature ranges at which the oligomer product can be formed are readily apparent from this disclosure.

The oligomer product can be formed at any suitable pressure or a pressure in any range disclosed herein. For example, the oligomer product can be formed at a minimum pressure (or ethylene partial pressure) of 50 psig (344 kPa), 100 psig (689 kPa), 200 psig (1.4 MPa), or 250 psig (1.5 MPa); additionally or alternatively, at a maximum pressure (or ethylene partial pressure) of 4,000 psig (27.6 MPa), 3,000 psig (20.9 MPa), 2,000 psig (13.8 MPa), or 1,500 psig (10.3 MPa). Generally, the pressure (or ethylene partial pressure) at which the oligomer product is formed can be in a range from any minimum pressure disclosed herein to any maximum pressure disclosed herein. Accordingly, suitable non-limiting ranges can include the following: from 50 psig (344 kPa) to 4,000 psig (27.6 MPa), from 100 psig (689 kPa) to 3,000 psig (20.9 MPa), from 100 psig (689 kPa) to 2,000 psig (13.8 MPa), from 200 psig (1.4 MPa) to 2,000 psig (13.8 MPa), from 200 psig (1.4 MPa) to 1,500 psig (10.3 MPa), or from 250 psig (1.5 MPa) to 1,500 psig (10.3 MPa). Other appropriate pressures (or ethylene partial pressures) at which the oligomer product can be formed are readily apparent from this disclosure.

In some embodiments, the oligomer product can be formed in the substantial absence of hydrogen. In these embodiments, the oligomer product is formed in the substantial absence of added hydrogen. As one of ordinary skill in the art would recognize, hydrogen can be generated in-situ by transition metal-based catalyst systems in various olefin oligomerization processes, and the amount generated can vary depending upon the specific catalyst system and heteroatomic ligand transition metal compound complex employed, the type of oligomerization process used, the oligomerization reaction conditions utilized, and so forth. Herein the substantial absence of hydrogen is defined as forming the oligomer product at partial pressure of added hydrogen of less than less than 1 psig (6.9 kPa), 0.5 psig (3.45 kPa), 0.25 psig (1.72 kPa), or 0.1 psig (0.69 kPa).

In other embodiments, it may be desirable to form the oligomer product in the presence of a of added hydrogen, for instance, to modify the molecular weight of the solid polymer, etc. In some embodiments, the productivity of the catalyst system can be increased by performing the oligomerization in the presence of hydrogen. Accordingly, in these embodiments, the oligomer product can be formed in the presence of hydrogen, i.e., ethylene, the catalyst system, hydrogen, and an optional organic reaction medium can be contacted to form the oligomer product as described herein. For instance, the oligomer product can be formed at a hydrogen partial pressure of at least 1 psig (6.9 kPa), 5 psig (34 kPa), 10 psig (69 kPa), 25 psig (172 kPa), or 50 psig (345 kPa); additionally or alternatively, the oligomer product can be formed at a maximum hydrogen partial pressure of 2000 psig (13.8 MPa), 1750 psig (12.1 MPa), 1500 psig (10.3 MPa), 1250 psig (8.6 MPa), 1000 psig (6.9 MPa), 750 psig (5.2 MPa), 500 psig (3.4 MPa), or 400 psig (2.8 MPa). Generally, the hydrogen partial pressure can range from any minimum hydrogen partial pressure disclosed herein to any maximum hydrogen partial pressure disclosed herein. Therefore, suitable non-limiting ranges for the hydrogen partial pressure can include the following ranges: from 1 psig (6.9 kPa) to 2000 psig (13.8 MPa), from 1 psig (6.9 kPa) to 1750 psig (12.1 MPa), from 5 psig (34 kPa) to 1500 psig (10.3 MPa), from 5 psig (34 kPa) to 1250 psig (8.6 MPa), from 10 psig (69 kPa) to 1000 psig (6.9 MPa), from 10 psig (69 kPa) to 750 psig (5.2 MPa), from 10 psig (69 kPa) to 500 psig (3.5 MPa), from 25 psig (172 kPa) to 750 psig (5.2 MPa), from 25 psig (172 kPa) to 500 psig (3.4 MPa), from 25 psig (172 kPa) to 400 psig (2.8 MPa), or from 50 psig (345 kPa) to 500 psig (3.4 MPa). Other appropriate hydrogen partial pressures at which the oligomer product can be formed are readily apparent from this disclosure.

The reaction zone in which the oligomer product can be formed can comprise any suitable reactor. Non-limiting examples of reactors can include a stirred tank reactor, a plug flow reactor, or any combination thereof; alternatively, a fixed bed reactor, a continuous stirred tank reactor, a loop slurry reactor, a solution reactor, a tubular reactor, a recycle reactor, or any combination thereof. In an embodiment, the reaction zone can have more than one reactor in series or in parallel, and including any combination of reactor types and arrangements. Moreover, the oligomerization process used to form the oligomer product can be a continuous process or a batch process, or any reactor or vessel within the oligomerization reaction system can be operated continuously or batchwise.

The process described herein can include a step of discharging a reaction zone effluent comprising the oligomer product; alternatively, the oligomer product and the catalyst system; alternatively, the oligomer product and the solid polymer; or alternatively, the oligomer product, the solid polymer, and the catalyst system. In further embodiments the reaction zone effluent can further comprise ethylene and/or the optional organic reaction medium. In some processes described herein, the catalyst system can be deactivated. Deactivating the catalyst system can comprise contacting the reaction zone effluent with a suitable catalyst system deactivating agent, or subjecting the oligomer product to suitable process steps to deactivate the catalyst system, or a combination of both. The reaction zone effluent wherein the catalyst system has been deactivated can be referred to as a deactivated reaction zone effluent. The catalyst system deactivating agent can comprise (or consist essentially of, or consist of) water, an alcohol compound, an amine compound, or any combination thereof; alternatively, water; alternatively, an alcohol compound; or alternatively, an amine compound. In an embodiment, the alcohol compound can be a monoalcohol compound, a diol compound, a polyol compound, or any combination thereof. In some embodiments, the alcohol compound can comprise, consist essentially of, or consist of, a $C_1$ to $C_{20}$ mono alcohol. In some embodiments, the alcohol compound can comprise, consist essentially of, or consist of, methanol, ethanol, a propanol, a butanol, a pentanol, a hexanol, a heptanol, an octanol, a nonanol, a decanol, an undecanol, or mixtures thereof. In some embodiments, the alcohol compound can comprise, consist essentially of, or consist of, methanol, ethanol, 1-propanol, 2-propanol, 1-butanol, 2-butanol, isobutanol, sec-butanol, t-butanol, 1-hexanol, 2-hexanol, 3-hexanol, 1-heptanol, 2-heptanol, 3-heptanol, 4-heptanol, 1-octanol, 2-octanol, 3-octanol, 4-octanol, 2-ethyl-1-hexanol, 2-methyl-3-heptanol, 1-decanol, 2-decanol, 3-decanol, 4-decanol, 5-decanol, 1-undecanol, 2-undecanol, 7-methyl-2-decanol, a 1-docecanol, a 2-dodecanol, 2-ethyl-1-decanol, or mixtures thereof.

Additionally or alternatively, the catalyst system can be deactivated by contact with an aqueous base solution or aqueous acid solution (e.g., an aqueous Group 1 metal hydroxide solution or an aqueous mineral acid solution). Such deactivation processes to deactivate the catalyst system can also potentially remove a portion, or substantially all, of the metal catalyst system components from the oligomer product.

In some embodiments, the oligomer product can be formed in the substantial absence of aluminoxanes. In these embodiments, the oligomerization process can be conducted in the absence of these aluminoxane materials. For example, the process can be conducted wherein no other materials are present which would increase/decrease the activity or productivity of the catalyst system by more than about 10% from the catalyst activity or productivity of the catalyst system in the absence of said materials (e.g., aluminoxane materials). Herein, the substantial absence of aluminoxane means that the catalyst system contain less than 5 wt. %, 2.5 wt. %, 1 wt. %, 0.5 wt. %, 0.25 wt. %, or 0.1 wt. % aluminoxane, based upon the total amount of organoaluminum compound in the process.

In accordance with the processes of this invention, the productivity of the catalyst system under oligomerization conditions generally can be greater than 25,000 grams, greater than 50,000 grams, greater than 100,000 grams, greater than 150,000 grams, or greater than 200,000 grams, and often up to 350,000-500,000 grams, of $C_6+C_8$ per gram of transition metal (from the heteroatomic ligand transition metal compound complex). For the purpose of determining the productivity, the conditions under the oligomer product is formed can include a triethylaluminum co-catalyst, using cyclohexane as the reaction medium and 50 psig hydrogen pressure, and with an oligomerization temperature of 70° C. and an ethylene pressure of 875 psig.

Additionally or alternatively, the productivity of the catalyst system under oligomerization conditions generally can be greater than 1,000 grams, greater than 2,500 grams, greater than 10,000 grams, greater than 25,000 grams, greater than 50,000 grams, or greater than 100,000 grams, and often up to 150,000-250,000 grams, of ethylene polymer per gram of transition metal (from the heteroatomic ligand transition metal compound complex). For the purpose of determining the productivity, the conditions under the oligomer product is formed can include a triethylaluminum co-catalyst, using cyclohexane as the reaction medium and 50 psig hydrogen pressure, and with an oligomerization temperature of 70° C. and an ethylene pressure of 875 psig.

Unexpectedly, the first, second, and third processes for preparing the catalyst system disclosed herein can result in improvements in the productivity of the catalyst system when utilized in the disclosed ethylene oligomerization processes in comparison to the fourth and fifth processes for preparing the catalyst system disclosed herein. The oligomerization productivity of the catalyst systems prepared by the first, second, and third catalyst system preparation processes (in kg $(C_6+C_8)$/g transition metal, kg $(C_6+C_8)$/g transition metal/hr, or kg $(C_6+C_8)$/g Al) can be greater (e.g., by at least 10%, at least 25%, at least 50%, at least 100%, from 10% to 500% greater, from 25% to 200% greater, from 50% to 300% greater, etc.) than that of a catalyst system obtained by contacting the chemically-treated solid oxide and the heteroatomic ligand transition metal compound complex to form a first mixture, and then contacting the first mixture with the organoaluminum compound; or a catalyst system obtained by simultaneously contacting the chemically-treated solid oxide, the heteroatomic ligand transition metal compound complex, and the organoaluminum compound. This comparison is meant to be at the same oligomerization conditions (e.g., oligomerization temperature, ethylene pressure, etc.) and with the same catalyst system components (e.g., same amount/type of heteroatomic ligand transition metal compound, same amount/type of organoaluminum, same amount/type of chemically-treated solid oxide, such as fluorided silica-coated alumina or sulfated alumina, etc.). Accordingly, the same oligomerization conditions can encompass identical catalyst system components, catalyst system component ratios, and ethylene oligomerization conditions. Alternatively, and for the purpose of determining the productivity, the same ethylene oligomerization conditions can refer to using cyclohexane as the reaction medium, with an oligomerization temperature of 70° C., an ethylene pressure of 875 psig, and a hydrogen pressure of 50 psig. Hence, the only difference is the method used to produce the catalyst system, i.e., the order or sequence of contacting the respective catalyst components. While it has been discovered that there are unexpected advantages to using the first, second, and third catalyst system preparation processes over the fourth and fifth catalyst system preparation processes, this in no way implies that the fourth and fifth catalyst system preparation processes cannot be used in the ethylene oligomerization process described herein.

Consistent with embodiments of this invention, the oligomer product can comprise a liquid oligomer product and a solid polymer product. That is, the liquid oligomer product is a liquid at standard temperature (25° C.) and pressure (1 atm), and the solid polymer product is a solid at standard temperature (25° C.) and pressure (1 atm). As one of skill in the art would readily recognize, many of the materials disclosed herein can exist in a different phase when subjected to different processing conditions (e.g., different temperatures, different pressures).

In the processes described herein, the processes can further comprise a step of isolating the liquid oligomer product, e.g., from the reaction zone effluent, from the deactivated reaction zone effluent, from the solid polymer product, from the organic reaction medium, etc., using any suitable technique. Additionally or alternatively, the process can further comprise a step of isolating the solid polymer product, e.g., from the reaction zone effluent, the deactivated reaction zone effluent, from the liquid oligomer product, from the organic reaction medium, etc., using any suitable technique. Various suitable separation techniques can be employed, as would be recognized by those of skill in the art. In an embodiment, and not limited thereto, a filtration process, an evaporation process, or a distillation process can be used, as well as combinations of more than one separation technique.

In some embodiments, the process can further comprise a step of separating the solid polymer product—which comprises at least a portion of the catalyst system (or deactivated catalyst system)—e.g., from the reaction zone effluent, the deactivated reaction zone effluent, from the liquid oligomer product, from the organic reaction medium, etc., using any suitable liquid-solid separation technique, such as a filtration process. Additional separation techniques can be employed, if desired.

Advantageously, the solid polymer product, in particular embodiments of this invention, can be insoluble in the organic reaction medium used in the oligomerization process. For instance, the organic reaction medium can be any hydrocarbon organic reaction medium disclosed herein, such as cyclohexane or methylcyclohexane, among others. In further embodiments, and also advantageously, at least a portion of the solid polymer product can comprise particles of the chemically-treated solid oxide.

Advantageously, the oligomerization processes disclosed herein can be performed without reactor fouling, for instance, there is no or substantially no reactor fouling in the reactor, whether a stirred tank reactor, a plug flow reactor, or any combination thereof; or alternatively, a fixed bed reactor, a continuous stirred tank reactor, a loop slurry reactor, a solution reactor, a tubular reactor, a recycle reactor, or any multi-reactor combination thereof. While not wishing to be bound by the following theory, it is believed that the molecular weight of the solid polymer product is such that the polymer produced does not readily adhere to reactor surfaces, and therefore does not cause reactor fouling. The end result can be increased reactor run times and greater production efficiency.

Typically, although not a requirement, the amount of the solid polymer product in the oligomer product (liquid oligomer product+solid polymer product) can fall within a range from 2 to 80 wt. %. In an embodiment, the minimum amount of solid polymer product in the oligomer product can be 2, 5, 10, or 15 wt. %. In an embodiment, the maximum amount of solid polymer product in the oligomer product can be 80, 75, 70, 65, or 60 wt. %. Generally, the amount of solid polymer product in the oligomer product can range from any minimum amount of solid polymer product in the oligomer product described herein to any maximum amount of solid polymer product in the oligomer product. For instance, the amount of the solid polymer product, based on the total weight of the oligomer product, can be from 2 to 65 wt. %, from 2 to 30 wt. %, from 5 to 65 wt. %, from 5 to 30 wt. %, from 10 to 70 wt. %, from 10 to 60 wt. %, from 10 to 40 wt. %, or from 15 to 55 wt. %. Other appropriate amounts of the solid polymer product in the oligomer product are readily apparent from this disclosure.

This invention is also directed to, and encompasses, the liquid oligomer product produced by any of the oligomerization processes disclosed herein. This liquid oligomer product can be characterized, generally, as follows. The liquid oligomer product can contain $C_6$ olefins; alternatively, $C_8$ olefins; or alternatively, $C_6$ and $C_8$ olefins. Based on the weight of the liquid oligomer product, the amount of $C_6$ and/or $C_8$ olefins ($C_6$ olefins, $C_8$ olefins, or total $C_6+C_8$ olefins) typically falls within a range from 70 to 99.9 wt. %, from 80 to 99.9 wt. %, or from 90 to 99.9 wt. %, and more typically falls within a range from 92 to 99.9 wt. %, from 94 to 99.9 wt. %, or from 95 to 99.9 wt. %.

Selectivity to α-olefins in the liquid oligomer product is also unexpectedly high. In an embodiment, the $C_6$ olefins, of a liquid oligomer product comprising at least 10 wt. % $C_6$ olefins, can contain 1-hexene in an amount ranging from 90 to 99.99 mol %, from 95 to 99.99 mol %, from 98 to 99.99 mol %, from 99 to 99.99 mol %, or from 99 to 99.9 mol %. Likewise, in an embodiment, the $C_8$ olefins, of a liquid oligomer product comprising at least 10 wt. % $C_8$ olefins, can contain 1-octene in an amount ranging from 90 to 99.99 mol %, from 95 to 99.99 mol %, from 97 to 99.99 mol %, from 97 to 99.9 mol %, or from 98 to 99.99 mol %.

This invention is also directed to, and encompasses, the solid polymer product produced by any of the processes disclosed herein. This solid polymer product can be characterized by the amount of ethylene in the solid polymer product, the peak molecular weight (Mp) of the solid polymer product, and/or number-average molecular weight (Mn) of the solid polymer product. These features are independently described herein and these independently described features can be used without limitation, and in any combination, to describe the solid polymer product. The solid polymer product contains an ethylene polymer (e.g., ethylene homopolymer, ethylene copolymer, etc.) with at least 90 mol %, or at least 92 mol % ethylene, and more often, at least 95 mol %, at least 98 mol %, or at least 99 mol %, ethylene. In some embodiments, the solid polymer product is essentially an ethylene homopolymer. The solid polymer product typically can have a peak molecular weight (Mp) in a range from 30,000 to 200,000 g/mol, from 35,000 to 180,000 g/mol, from 30,000 to 170,000 g/mol, from 35,000 to 170,000 g/mol, from 40,000 to 200,000 g/mol, from 40,000 to 180,000 g/mol, from 40,000 to 160,000 g/mol, or from 45,000 to 165,000 g/mol. Additionally or alternatively, the solid polymer product can have a number-average molecular weight (Mn) in a range from 5,000 to 30,000 g/mol, from 5,000 to 25,000 g/mol, from 5,000 to 20,000 g/mol, from 7,000 to 25,000 g/mol, from 7,000 to 20,000 g/mol, from 8,000 to 30,000 g/mol, from 8,000 to 25,000 g/mol, or from 8,000 to 20,000 g/mol.

In particular embodiments of this invention, the process can further comprise a step of forming polymer pellets from the solid polymer product. The step of forming polymer pellets can comprise processing the solid polymer product through a pelletizing die (non-limiting examples include strand, underwater, water ring, etc.) using any suitable apparatus. For instance, an extruder, a single screw extruder, a twin screw extruder, a gear pump, or other suitable apparatus can be used.

Articles of manufacture can be formed from, and/or can comprise, the solid polymer product produced in accordance with this invention. Articles which can comprise polymers of this invention include, but are not limited to, an agricultural film, an automobile part, a bottle, a drum, a fiber or fabric, a food packaging film or container, a food service article, a fuel tank, a geomembrane, a household container, a liner, a molded product, a medical device or material, a pipe, a sheet or tape, a toy, and the like. Various processes can be employed to form these articles. Non-limiting examples of these processes include injection molding, blow molding, rotational molding, film extrusion, sheet extrusion, profile extrusion, thermoforming, and the like. Additionally, additives and modifiers are often added to the solid polymer product in order to provide beneficial polymer processing or end-use product attributes. Such processes and materials are described in *Modern Plastics Encyclopedia*, Mid-November 1995 Issue, Vol. 72, No. 12; and *Film Extrusion Manual—Process, Materials, Properties*, TAPPI Press, 1992; the disclosures of which are incorporated herein by reference in their entirety.

Substituent Groups

Various aspects and embodiments described herein may refer to substituted groups or compounds. In an embodiment, each substituent (or non-hydrogen substituent) of any aspect or embodiment calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In an embodiment, each hydrocarbyl substituent can be a $C_1$ to $C_{10}$ hydrocarbyl group, or alternatively, a $C_1$ to $C_5$ hydrocarbyl group. In an embodiment, each hydrocarboxy group or substituent of any aspect or embodiment calling for a group or substituent can be a $C_1$ to $C_{10}$ hydrocarboxy group, or alternatively, a $C_1$ to $C_5$ hydrocarboxy group. In an embodiment, any halide substituent of any aspect or embodiment calling for a substituent can be fluoride, chloride, bromide, or iodide; alternatively, fluoride or chloride. In some embodiments, any halide substituent of any aspect or embodiment calling for a substituent can be fluoride; alternatively, chloride; alternatively, bromide; or alternatively, iodide.

In an embodiment, any hydrocarbyl substituent of any aspect or embodiment calling for a substituent can be an alkyl group, an aryl group, or an aralkyl group; alternatively, an alkyl group; alternatively, an aryl group; or alternatively, an aralkyl group. In an embodiment, any alkyl substituent of any aspect or embodiment calling for a substituent can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl substituent of any aspect or embodiment calling for a substituent can be a phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, any aralkyl substituent of any aspect or embodiment calling for a substituent can be benzyl group or an ethylphenyl group (2-phenyleth-1-yl or 1-phenyleth-1-yl); alternatively, a benzyl group; alternatively, an ethylphenyl group; alternatively a 2-phenyleth-1-yl group; or alternatively, a 1-phenyleth-1-yl group.

In an embodiment, any hydrocarboxy substituent of any aspect or embodiment calling for a substituent can be an alkoxy group, an aryloxy group, or an aralkoxy group; alternatively, an alkoxy group; alternatively, an aryloxy group or an aralkoxy group. In an embodiment, any alkoxy substituent of any aspect or embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryloxy substituent of any aspect or embodiment calling for a substituent can be a phenoxy group, a toloxy group, a xyloxy group, or a 2,4,6-trimethylphenoxy group; alternatively, a phenoxy group; alternatively, a toloxy group; alternatively, a xyloxy group; or alternatively, a 2,4,6-trimethylphenoxy group. In an embodiment, any aralkoxy substituent of any aspect or embodiment calling for a substituent can be a benzoxy group.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Fluorided silica-coated alumina chemically-treated solid oxides were prepared as follows. Bohemite was obtained from W.R. Grace & Company under the designation "Alumina A" and having a surface area of 300 $m^2/g$, a pore volume of 1.3 mL/g, and an average particle size of 100 microns. The alumina was first calcined in dry air at 600° C. for 6 hours, cooled to ambient temperature, and then contacted with tetraethylorthosilicate in isopropanol to equal 25 wt. % $SiO_2$. After drying, the silica-coated alumina was calcined at 600° C. for 3 hours. Fluorided silica-coated alumina (7 wt. % F) was prepared by impregnating the calcined silica-coated alumina with an ammonium bifluoride solution in methanol, drying, and then calcining for 3 hours at 600° C. in dry air. Afterward, the fluorided silica-coated alumina (FSCA) was collected and stored under dry nitrogen, and was used without exposure to the atmosphere.

Sulfated alumina chemically-treated solid oxides were prepared as follows from the same base alumina grade used to produce FSCA. The base alumina material was impregnated to incipient wetness with an aqueous solution of ammonium sulfate to equal 15% sulfate. This mixture was then placed in a flat pan and allowed to dry under vacuum at approximately 110° C. for 16 hours. To calcine the resultant powdered mixture, the material was fluidized in a stream of dry air at 550° C. for 6 hours. Afterward, the sulfated alumina (SA) was collected and stored under dry nitrogen, and was used without exposure to the atmosphere.

TMA was obtained from Sigma-Aldrich as a 2 molar solution in heptane and utilized as received. TEA was obtained from Sigma-Aldrich (≥22.5 wt. % aluminum) and utilized as received. TIBA was obtained from AkzoNobel (≥13.4 wt. % aluminum) and utilized as received. TNOA was obtained from AkzoNobel (≥7.0 wt. % aluminum) and utilized as received. MMAO-3A was obtained from AkzoNobel (7 wt. % aluminum) and utilized as received.

The base material for the silica used in Examples 17-18 had a surface area of 300 $m^2/g$, a pore volume of 1.6 mL/g, and an average particle size of 100 microns. This material was calcined in nitrogen at 600° C. for 3 hours, cooled to ambient temperature, and then the silica was stored under dry nitrogen and used without exposure to the atmosphere.

Solvents/diluent utilized in the examples were sparged with nitrogen prior to use and stored over 13× sieves glovebox having a nitrogen atmosphere. All catalyst system activations were carried out in the glovebox having a nitrogen atmosphere.

Each example provided herein utilized either heteroatomic chromium chloride complex A or heteroatomic chromium chloride complex B:

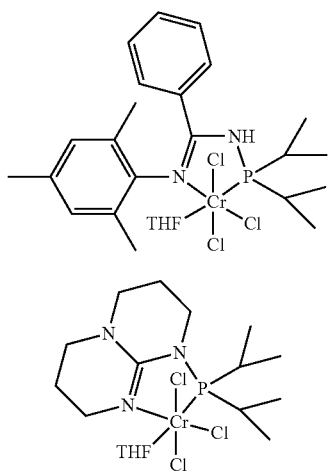

Complex A

Complex B

In Activation Method A, the heteroatomic ligand chromium compound complex in ethylbenzene (EB) was mixed with either triethylaluminum (TEA) or trimethylaluminum (TMA) for 30 minutes. No aluminoxane or chemically-treated solid oxide was present.

In Activation Method B, the heteroatomic ligand chromium compound complex in ethylbenzene (EB) was combined first with the support or chemically-treated solid oxide (e.g., silica, SA, Bohemite, FSCA) for 30 minutes to form a mixture. TEA then was added to the mixture, and the catalyst system was stirred for 30 minutes.

In Activation Method C, TEA or triisobutylaluminum (TIBA) was first combined with the support or chemically-treated solid oxide (e.g., silica, SA, Bohemite, FSCA) in cyclohexane (CyH) and stirred for 30 minutes to form a precontacted mixture, then the precontacted mixture was combined with the heteroatomic ligand chromium compound complex in ethylbenzene (EB) and stirred for 30 minutes.

In Activation Method D, an alkylaluminum compound (TEA, TMA, TIBA, or TNOA) was first combined with the heteroatomic ligand chromium compound complex in ethylbenzene (EB) and stirred for 30 minutes to form a precontacted mixture, then the mixture was combined with the support or chemically-treated solid oxide (e.g., silica, SA, Bohemite, FSCA) in CyH and stirred for 30 or 60 minutes.

In Activation Method E, an alkylaluminum (TEA, TMA, or TNOA) was combined with the heteroatomic ligand chromium compound complex in ethylbenzene (EB) and stirred for 30 minutes to form a first mixture. An alkylaluminum (TEA, TMA, or TNOA) in cyclohexane (CyH) was combined with the support or chemically-treated solid oxide (e.g., silica, SA, Bohemite, or FSCA) and stirred for 30 minutes to form a second mixture. Then, the first mixture and the second mixture were combined and stirred for 30 minutes.

In Activation Method F, a modified methyl aluminoxane (MMAO-3A) was combined with the heteroatomic ligand chromium compound complex in ethylbenzene (EB).

In Activation Method G, the heteroatomic ligand chromium compound complex and TEA were simultaneously added to the support or chemically-treated solid oxide (e.g., silica, SA, Bohemite, FSCA) in CyH and stirred for 30 minutes.

In Activation Method H, MMAO-3A was first combined with the support or chemically-treated solid oxide (e.g., silica, SA, Bohemite, FSCA) in cyclohexane (CyH) and stirred for 10 minutes to form a precontacted mixture, then the precontacted mixture was combined with the heteroatomic ligand chromium compound complex in ethylbenzene (EB) and stirred for 30 minutes.

Molecular weights and molecular weight distributions were obtained using a PL-GPC 220 (Polymer Labs, an Agilent Company) system equipped with a IR4 detector (Polymer Char, Spain) and three Styragel™ HMW-6E GPC columns (Waters, Mass.) running at 145° C. The flow rate of the mobile phase 1,2,4-trichlorobenzene (TCB) containing 0.5 g/L 2,6-di-t-butyl-4-methylphenol (BHT) was set at 1 mL/min, and polymer solution concentrations were in the range of 1.0-1.5 mg/mL, depending on the molecular weight. Sample preparation was conducted at 150° C. for nominally 4 hours with occasional and gentle agitation, before the solutions were transferred to sample vials for injection. An injection volume of about 200 µL was used. The integral calibration method was used to deduce molecular weights and molecular weight distributions using a Chevron Phillips Chemical Company's HDPE polyethylene resin, MARLEX® BHB5003, as the standard. The integral table of the standard was pre-determined in a separate experiment with SEC-MALS. Mp is the peak molecular weight, Mn is the number-average molecular weight, Mw is the weight-average molecular weight, and Mz is the z-average molecular weight.

Polymer C-13 NMR sample preparation and data collection were performed as follows. A 0.55 gram sample of the solid polymer sample, 1.20 g of 1,4-dichlorobenzene-d4 (98% D) and 2.5 mL of 1,2,4-trichlorobenzene (distilled and dosed with 0.034 wt. % butylated hydroxytoluene) were charged to a 10 mm NMR tube. The 10 mm NMR tube containing the polymer sample mixture was then heated in a heating block at 128° C. with occasional stirring using a stainless steel stirrer to ensure homogeneous mixing of polymer sample into solution. The sample was then left in the heating block at 112° C. for 16 hours to ensure complete disentanglement of polymer chains. The final concentration of the polymer in the C-13 NMR sample was ~10 wt. %. The C13 NMR analysis was then performed using a 500 MHz Oxford Magnet. Data collection and processing were performed using a Bruker 10 mm BBO probe and Advance III HD console using the following data collection parameters:

| F2 - Acquisition Parameters | |
|---|---:|
| INSTRUM | spect |
| PROBHD | 10 mm PABBO BB |
| PULPROG | zgdc |
| TD | 49018 |
| SOLVENT | C6D6 |
| NS | 6489 |

-continued

| | |
|---|---|
| DS | 8 |
| SWH | 8169.935 Hz |
| FIDRES | 0.166672 Hz |
| AQ | 2.9999015 sec |
| RG | 35.5 |
| DW | 61.200 usec |
| DE | 6.50 usec |
| TE | 398.1 K |
| D1 | 7.00000000 sec |
| D11 | 0.03000000 sec |
| TDO | 12 |
| ========= CHANNEL f1 ========= | |
| SFO1 | 125.6986968 MHz |
| NUC1 | 13C |
| P1 | 15.00 usec |
| PLW1 | 63.00000000 W |
| ========= CHANNEL f2 ========= | |
| SFO2 | 499.8814996 MHz |
| NUC2 | 1H |
| CPDPRG[2 | waltz65 |
| PCPD2 | 80.00 usec |
| PLW2 | 25.00000000 W |
| PLW12 | 1.76390004 W |
| F2 - Processing parameters | |
| SI | 131072 |
| SF | 125.6948915 MHz |
| WDW | EM |
| SSB | 0 |
| LB | 1.00 Hz |
| GB | 0 |
| PC | 4.00 |

Ethylene oligomerizations were performed as follows. Cyclohexane, 200 mL, was added to an activated catalyst system that was activated according to one of the activation methods A-H. The activated catalyst system mixture was the charged to an evacuated autoclave reactor (0.5 L stainless steel ZipperClave® Autoclave) held at 60° C. The reactor was then charged with 50 psig $H_2$ and 875 psig ethylene. Stirring of the autoclave reactor content was started by activating an air driven autoclave stirrer motor. The autoclave reactor contents were then allowed to reach the desired reaction temperature and the reaction temperature was maintained by use of internal cooling coils and if necessary an external water bath. As the reaction proceeded, ethylene was fed to the reactor on demand to maintain the autoclave reactor pressure for the desired reaction time. At reaction completion, water cooling was applied to the autoclave reactor. When the autoclave reactor contents temperature reached 35° C., the unreacted ethylene and hydrogen gas were vented from the reactor. A liquid sample (~2 mL) of the reactor contents was then collected, filtered, and analyzed by GC-FID. The reactor solids were collected by filtering the reaction mixture and cleaning the reactor walls and cooling coil.

The liquid reactor content samples were analyzed on an Agilent 7890-LTM equipped with an Agilent DB-5msUI column (Agilent P/N 222-5532UILTM) with a 30 m length, 0.25 ID, and 0.25 μm film thickness and a flame ionization detector.

Table 3 summarizes the catalyst systems, oligomerization conditions, oligomer product properties, and catalyst productivities for Examples 1-45. As shown in Table 3, Examples 1-2 did not utilize an aluminoxane or chemically-treated solid oxide activator, and these catalyst systems had low productivity of the $C_6+C_8$ product. Likewise, Examples 17-18 and 32 utilized a solid oxide that was not chemically-treated, and this also resulted in low productivity of the $C_6+C_8$ product.

For Examples 3-16, 19-22, and 30-31 (using Complex A), it was unexpectedly found that the method of catalyst preparation and catalyst activation had an impact on the amount of oligomer product produced (liquid NAO product+polymer product). Pre-contacting or pre-mixing the chemically-treated solid oxide and the organoaluminum compound (before adding in the heteroatomic ligand transition metal compound complex), and pre-contacting or pre-mixing the heteroatomic ligand transition metal compound complex and the organoaluminum (before adding in the chemically-treated solid oxide) both resulted in improved productivity. Additionally, the combination of these two pre-contacting or pre-mixing steps—i.e., pre-contacting or pre-mixing the chemically-treated solid oxide and a first organoaluminum compound to form a first mixture; pre-contacting or pre-mixing the heteroatomic ligand transition metal compound complex and a second organoaluminum compound to form a second mixture; and then combining the first mixture with the second mixture to form the catalyst system—also resulted in significantly improved catalyst productivities.

As shown by Examples 3-16, 19-22, and 30-31 (using Complex A) in Table 3, the catalyst systems containing a chemically-treated solid oxide were very efficient in oligomerizing ethylene to produce $C_6+C_8$ oligomer product. Surprisingly high catalyst system productivities were achieved, generally ranging from 40,000 to 380,000 grams of $C_6+C_8$ product per gram of chromium. Of the liquid oligomer product, the wt. % of total $C_6+C_8$ products ranged from 97.5 to 99.3 wt. %, and the wt. % of $C_6$ olefins ranged from 95.8 to 97.3 wt. %. Selectivity to α-olefins was also extremely high: the $C_6$ oligomer product contained from 99.2 to 99.7 mol % 1-hexene, and the $C_8$ oligomer product contained from 89 to 99.4 mol % 1-octene (and mostly in the 97 to 99.4 mol % range).

Interestingly, particularly as compared to Examples 23-27 that utilized an alumoxane activator and produced less than 1 wt. % polymer, the catalyst systems containing a chemically-treated solid oxide (Examples 3-16, 19-22, and 30-31) produced increased amounts of a solid polymer product, generally ranging from 15 to 57 wt. %, based on the total weight of the oligomer product. Catalyst system productivities for producing the solid polymer product—for Examples 3-16, 19-22, and 30-31—ranged from 14,000 to 167,000 grams of polymer product per gram of chromium.

As shown by Examples 33-45 (using Complex B) in Table 3, the catalyst systems containing a chemically-treated solid oxide were very efficient in oligomerizing ethylene to produce $C_6+C_8$ oligomer product. Surprisingly high catalyst system productivities were achieved, generally ranging from 46,000 to 112,000 grams of $C_6+C_8$ product per gram of chromium (excluding Example 40). Of the liquid oligomer product, the wt. % of total $C_6+C_8$ products ranged from 96.5 to 98 wt. %, and the wt. % of $C_6$ olefins ranged from 73.5 to 79.4 wt. %. Selectivity to α-olefins was also extremely high: the $C_6$ oligomer product contained from 92.5 to 96.3 mol % 1-hexene, and the $C_8$ oligomer product contained from 93.3 to 97.7 mol % 1-octene.

Examples 33-45 produced amounts of a solid polymer product generally ranging from 20 to 70 wt. %, based on the total weight of the oligomer product. Catalyst system productivities for producing the solid polymer product—for Examples 33-45—ranged from 12,000 to 61,000 grams of polymer product per gram of chromium.

Examples 28-29 utilized an aluminoxane instead of a trialkylaluminum compound, such as TEA or TIBA. These examples demonstrate that aluminoxanes can be used as organoaluminum compounds in catalyst systems containing a chemically-treated solid oxide.

Figure 2:
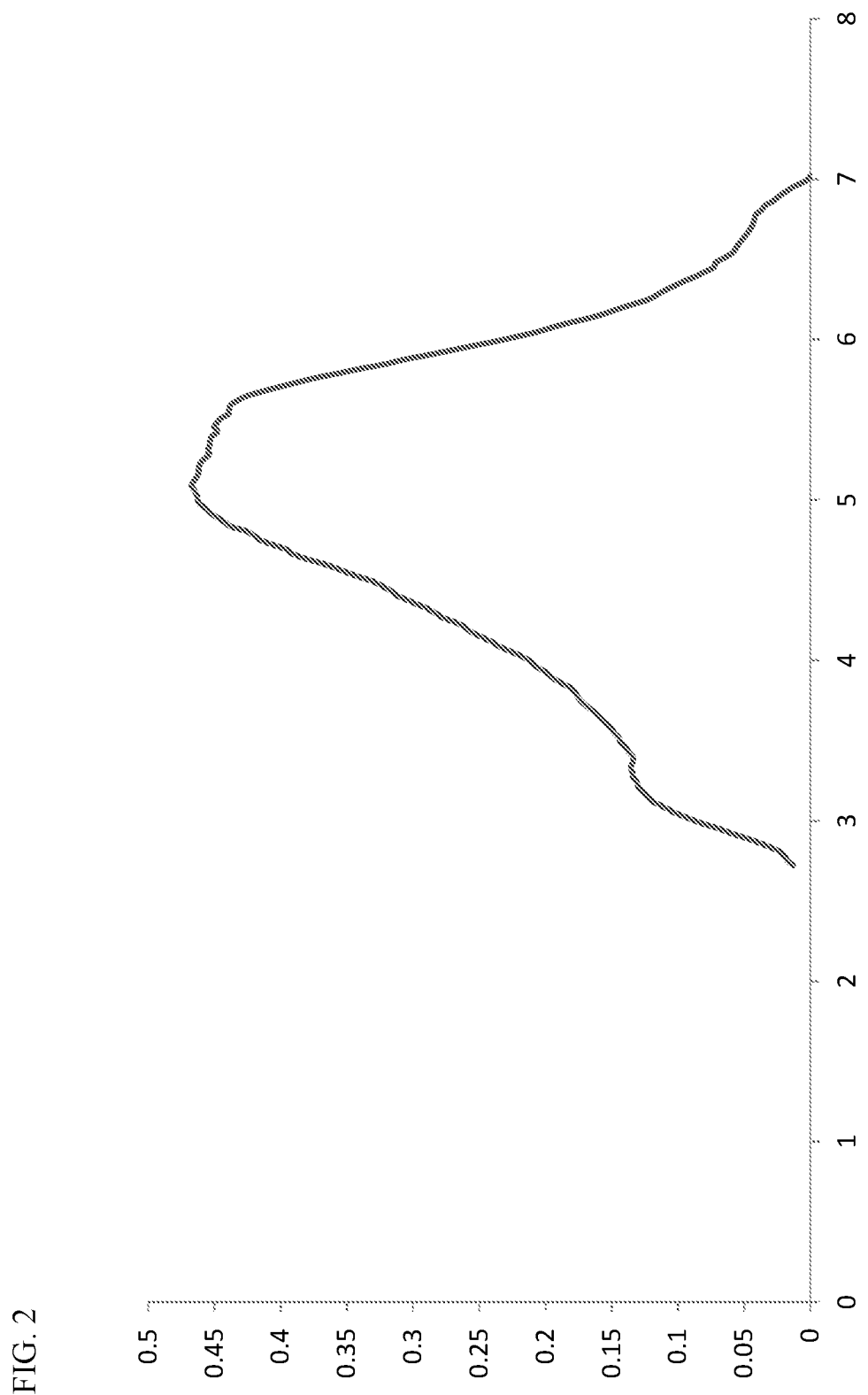
FIG. 2 presents a plot of the molecular weight distribution of the polymer product of Example 37, representative of polymer products produced using a catalyst system containing heteroatomic ligand transition metal compound complex B, a chemically-treated solid oxide, and an organoaluminum compound.
Figure 3:
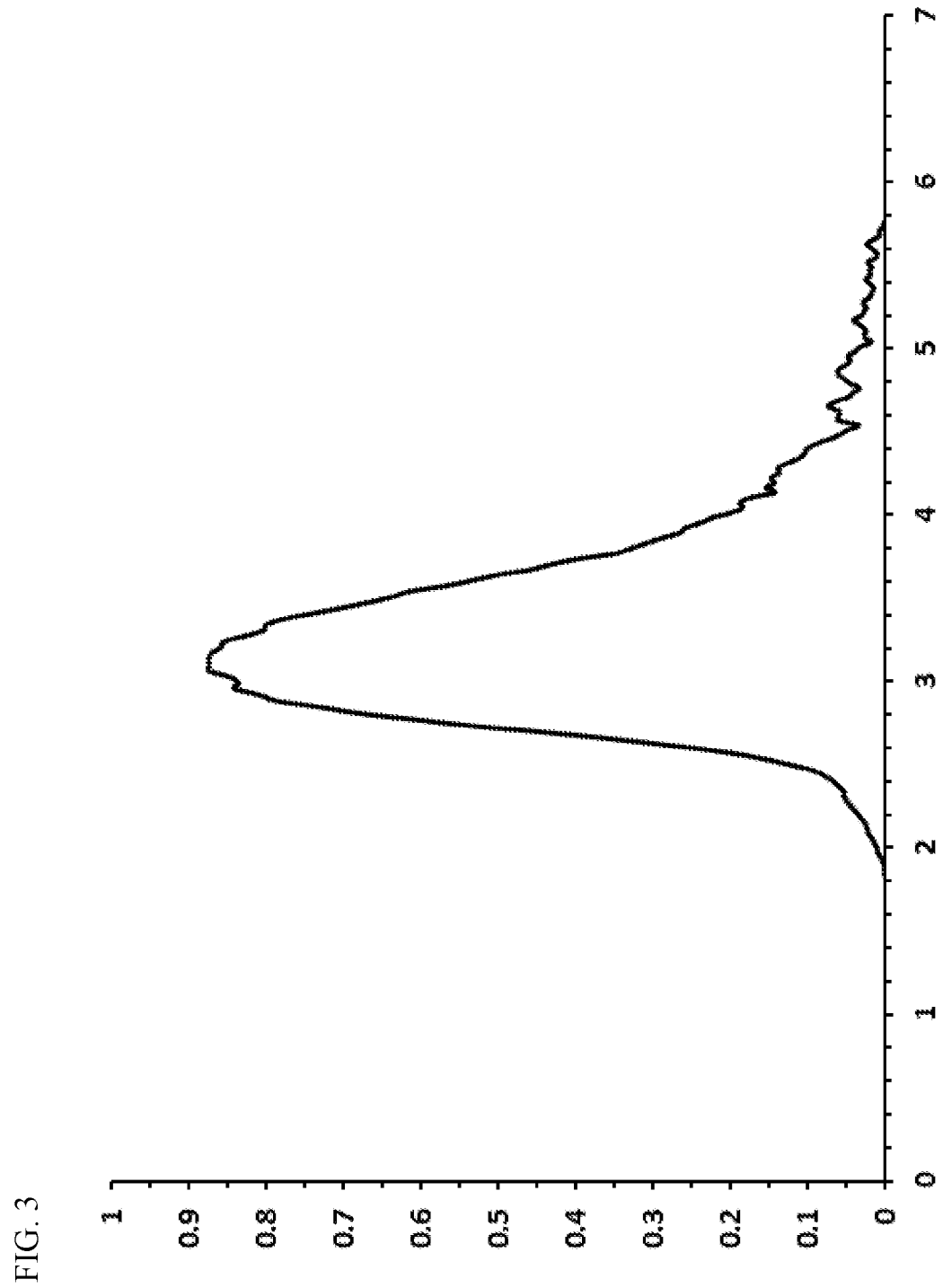
FIG. 3 presents a plot of the molecular weight distribution of a polymer product representative of polymer products produced using a homogeneous catalyst system containing a $N^2$-phosphinyl amidine transition metal compound complex and MMAO-3A modified methylaluminoxane.

Table 4 summarizes the molecular weight characterization of the solid polymer produced in some of the examples in Table 3. For catalyst systems using a chemically-treated solid oxide, relatively high molecular weight polymer was produced, with Mn's ranging from 10,000 to 17,000 g/mol, Mp's ranging from 51,000 to 145,000 g/mol, Mw's ranging from 158,000 to 369,000 g/mol, and Mz's ranging from 939,000 to 2,233,000 g/mol. FIG. 1 and FIG. 2 illustrate the molecular weight distributions (amount of polymer versus logarithm of molecular weight) for the ethylene polymers of Example 10 and Examples 37, respectively, demonstrating the high molecular weight produced using the catalyst systems described herein. In contrast, FIG. 3 illustrates the molecular weight distribution (amount of polymer versus logarithm of molecular weight) for a polymer product produced using a homogeneous catalyst system containing a $N^2$-phosphinyl amidine transition metal compound complex and MMAO-3A modified methylaluminoxane (see e.g., U.S. Pat. No. 8,680,003), demonstrating that only very low molecular weight polymer (Mp of 1,000-2,000 g/mol) was produced with MAO-based catalyst systems (in the absence of a chemically-treated solid oxide). Furthermore, no reactor fouling was noted during any of the oligomerization experiments of Examples 3-16, 19-22, 30-31, and 33-45, which utilized catalyst systems containing a chemically-treated solid oxide.

Table 5 present NMR data that demonstrates the high molecular weight polymer product produced with catalyst systems using a chemically-treated solid oxide was predominantly ethylene homopolymer (>99 mol % ethylene), with very little comonomer side chains.

TABLE 3

| Example | 1 | 2 | 3 | 4 | 5 | 6 |
|---|---|---|---|---|---|---|
| Catalyst System | | | | | | |
| Activation Method | A | A | B | C | C | C |
| Complex | A | A | A | A | A | A |
| mmol complex | 0.0060 | 0.0060 | 0.0060 | 0.0060 | 0.0060 | 0.0060 |
| Complex Alkylaluminum | — | — | — | — | — | — |
| Complex Alkylaluminum Mass (mg) | — | — | — | — | — | — |
| Support | — | — | FSCA | FSCA | FSCA | FSCA |
| Support Mass (mg) | — | — | 350 | 350 | 350 | 350 |
| Support Alkylaluminum | — | — | — | TEA | TIBA | TIBA |
| Support Alkylaluminum (mg) | — | — | — | 75 | 40 | 80 |
| Free Alkylaluminum (g) | TEA | TMA | TEA | — | — | — |
| Free Alkylaluminum Mass (mg) | 40 | 40 | 40 | — | — | — |
| Total Alkylaluminum (mg) | 40 | 40 | 40 | 75 | 40 | 80 |
| Catalyst System Al:Cr molar ratio | 59 | 89 | 59 | 110 | 34 | 68 |
| Catalyst Solvent | EB | EB | EB | EB | EB | EB |
| Solvent Mass (g) | 1 | 1 | 1 | 1.02 | 1 | 1 |
| Activation Time (hours) | 0.5 | 0.5 | 0.5 | 0.5 | 0.5 | 0.5 |
| Oligomerization Conditions | | | | | | |
| Diluent | CyH | CyH | CyH | CyH | CyH | CyH |
| Diluent Volume (mL) | 200 | 200 | 200 | 200 | 200 | 200 |
| Ethylene Pressure (psig) | 875 | 875 | 875 | 875 | 875 | 875 |
| Hydrogen Pressure (psig) | 50 | 50 | 50 | 50 | 50 | 50 |
| Time (min) | 20 | 20 | 20 | 20 | 20 | 20 |
| Temperature (° C.) | 70 | 70 | 70 | 70 | 70 | 70 |
| Oligomer Product | | | | | | |
| g liquid NAO product | 4 | 3 | 49 | 66 | 39 | 51 |
| g polymer | 1.32 | 0 | 35.4 | 37.5 | 52 | 43.5 |
| polymer (mass %) | 24.43% | 0.00% | 41.76% | 36.14% | 57.13% | 45.86% |
| C # dist data (mass %) | | | | | | |
| $C_6$ | 97.0 | 97.4 | 97.3 | 96.5 | 96.3 | 95.8 |
| $C_8$ | 1.0 | 0.9 | 1.5 | 1.8 | 2.2 | 1.8 |
| $C_{10}$ | 1.9 | 1.7 | 1.2 | 1.5 | 1.3 | 2.1 |
| $C_{12}$ | 0.0 | 0.0 | 0.0 | 0.1 | 0.2 | 0.3 |
| $C_{14+}$ | 0.0 | 0.0 | 0.0 | 0.0 | 0.0 | 0.0 |
| ($C_6 + C_8$) (mass %) | 98.1 | 98.3 | 98.8 | 98.3 | 98.5 | 97.6 |
| $C_6$ Purity(mol % 1-hexene) | 98.47 | 98.94 | 99.68 | 99.63 | 99.69 | 99.71 |
| $C_8$ Purity (mol % 1-octene) | 58.60 | 100 | 97.46 | 97.73 | 97.14 | 98.03 |
| Methylcyclopentane (mass %) | 0.35 | 0.97 | 0.05 | 0.06 | 0.10 | 0.06 |
| Methylenecyclopentane (mass %) | 0.00 | 0.00 | 0.03 | 0.03 | 0.05 | 0.03 |
| Productivities | | | | | | |
| (g Liquid Product)/(mMol Chromium) | 682 | 456 | 8,252 | 11,073 | 6,520 | 8,582 |
| [g ($C_6 + C_8$)]/(g Cr) | 12,873 | 8,619 | 156,785 | 209,432 | 123,544 | 161,109 |
| [g ($C_6 + C_8$)]/(g Cr)/hr | 38,619 | 25,857 | 470,355 | 628,295 | 370,633 | 483,327 |
| [g ($C_6 + C_8$)]/(g Aluminum) | 423 | 179 | 5155 | 3671 | 7064 | 4606 |
| (g polymer)/(g product) | 0.323 | 0 | 0.717 | 0.566 | 1.33 | 0.847 |
| (g polymer)/(g Chromium) | 4,242 | 0 | 113,766 | 120,515 | 167,114 | 139,798 |

TABLE 3-continued

| Example | 7 | 8 | 9 | 10 | | |
|---|---|---|---|---|---|---|
| Catalyst System | | | | | | |
| Activation Method | D | D | D | D | | |
| Complex # | A | A | A | A | | |
| mmol complex | 0.0060 | 0.0060 | 0.0060 | 0.0060 | | |
| Complex Alkylaluminum | TEA | TMA | TMA | TMA | | |
| Complex Alkylaluminum Mass (mg) | 40 | 21.6 | 10.8 | 5.5 | | |
| Support | FSCA | FSCA | FSCA | FSCA | | |
| Support Mass (mg) | 350 | 350 | 350 | 350 | | |
| Support Alkylaluminum | — | — | — | — | | |
| Support Alkylaluminum (mg) | — | — | — | — | | |
| Free Alkylaluminum (g) | — | — | — | — | | |
| Free Alkylaluminum Mass (mg) | — | — | — | — | | |
| Total Alkylaluminum (mg) | 40 | 21.6 | 10.8 | 5.5 | | |
| Catalyst System Al:Cr molar ratio | 59 | 47 | 23 | 12 | | |
| Catalyst Solvent | EB | EB | EB | EB | | |
| Solvent Mass (g) | 1 | 1 | 1 | 1 | | |
| Activation Time (hours) | 0.5 | 0.5 | 0.5 | 0.5 | | |
| Oligomerization Conditions | | | | | | |
| Diluent | CyH | CyH | CyH | CyH | | |
| Diluent Volume (mL) | 200 | 200 | 200 | 200 | | |
| Ethylene Pressure (psig) | 875 | 875 | 875 | 875 | | |
| Hydrogen Pressure (psig) | 50 | 50 | 50 | 50 | | |
| Time (min) | 20 | 20 | 20 | 20 | | |
| Temperature (° C.) | 70 | 70 | 70 | 70 | | |
| Oligomer Product | | | | | | |
| g liquid NAO product | 111 | 25 | 71 | 62 | | |
| g polymer | 46.6 | 7.37 | 26.5 | 23.5 | | |
| polymer (mass%) | 29.48% | 22.53% | 27.18% | 27.52% | | |
| C # dist data (mass %) | | | | | | |
| $C_6$ | 96.4 | 96.2 | 96.4 | 96.8 | | |
| $C_8$ | 1.2 | 1.8 | 1.9 | 1.8 | | |
| $C_{10}$ | 2.3 | 2.0 | 1.3 | 1.3 | | |
| $C_{12}$ | 0.0 | 0.0 | 0.4 | 0.1 | | |
| $C_{14+}$ | 0.0 | 0.0 | 0.0 | 0.0 | | |
| ($C_6 + C_8$) (mass %) | 97.7 | 98.0 | 98.3 | 98.6 | | |
| $C_6$ Purity(mol % 1-hexene) | 99.62 | 99.61 | 99.57 | 99.61 | | |
| $C_8$ Purity (mol % 1-octene) | 98.80 | 99.35 | 99.33 | 98.52 | | |
| Methylcyclopentane (mass %) | 0.04 | 0.12 | 0.07 | 0.06 | | |
| Methylenecyclopentane (mass %) | 0.02 | 0.03 | 0.03 | 0.04 | | |
| Productivities | | | | | | |
| (g Liquid Product)/(mMol Chromium) | 18,631 | 4,234 | 11,864 | 10,343 | | |
| [g ($C_6 + C_8$)]/(g Cr) | 349,914 | 79,788 | 224,168 | 196,115 | | |
| [g ($C_6 + C_8$)]/(g Cr)/hr | 1,049,742 | 239,365 | 672,504 | 588,344 | | |
| [g ($C_6 + C_8$)]/(g Aluminum) | 11501 | 3071 | 17236 | 29761 | | |
| (g polymer)/(g product) | 0.418 | 0.291 | 0.373 | 0.380 | | |
| (g polymer)/(g Chromium) | 149,760 | 23,685 | 85,164 | 75,523 | | |
| Example | 11 | 12 | 13 | 14 | 15 | 16 |
| Catalyst System | | | | | | |
| Activation Method | E | E | E | E | E | E |
| Complex # | A | A | A | A | A | A |
| mmol complex | 0.0060 | 0.0060 | 0.0060 | 0.0060 | 0.0060 | 0.0060 |
| Complex Alkylaluminum | TEA | TEA | TEA | TEA | TEA | TEA |
| Complex Alkylaluminum Mass (mg) | 40 | 40 | 40 | 40 | 40 | 40 |
| Support | FSCA | FSCA | FSCA | SA | SA | SA |
| Support Mass (mg) | 350 | 350 | 350 | 350 | 350 | 350 |
| Support Alkylaluminum | TEA | TEA | TEA | TEA | TEA | TEA |
| Support Alkylaluminum (mg) | 35 | 70 | 25 | 35 | 70 | 25 |
| Free Alkylaluminum (g) | — | — | — | — | — | — |
| Free Alkylaluminum Mass (mg) | — | — | — | — | — | — |
| Total Alkylaluminum (mg) | 75 | 110 | 65 | 75 | 110 | 65 |
| Catalyst System Al:Cr molar ratio | 110 | 161 | 95 | 110 | 161 | 95 |
| Catalyst Solvent | EB | EB | EB | EB | EB | EB |
| Solvent Mass (g) | 1 | 1 | 1 | 1 | 1 | 1 |
| Activation Time (hours) | 0.5 | 0.5 | 0.5 | 0.5 | 0.5 | 0.5 |
| Oligomerization Conditions | | | | | | |
| Diluent | CyH | CyH | CyH | CyH | CyH | CyH |
| Diluent Volume (mL) | 200 | 200 | 200 | 200 | 200 | 200 |
| Ethylene Pressure (psig) | 875 | 875 | 875 | 875 | 875 | 875 |
| Hydrogen Pressure (psig) | 50 | 50 | 50 | 50 | 50 | 50 |

TABLE 3-continued

| | | | | | | |
|---|---|---|---|---|---|---|
| Time (min) | 20 | 20 | 20 | 20 | 20 | 20 |
| Temperature (° C.) | 70 | 70 | 70 | 70 | 70 | 70 |
| *Oligomer Product* | | | | | | |
| g liquid NAO product | 121 | 115 | 109 | 16 | 14 | 17 |
| g polymer | 34.5 | 32.9 | 35.5 | 21.4 | 16.1 | 21.1 |
| polymer (mass%) | 22.24% | 22.22% | 24.63% | 57.41% | 53.65% | 55.77% |
| C # dist data (mass %) | | | | | | |
| $C_6$ | 96.3 | 96.3 | 96.3 | 96.8 | 96.9 | 96.9 |
| $C_8$ | 1.2 | 1.3 | 1.2 | 1.4 | 1.4 | 1.4 |
| $C_{10}$ | 2.5 | 2.2 | 2.4 | 1.5 | 1.5 | 1.5 |
| $C_{12}$ | 0.1 | 0.2 | 0.1 | 0.3 | 0.2 | 0.2 |
| $C_{14+}$ | 0.0 | 0.0 | 0.0 | 0.0 | 0.0 | 0.0 |
| ($C_6 + C_8$) (mass %) | 97.5 | 97.6 | 97.5 | 98.2 | 98.3 | 98.3 |
| $C_6$ Purity(mol % 1-hexene) | 99.65 | 99.66 | 99.65 | 99.28 | 99.36 | 99.44 |
| $C_8$ Purity (mol % 1-octene) | 97.03 | 97.70 | 97.83 | 94.81 | 89.78 | 92.24 |
| Methylcyclopentane (mass %) | 0.04 | 0.05 | 0.05 | 0.14 | 0.14 | 0.12 |
| Methylenecyclopentane (mass %) | 0.02 | 0.03 | 0.02 | 0.05 | 0.03 | 0.03 |
| *Productivities* | | | | | | |
| (g Liquid Product)/(mMol Chromium) | 20,163 | 19,242 | 18,157 | 2,653 | 2,325 | 2,796 |
| [g ($C_6 + C_8$)]/(g Cr) | 377,876 | 361,073 | 340,508 | 50,121 | 43,937 | 52,889 |
| [g ($C_6 + C_8$)]/(g Cr)/hr | 1,133,628 | 1,083,219 | 1,021,524 | 150,364 | 131,811 | 158,667 |
| [g ($C_6 + C_8$)]/(g Aluminum) | 6624 | 4316 | 6888 | 879 | 525 | 1070 |
| (g polymer)/(g product) | 0.286 | 0.286 | 0.327 | 1.35 | 1.16 | 1.26 |
| (g polymer)/(g Chromium) | 110,874 | 105,732 | 114,088 | 68,774 | 51,741 | 67,810 |

| Example | 17 | 18 | 19 | 20 | 21 | 22 |
|---|---|---|---|---|---|---|
| *Catalyst System* | | | | | | |
| Activation Method | E | E | E | E | E | E |
| Complex # | A | A | A | A | A | A |
| mmol complex | 0.0060 | 0.0060 | 0.0060 | 0.0060 | 0.0060 | 0.0060 |
| Complex Alkylaluminum | TEA | TEA | TMA | TMA | TMA | TIBA |
| Complex Alkylaluminum Mass (mg) | 40 | 40 | 10.8 | 5.5 | 5.5 | 12 |
| Support | Silica | Silica | FSCA | FSCA | FSCA | FSCA |
| Support Mass (mg) | 350 | 350 | 350 | 350 | 350 | 350 |
| Support Alkylaluminum | TEA | TEA | TMA | TMA | TMA | TIBA |
| Support Alkylaluminum (mg) | 35 | 70 | 33.2 | 10.8 | 21.6 | 35 |
| Free Alkylaluminum (g) | — | — | — | — | — | — |
| Free Alkylaluminum Mass (mg) | — | — | — | — | — | — |
| Total Alkylaluminum (mg) | 75 | 110 | 44 | 16.3 | 27.1 | 47 |
| Catalyst System Al:Cr molar ratio | 110 | 161 | 95 | 35 | 59 | 31 |
| Catalyst Solvent | EB | EB | EB | EB | EB | EB |
| Solvent Mass (g) | 1 | 1 | 1 | 1 | 1 | 1 |
| Activation Time (hours) | 0.5 | 0.5 | 0.5 | 0.5 | 0.5 | 0.5 |
| *Oligomerization Conditions* | | | | | | |
| Diluent | CyH | CyH | CyH | CyH | CyH | CyH |
| Diluent Volume (mL) | 200 | 200 | 200 | 200 | 200 | 200 |
| Ethylene Pressure (psig) | 875 | 875 | 875 | 875 | 875 | 875 |
| Hydrogen Pressure (psig) | 50 | 50 | 50 | 50 | 50 | 50 |
| Time (min) | 20 | 20 | 20 | 20 | 20 | 20 |
| Temperature (° C.) | 70 | 70 | 70 | 70 | 70 | 70 |
| *Oligomer Product* | | | | | | |
| g liquid NAO product | 3 | 1 | 30 | 33 | 19 | 95 |
| g polymer | 5.14 | 2.78 | 5.73 | 12.04 | 4.54 | 40.7 |
| polymer (mass %) | 61.86% | 67.01% | 15.90% | 26.74% | 19.57% | 30.10% |
| C # dist data (mass %) | | | | | | |
| $C_6$ | 95.9 | 93.7 | 97.2 | 97.1 | 97.1 | 96.7 |
| $C_8$ | 2.1 | 3.5 | 1.9 | 1.8 | 2.2 | 1.3 |
| $C_{10}$ | 2.0 | 2.8 | 0.9 | 1.0 | 0.7 | 1.9 |
| $C_{12}$ | 0.0 | 0.0 | 0.0 | 0.2 | 0.0 | 0.1 |
| $C_{14+}$ | 0.0 | 0.0 | 0.0 | 0.0 | 0.0 | 0.0 |
| ($C_6 + C_8$) (mass %) | 98.0 | 97.2 | 99.1 | 98.9 | 99.3 | 98.0 |
| $C_6$ Purity(mol % 1-hexene) | 98.76 | 97.11 | 99.56 | 99.58 | 99.54 | 99.55 |
| $C_8$ Purity (mol % 1-octene) | 86.10 | 53.70 | 98.01 | 98.86 | 98.34 | 97.78 |
| Methylcyclopentane (mass %) | 0.51 | 0.58 | 0.10 | 0.08 | 0.11 | 0.05 |
| Methylenecyclopentane (mass %) | 0.00 | 0.00 | 0.03 | 0.03 | 0.04 | 0.02 |

TABLE 3-continued

| Productivities | | | | | | |
|---|---|---|---|---|---|---|
| (g Liquid Product)/(mMol Chromium) | 530 | 229 | 5,067 | 5,513 | 3,117 | 15,794 |
| [g ($C_6$ + $C_8$)]/(g Cr) | 9,981 | 4,276 | 96,522 | 104,808 | 59,519 | 297,591 |
| [g ($C_6$ + $C_8$)]/(g Cr)/hr | 29,942 | 12,828 | 289,565 | 314,424 | 178,558 | 892,774 |
| [g ($C_6$ + $C_8$)]/(g Aluminum) | 175 | 51 | 1825 | 5349 | 1828 | 14482 |
| (g polymer)/(g product) | 1.62 | 2.03 | 0.189 | 0.365 | 0.243 | 0.431 |
| (g polymer)/(g Chromium) | 16,519 | 8,934 | 18,415 | 38,693 | 14,590 | 130,799 |

| Example | 23 | 24 | 25 | 26 | 27 | |
|---|---|---|---|---|---|---|
| Catalyst System | | | | | | |
| Activation Method | F | F | F | F | F | |
| Complex # | A | A | A | A | A | |
| mmol complex | 0.0060 | 0.0060 | 0.0060 | 0.0060 | 0.0060 | |
| Complex Alkylaluminum | — | — | — | — | — | |
| Complex Alkylaluminum Mass (mg) | — | — | — | — | — | |
| Support | — | — | — | — | — | |
| Support Mass (mg) | — | — | — | — | — | |
| Support Alkylaluminum | — | — | — | — | — | |
| Support Alkylaluminum (mg) | — | — | — | — | — | |
| Free Alkylaluminum (g) | MMAO | MMAO | MMAO | MMAO | MMAO | |
| Free Alkylaluminum Mass (mg) | 1.275 | 1.275 | 1.275 | 1.275 | 1.275 | |
| Total Alkylaluminum (mg) | 1,275 | 1,275 | 1,275 | 1,275 | 1,275 | |
| Catalyst System Al:Cr molar ratio | 554 | 554 | 554 | 554 | 554 | |
| Catalyst Solvent | EB | EB | EB | EB | EB | |
| Solvent Mass (g) | 1 | 1 | 1 | 1 | 1 | |
| Activation Time (hours) | 0.5 | 0.5 | 0.5 | 0.5 | 0.5 | |
| Oligomerization Conditions | | | | | | |
| Diluent | CyH | CyH | MeCyH | MeCyH | CyH | |
| Diluent Volume (mL) | 200 | 200 | 200 | 200 | 200 | |
| Ethylene Pressure (psig) | 875 | 875 | 875 | 875 | 875 | |
| Hydrogen Pressure (psig) | 50 | 50 | 50 | 50 | 50 | |
| Time (min) | 20 | 20 | 20 | 20 | 20 | |
| Temperature (° C.) | 70 | 70 | 70 | 70 | 70 | |
| Oligomer Product | | | | | | |
| g liquid NAO product | 145 | 146 | 122 | 136 | 148 | |
| g polymer | 0.11 | 0.04 | 0.64 | 0.2 | 0.08 | |
| polymer (mass %) | 0.08% | 0.03% | 0.52% | 0.15% | 0.05% | |
| C # dist data (mass %) | | | | | | |
| $C_6$ | 94.5 | 94.2 | 95.1 | 94.3 | 94.5 | |
| $C_8$ | 1.0 | 1.0 | 1.4 | 1.1 | 1.0 | |
| $C_{10}$ | 4.4 | 4.4 | 3.4 | 4.6 | 4.5 | |
| $C_{12}$ | 0.0 | 0.4 | 0.1 | 0.1 | 0.1 | |
| $C_{14+}$ | 0.0 | 0.0 | 0.0 | 0.0 | 0.0 | |
| ($C_6$ + $C_8$) (mass %) | 95.6 | 95.2 | 96.5 | 95.3 | 95.5 | |
| $C_6$ Purity(mol % 1-hexene) | 99.48 | 99.63 | 99.53 | 99.45 | 99.46 | |
| $C_8$ Purity (mol % 1-octene) | 97.85 | 99.18 | 99.26 | 96.77 | 98.52 | |
| Methylcyclopentane (mass %) | 0.04 | 0.03 | 0.04 | 0.03 | 0.04 | |
| Methylenecyclopentane (mass %) | 0.01 | 0.01 | 0.02 | 0.01 | 0.01 | |
| Productivities | | | | | | |
| (g Liquid Product)/(mMol Chromium) | 24301 | 24372 | 20413 | 22757 | 24738 | |
| [g ($C_6$ + $C_8$)]/(g Cr) | 446554 | 446082 | 378995 | 417270 | 454128 | |
| [g ($C_6$ + $C_8$)]/(g Cr)/hr | 1339662 | 1338245 | 1136986 | 1251810 | 1362385 | |
| [g ($C_6$ + $C_8$)]/(g Aluminum) | 1557 | 1555 | 1321 | 1455 | 1583 | |
| (g polymer)/(g product) | 0.000756 | 0.000274 | 0.005212 | 0.001467 | 0.000540 | |
| (g polymer)/(g Chromium) | 354 | 129 | 2057 | 643 | 257 | |

| Example | 28 | 29 | 30 | 31 | 32 | 33 |
|---|---|---|---|---|---|---|
| Catalyst System | | | | | | |
| Activation Method | H | H | D | E | E | D |
| Complex # | A | A | A | A | A | B |
| mmol complex | 0.0060 | 0.0060 | 0.0060 | 0.0060 | 0.0060 | 0.0031 |
| Complex Alkylaluminum | TNOA | TNOA | TEA | TEA | | |
| Complex Alkylaluminum Mass (mg) | 0 | 0 | 0.11 | 0.055 | 0.04 | 0.020 |
| Support | FSCA | FSCA | FSCA | FSCA | Bohemite | FSCA |
| Support Mass (mg) | 0.35 | 0.35 | 0.35 | 0.35 | 0.35 | 0.175 |
| Support Alkylaluminum | MMAO | MMAO | NA | TNOA | TEA | NA |
| Support Alkylaluminum (mg) | | 0.085 | 0.17 | 0.055 | 0.035 | 0 |
| Free Alkylaluminum (g) | | | | | | |
| Free Alkylaluminum Mass (mg) | | | | | | |
| Total Alkylaluminum (mg) | 0.085 | 0.17 | NA | NA | | |
| Catalyst System Al:Cr molar ratio | 37 | 74 | 50 | 50 | 110 | 57 |

TABLE 3-continued

| | | | | | | |
|---|---|---|---|---|---|---|
| Catalyst Solvent | EB | EB | EB | EB | EB | EB |
| Solvent Mass (g) | 1 | 1 | 1 | 1 | 1 | 1 |
| Activation Time (hours) | 0.5 | 0.5 | 0.5 | 0.5 | 0.5 | 0.5 |
| Oligomerization Conditions | | | | | | |
| Diluent | CyH | CyH | CyH | CyH | CyH | CyH |
| Diluent Volume (mL) | 200 | 200 | 200 | 200 | 200 | 200 |
| Ethylene Pressure (psig) | 875 | 875 | 875 | 875 | 50 | 50 |
| Hydrogen Pressure (psig) | 50 | 50 | 50 | 50 | 875 | 875 |
| Time (min) | 20 | 20 | 20 | 20 | 20 | 60 |
| Temperature (° C.) | 70 | 70 | 70 | 70 | 70 | 70 |
| Oligomer Product | | | | | | |
| g liquid NAO product | 50.1 | 61.0 | 82 | 74 | 0.0 | 13 |
| g polymer | 61 | 48 | 25 | 35 | 116 | 3.9 |
| polymer (mass%) | 54.92% | 44.04% | 23.29% | 32.30% | 100.0 | 23.28% |
| C # dist data (mass %) | | | | | | |
| $C_6$ | 96.1 | 96.4 | 96.6 | 96.7 | 0.0 | 79.4 |
| $C_8$ | 2.3 | 2.2 | 1.3 | 1.6 | 0.0 | 18.6 |
| $C_{10}$ | 1.4 | 1.4 | 2.0 | 1.7 | 0.0 | 2.0 |
| $C_{12}$ | 0.2 | 0.0 | 0.0 | 0.0 | 0.00 | 0.0 |
| $C_{14+}$ | 0.0 | 0.0 | 0.0 | 0.0 | 100.00 | 0.0 |
| ($C_6 + C_8$) (mass %) | 98.4 | 98.6 | 98.0 | 98.3 | 0.00 | 98.0 |
| $C_6$ Purity (mol % 1-hexene) | 99.67 | 99.67 | 99.53 | 99.59 | NA | 95.88 |
| $C_8$ Purity (mol % 1-octene) | 97.78 | 98.39 | 94.86 | 95.42 | NA | 97.72 |
| Methylcyclopentane (mass %) | 0.07 | 0.09 | 0.05 | 0.05 | NA | 2.79 |
| Methylenecyclopentane (mass %) | 0.04 | 0.04 | 0.03 | 0.03 | NA | 0.82 |
| Productivities | | | | | | |
| (g Liquid Product)/(mMol Chromium) | 8,367 | 10,194 | 13,703 | 12,366 | 0 | 4,164 |
| [g ($C_6 + C_8$)]/(g Cr) | 158,343 | 193,336 | 258,165 | 233,695 | — | 78,469 |
| [g ($C_6 + C_8$)]/(g Cr)/hr | 475,030 | 580,009 | 774,495 | 701,086 | — | 78,469 |
| [g ($C_6 + C_8$)]/(g Aluminum) | 8281 | 5055 | 10433 | 9444 | 0 | 2666 |
| (g polymer)/(g product) | 1.22 | 0.79 | 0.30 | 0.48 | NA | 0.30 |
| (g polymer)/(g Chromium) | 196,038 | 154,259 | 80,022 | 113,445 | 372,793 | 24,290 |

| Example | 34 | 35 | 36 | 37 | 38 | 39 |
|---|---|---|---|---|---|---|
| Catalyst System | | | | | | |
| Activation Method | D | D | D | D | B | C |
| Complex # | B | B | B | B | B | B |
| mmol complex | 0.0031 | 0.0031 | 0.0031 | 0.0031 | 0.0031 | 0.0031 |
| Complex Alkylaluminum | TEA | TEA | TEA | TEA | NA | NA |
| Complex Alkylaluminum Mass (mg) | 0.040 | 0.030 | 0.030 | 0.030 | 0.000 | 0.000 |
| Support | FSCA | FSCA | FSCA | FSCA | FSCA | FSCA |
| Support Mass (mg) | 0.175 | 0.175 | 0.175 | 0.175 | 0.175 | 0.175 |
| Support Alkylaluminum | NA | NA | NA | NA | TEA | TEA |
| Support Alkylaluminum (mg) | 0 | 0 | 0 | 0 | 0.03 | 0.03 |
| Free Alkylaluminum (g) | | | | | | |
| Free Alkylaluminum Mass (mg) | | | | | | |
| Total Alkylaluminum (mg) | | | | | | |
| Catalyst System Al:Cr molar ratio | 113 | 85 | 85 | 85 | 85 | 85 |
| Catalyst Solvent | EB | EB | EB | EB | EB | EB |
| Solvent Mass (g) | 1 | 1 | 1 | 1 | 1 | 1 |
| Activation Time (hours) | 0.5 | 0.5 | 1 | 0.5 | 0.5 | 0.5 |
| Oligomerization Conditions | | | | | | |
| Diluent | CyH | CyH | CyH | CyH | CyH | CyH |
| Diluent Volume (mL) | 200 | 200 | 200 | 200 | 200 | 200 |
| Ethylene Pressure (psig) | 50 | 50 | 50 | 50 | 50 | 50 |
| Hydrogen Pressure (psig) | 875 | 875 | 875 | 875 | 875 | 875 |
| Time (min) | 60 | 60 | 60 | 75 | 60 | 60 |
| Temperature (° C.) | 70 | 70 | 70 | 70 | 70 | 70 |
| Oligomer Product | | | | | | |
| g liquid NAO product | 13 | 18 | 16 | 19 | 15 | 16 |
| g polymer | 6.2 | 6.1 | 5 | 6.6 | 7.1 | 9.8 |
| polymer (mass%) | 32.28% | 25.66% | 23.51% | 26.22% | 31.74% | 37.63% |
| C # dist data (mass %) | | | | | | |
| $C_6$ | 78.6 | 79.1 | 78.4 | 78.6 | 78.8 | 78.3 |
| $C_8$ | 19.2 | 18.8 | 19.1 | 18.6 | 18.4 | 19.0 |
| $C_{10}$ | 2.2 | 2.1 | 2.1 | 2.2 | 2.1 | 2.3 |
| $C_{12}$ | 0.0 | 0.0 | 0.4 | 0.6 | 0.6 | 0.5 |
| $C_{14+}$ | 0.0 | 0.0 | 0.0 | 0.0 | 0.0 | 0.0 |
| ($C_6 + C_8$) (mass %) | 97.8 | 97.9 | 97.5 | 97.2 | 97.2 | 97.3 |
| $C_6$ Purity (mol % 1-hexene) | 95.99 | 95.77 | 95.88 | 95.68 | 96.30 | 96.46 |
| $C_8$ Purity (mol % 1-octene) | 96.71 | 97.49 | 97.48 | 97.30 | 97.46 | 97.40 |

TABLE 3-continued

| | | | | | | |
|---|---|---|---|---|---|---|
| Methylcyclopentane (mass %) | 2.71 | 2.88 | 2.79 | 2.74 | 2.64 | 2.78 |
| Methylenecyclopentane (mass %) | 0.64 | 0.76 | 0.75 | 1.03 | 0.50 | 0.19 |
| Productivities | | | | | | |
| (g Liquid Product)/(mMol Chromium) | 4,212 | 5,723 | 5,268 | 6,015 | 4,946 | 5,261 |
| [g ($C_6$ + $C_8$)]/(g Cr) | 79,220 | 107,745 | 98,770 | 112,439 | 92,446 | 98,441 |
| [g ($C_6$ + $C_8$)]/(g Cr)/hr | 79,220 | 107,745 | 98,770 | 89,951 | 92,446 | 98,441 |
| [g ($C_6$ + $C_8$)]/(g Aluminum) | 1345 | 2440 | 2237 | 2546 | 2094 | 2229 |
| (g polymer)/(g product) | 0.48 | 0.35 | 0.31 | 0.36 | 0.46 | 0.60 |
| (g polymer)/(g Chromium) | 38,615 | 37,992 | 31,141 | 41,106 | 44,220 | 61,036 |

| Example | 40 | 41 | 42 | 43 | 44 | 45 |
|---|---|---|---|---|---|---|
| Catalyst System | | | | | | |
| Activation Method | E | G | D | D | D | D |
| Complex # | B | B | B | B | B | B |
| mmol complex | 0.0031 | 0.0031 | 0.0031 | 0.0031 | 0.0031 | 0.0031 |
| Complex Alkylaluminum | TEA | TEA | TIBA | TIBA | TIBA | TIBA |
| Complex Alkylaluminum Mass (mg) | 0.015 | 0.030 | 0.030 | 0.040 | 0.055 | 0.075 |
| Support | FSCA | FSCA | FSCA | FSCA | FSCA | FSCA |
| Support Mass (mg) | 0.175 | 0.175 | 0.175 | 0.175 | 0.175 | 0.175 |
| Support Alkylaluminum | TEA | NA | NA | NA | NA | NA |
| Support Alkylaluminum (mg) | 0.015 | 0 | 0 | 0 | 0 | 0 |
| Free Alkylaluminum (g) | | | | | | |
| Free Alkylaluminum Mass (mg) | | | | | | |
| Total Alkylaluminum (mg) | | | | | | |
| Catalyst System Al:Cr molar ratio | 85 | 85 | 49 | 65 | 90 | 122 |
| Catalyst Solvent | EB | EB | EB | EB | EB | EB |
| Solvent Mass (g) | 1 | 1 | 1 | 1 | 1 | 1 |
| Activation Time (hours) | 0.5 | 0.5 | 0.5 | 0.5 | 0.5 | 0.5 |
| Oligomerization Conditions | | | | | | |
| Diluent | CyH | CyH | CyH | CyH | CyH | CyH |
| Diluent Volume (mL) | 200 | 200 | 200 | 200 | 200 | 200 |
| Ethylene Pressure (psig) | 50 | 50 | 875 | 875 | 875 | 875 |
| Hydrogen Pressure (psig) | 875 | 875 | 50 | 50 | 50 | 50 |
| Time (min) | 60 | 60 | 60 | 60 | 60 | 60 |
| Temperature (° C.) | 70 | 70 | 70 | 70 | 70 | 70 |
| Oligomer Product | | | | | | |
| g liquid NAO product | 1 | 14 | 8 | 12 | 14 | 14 |
| g polymer | 2.5 | 5 | 2 | 4.5 | 4.5 | 4.1 |
| polymer (mass %) | 70.63% | 26.52% | 20.81% | 28.03% | 24.58% | 22.97% |
| C # dist data (mass %) | | | | | | |
| $C_6$ | 73.5 | 78.1 | 78.4 | 79.5 | 78.7 | 78.5 |
| $C_8$ | 23.0 | 19.1 | 19.4 | 18.2 | 18.6 | 18.4 |
| $C_{10}$ | 3.5 | 2.1 | 2.2 | 2.3 | 2.3 | 2.2 |
| $C_{12}$ | 0.0 | 0.6 | 0.0 | 0.0 | 0.3 | 0.0 |
| $C_{14+}$ | 0.0 | 0.0 | 0.0 | 0.0 | 0.0 | 0.9 |
| ($C_6$ + $C_8$) (mass %) | 96.5 | 97.2 | 97.8 | 97.7 | 97.4 | 96.9 |
| $C_6$ Purity(mol % 1-hexene) | 92.50 | 95.95 | 94.23 | 95.09 | 94.72 | 94.00 |
| $C_8$ Purity (mol % 1-octene) | 93.34 | 97.27 | 97.01 | 97.14 | 97.47 | 96.40 |
| Methylcyclopentane (mass %) | 3.66 | 2.83 | 2.69 | 2.61 | 2.71 | 2.62 |
| Methylenecyclopentane (mass %) | 1.54 | 0.59 | 2.41 | 1.71 | 1.94 | 2.50 |
| Productivities | | | | | | |
| (g Liquid Product)/(mMol Chromium) | 337 | 4,487 | 2,465 | 3,742 | 4,472 | 4,452 |
| [g ($C_6$ + $C_8$)]/(g Cr) | 6,249 | 83,872 | 46,384 | 70,273 | 83,728 | 82,934 |
| [g ($C_6$ + $C_8$)]/(g Cr)/hr | 6,249 | 83,872 | 46,384 | 70,273 | 83,728 | 82,934 |
| [g ($C_6$ + $C_8$)]/(g Aluminum) | 142 | 1899 | 1825 | 2074 | 1797 | 1305 |
| (g polymer)/(g product) | 2.40 | 0.36 | 0.26 | 0.39 | 0.33 | 0.30 |
| (g polymer)/(g Chromium) | 15,571 | 31,141 | 12,456 | 28,027 | 28,027 | 25,536 |

TABLE 4

| Example | Mn/1000 (g/mol) | Mw/1000 (g/mol) | Mz/1000 (g/mol) | Mv/1000 (g/mol) | Mp/1000 (g/mol) | Mw/Mn | IB | IVc |
|---|---|---|---|---|---|---|---|---|
| 1 | 12.93 | 217.95 | 1439.88 | 156.5 | 58.24 | 16.86 | 1.875 | 2.332 |
| 5 | 16.64 | 174.79 | 939.91 | 133.66 | 69.04 | 10.5 | 1.517 | 2.08 |
| 10 | 13.08 | 182.1 | 1192.15 | 133.99 | 58.24 | 13.92 | 1.542 | 2.084 |
| 11 | 14.12 | 158.9 | 978.05 | 118.74 | 51.97 | 11.25 | 1.443 | 1.909 |
| 14 | 10.77 | 191.67 | 1341.03 | 138.67 | 63.26 | 17.80 | 1.812 | 2.136 |
| 15 | 10.97 | 184.27 | 1344.04 | 132.12 | 54.30 | 16.80 | 1.813 | 2.063 |
| 17 | 13.91 | 214.54 | 1028.03 | 161.70 | 73.67 | 15.42 | 1.882 | 2.388 |

TABLE 4-continued

| 22 | 16.07 | 159.13 | 1038.11 | 119.37 | 53.31 | 9.9 | 1.489 | 1.916 |
| 35 | 15.79 | 352.61 | 1990.62 | 258.26 | 144.25 | 22.3 | — | — |
| 37 | 12.60 | 368.69 | 2232.15 | 263.23 | 120.36 | 29.3 | — | — |

TABLE 5

| | Side Chains | | | | | | Chain ENDS | | Internal Unsaturation | |
| --- | --- | --- | --- | --- | --- | --- | --- | --- | --- | --- |
| Example | Propylene mol % | 1-Butene mol % | 1-Hexane mol % | Ethylene mol % | LB/ 1000 TC | SCB/ 1000 TC | Sat/ 1000 TC | Vinyl/ 1000 TC | trans/ 1000 TC | cis/ 1000 TC |
| 10 | 0.05% | 0.00% | 0.07% | 99.88% | 0.1 | 0.6 | 0.98 | 0.44 | 0 | 0.35 |
| 11 | 0.10% | 0.00% | 0.16% | 99.74% | 0.1 | 1.3 | 1.33 | 0.39 | 0 | 0.48 |

In Examples 46 and 47, ethylene oligomerizations were performed using the chromium(III) complex of the diphosphino amine ligand having Structure PNP 5. In Example 46, the catalyst system was prepared by combining 2 mg of the chromium(III) complex of the diphosphino amine ligand having Structure PNP 5, 1 mL of benzene, and 0.725 grams of MMAO-3. The catalyst system mixture was then aged at room temperature for 30 minutes. The aged catalyst system mixture was then mixed into cyclohexane, 200 mL, which was then charged to an evacuated autoclave reactor (0.5 L stainless steel ZipperClave® Autoclave) held at 70° C. The reactor was then charged with 50 psig $H_2$ and 875 psig ethylene. Ethylene was then oligomerized at 70° C., with stirring (through an air driven autoclave stirrer motor). The ethylene oligomerization temperature was maintained by use of internal cooling coils and if necessary an external water bath. As the reaction proceeded, ethylene was fed to the reactor on demand to maintain the autoclave reactor pressure for the reaction time of 20 minutes. At ethylene oligomerization completion, water cooling was applied to the autoclave reactor. When the autoclave reactor contents temperature reached 35° C., the unreacted ethylene and hydrogen gas were vented from the reactor. A liquid sample (~2 mL) of the reactor contents was then collected, filtered, and analyzed by GC-FID. The reactor solids were collected by filtering the reaction mixture and cleaning the reactor walls and cooling coil. Analysis of the reactor contents showed that the ethylene oligomerization produced 47 grams of liquid oligomer product containing 27.4 wt. % $C_6$ product (of which 83.4 wt. % was 1-hexene) and 69.6 wt. % $C_8$ product (of which 99.29 wt. % was 1-octene), and 0.23 grams of polymer.

In Example 47, the catalyst system was prepared using Activation Method E by 1) preparing a first mixture by combining 2 mg of the chromium(III) complex of the diphosphino amine ligand having Structure PNP 5, 1 mL of benzene, and 0.2 grams of TEA and aging the first mixture for 30 minutes; 2) preparing a second mixture containing 200 mg of FSCA and 10 mL cyclohexane containing 0.02 g TEA and then aging the second mixture for 30 minutes; 3) combining the first and second mixtures and aging the combined mixture for 30 minutes to produce the catalyst system mixture. The ethylene oligomerization was conducted as described in Example 46. Analysis of the reactor contents of Example 47 showed that the ethylene oligomerization produced 10 grams of liquid oligomer product containing 47.3 wt. % $C_6$ product (of which 89.41 wt. % was 1-hexene) and 49.8 wt. % $C_8$ product (of which 97.9 wt. % was 1-octene), and 19.6 grams of polymer. Example 47 demonstrates that using a chemically-treated solid oxide provides for the concurrent co-production of ethylene oligomers and polyethylene without substantial reactor fouling and/or plugging.

The invention is described above with reference to numerous aspects and embodiments, and specific examples. Many variations will suggest themselves to those skilled in the art in light of the above detailed description. All such obvious variations are within the full intended scope of the appended claims. Other embodiments of the invention can include, but are not limited to, the following (embodiments are described as "comprising" but, alternatively, can "consist essentially of" or "consist of"):

Embodiment 1

A catalyst system comprising:
a) a heteroatomic ligand transition metal compound complex;
b) a chemically-treated solid oxide; and
c) an organoaluminum compound.

Embodiment 2

The catalyst system in embodiment 1, wherein the chemically-treated solid oxide comprises a solid oxide treated with an electron-withdrawing anion, e.g., any solid oxide and any electron-withdrawing anion disclosed herein.

Embodiment 3

The catalyst system in embodiment 1, wherein (a) the solid oxide comprises silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof, and (b) the electron-withdrawing anion comprises sulfate, bisulfate, fluoride, chloride, bromide, iodide, fluorosulfate, fluoroborate, phosphate, acetate, fluorophosphate, trifluoroacetate, triflate, fluorozirconate, fluorotitanate, phospho-tungstate, or any combination thereof.

Embodiment 4

The catalyst system in embodiment 2 or 3, wherein the solid oxide comprises silica, alumina, silica-alumina, silica-coated alumina, or a mixture thereof.

Embodiment 5

The catalyst system in embodiment 2 or 3, wherein the solid oxide comprises silica-coated alumina.

Embodiment 6

The catalyst system in any one of embodiments 2-5, wherein the electron-withdrawing anion comprises sulfate, fluoride, chloride, or any combination thereof.

Embodiment 7

The catalyst system in any one of embodiments 2-6, wherein the electron-withdrawing anion comprises sulfate.

Embodiment 8

The catalyst system in any one of embodiments 2-6, wherein the electron-withdrawing anion comprises fluoride, chloride, or both.

Embodiment 9

The catalyst system in embodiment 1, wherein the chemically-treated solid oxide comprises fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, or any combination thereof.

Embodiment 10

The catalyst system in embodiment 1, wherein the chemically-treated solid oxide comprises a fluorided solid oxide, a sulfated solid oxide, or a combination thereof.

Embodiment 11

The catalyst system in embodiment 1, wherein the chemically-treated solid oxide comprises fluorided alumina, sulfated alumina, fluorided silica-alumina, sulfated silica-alumina, fluorided silica-coated alumina, fluorided-chlorided silica-coated alumina, sulfated silica-coated alumina, or any combination thereof.

Embodiment 12

The catalyst system in embodiment 1, wherein the chemically-treated solid oxide comprises fluorided silica-coated alumina.

Embodiment 13

The catalyst system in embodiment 1, wherein the chemically-treated solid oxide comprises sulfated alumina.

Embodiment 14

The catalyst system in any one of embodiments 2-13, wherein the chemically-treated solid oxide further comprises any metal or metal ion disclosed herein, e.g., zinc, nickel, vanadium, titanium, silver, copper, gallium, tin, tungsten, molybdenum, zirconium, or any combination thereof.

Embodiment 15

The catalyst system in any one of the preceding embodiments, wherein the organoaluminum compound comprises any organoaluminum compound disclosed herein.

Embodiment 16

The catalyst system in any one of the preceding embodiments, wherein the organoaluminum compound comprises an aluminoxane; alternatively, an alkylaluminum compound; or alternatively, a trialkylaluminum compound.

Embodiment 17

The catalyst system in embodiment 15, wherein the organoaluminum compound comprises trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, or any combination thereof.

Embodiment 18

The catalyst system in embodiment 17, wherein the alkylaluminum compound comprises triethylaluminum.

Embodiment 19

The catalyst system in any one of the preceding embodiments, wherein the catalyst system is substantially free of aluminoxane compounds.

Embodiment 20

The catalyst system in any one of the preceding embodiments, wherein the heteroatomic ligand transition metal compound complex comprises any transition metal disclosed herein, e.g., a Group 5-10 transition metal.

Embodiment 21

The catalyst system in any one of the preceding embodiments, wherein the heteroatomic ligand transition metal compound complex comprises chromium, iron, nickel, or cobalt, either singly or in combination.

Embodiment 22

The catalyst system in any one of the preceding embodiments, wherein the heteroatomic ligand transition metal compound complex comprises a diphosphino amine transition metal compound complex, an $N^2$-phosphinyl amidine transition metal compound complex, an $N^2$-phosphinyl formamidine transition metal compound complex, an $N^2$-phosphinyl guanidine transition metal compound complex, or any combination thereof.

Embodiment 23

The catalyst system in any one of the preceding embodiments, wherein the heteroatomic ligand transition metal compound complex comprises a diphosphino amine chromium compound complex, an $N^2$-phosphinyl amidine chromium compound complex, an $N^2$-phosphinyl formamidine chromium compound complex, an $N^2$-phosphinyl guanidine chromium compound complex, or any combination thereof.

Embodiment 24

The catalyst system in any one of embodiments 1-23, wherein the heteroatomic ligand transition metal compound complex comprises an $N^2$-phosphinyl amidine chromium compound complex, or alternatively, a diphosphino amine chromium compound complex.

Embodiment 25

The catalyst system in any one of embodiments 1-23, wherein the heteroatomic ligand transition metal compound complex comprises an $N^2$-phosphinyl formamidine chromium compound complex.

Embodiment 26

The catalyst system in any one of embodiments 1-23, wherein the heteroatomic ligand transition metal compound complex comprises an $N^2$-phosphinyl guanidine chromium compound complex.

Embodiment 27

The catalyst system in any one of the preceding embodiments, wherein the weight ratio of the transition metal of the heteroatomic ligand transition metal compound complex (or complexes) to the chemically-treated solid oxide (or oxides) is in any range of weight ratios disclosed herein, e.g., from 1:1 to 1:1,000,000, from 1:10 to 1:10,000, from 1:20 to 1:1000, etc.

Embodiment 28

The catalyst system in any one of the preceding embodiments, wherein the weight ratio of the chemically-treated solid oxide (or oxides) to the organoaluminum compound (or compounds) is in any range of weight ratios disclosed herein, e.g., from 1:5 to 1000:1, from 1:3 to 200:1, from 1:1 to 100:1, etc.

Embodiment 29

A process for preparing a catalyst system in any one of embodiments 1-28, the process comprising contacting, in any order, a heteroatomic ligand transition metal compound complex, a chemically-treated solid oxide, and an organoaluminum compound to form a catalyst system mixture.

Embodiment 30

A process for preparing the catalyst system in any one of embodiments 1-28 comprising: (i) contacting a chemically-treated solid oxide and an organoaluminum compound for a first period of time to form a precontacted mixture; and (ii) contacting the precontacted mixture with a heteroatomic ligand transition metal compound complex for a second period of time to form the catalyst system; or alternatively, (i) contacting a heteroatomic ligand transition metal compound complex and an organoaluminum compound for a first period of time to form a precontacted mixture; and (ii) contacting the precontacted mixture with a chemically-treated solid oxide for a second period of time to form the catalyst system.

Embodiment 31

The process in embodiment 30, wherein the first period of time is in any range of first time periods disclosed herein, e.g., at least 5 seconds, at least 5 minutes, at least 10 minutes, from 5 seconds to 48 hours, from 5 minutes to 6 hours, etc.

Embodiment 32

The process in any one of embodiments 30-31, wherein the second period of time is in any range of second time periods disclosed herein, e.g., at least 5 seconds, at least 5 minutes, at least 10 minutes, from 5 seconds to 48 hours, from 5 minutes to 6 hours, etc.

Embodiment 33

A process for preparing the catalyst system in any one of embodiments 1-28 comprising:

(i) contacting a chemically-treated solid oxide and a first organoaluminum compound for a first period of time to form a first mixture;

(ii) contacting a heteroatomic ligand transition metal compound complex and a second organoaluminum compound for a second period of time to form a second mixture; and (iii) contacting the first mixture with the second mixture for a third period of time to form the catalyst system.

Embodiment 34

The process in embodiment 33, wherein the first period of time and the second period of time are independently in any range of first and second time periods disclosed herein, e.g., at least 5 seconds, at least 5 minutes, at least 10 minutes, from 5 seconds to 48 hours, from 5 minutes to 6 hours, etc.

Embodiment 35

The process in embodiment 33 or 34, wherein the third period of time is in any range of third time periods disclosed herein, e.g., at least 5 seconds, at least 5 minutes, at least 10 minutes, from 5 seconds to 48 hours, from 5 minutes to 6 hours, etc.

Embodiment 36

The process in any one of embodiments 33-35, wherein the first organoaluminum compound and the second first organoaluminum compound are different, or alternatively, the first organoaluminum compound and the second first organoaluminum compound are the same.

Embodiment 37

A catalyst system produced by the process of any one of embodiments 29-36.

Embodiment 38

A process comprising a) contacting i) ethylene, ii) the catalyst system in any one of embodiments 1-28, and iii) optionally an organic reaction medium, and b) forming an oligomer product.

Embodiment 39

A process comprising a) preparing a catalyst system according to the process in any one of embodiments 29-36; b) contacting the catalyst system prepared in step a) with ethylene and optionally an organic reaction medium; and c) forming an oligomer product.

Embodiment 40

The process in embodiment 39, wherein a productivity of the catalyst system (in kg ($C_6+C_8$)/g transition metal, kg ($C_6+C_8$)/g transition metal/hr, or kg ($C_6+C_8$)/g Al) is greater (by any amount disclosed herein, e.g., at least 10%, at least 25%, at least 100%, etc.) than that of a similar process wherein a catalyst system is prepared by contacting the chemically-treated solid oxide and the heteroatomic ligand transition metal compound complex to form an mixture, and then contacting the first mixture with the organoaluminum compound; or simultaneously contacting the chemically-treated solid oxide, the heteroatomic ligand transition metal compound complex, and the organoaluminum compound.

Embodiment 41

The process in embodiment 39, wherein a productivity of the catalyst system (in kg ($C_6+C_8$)/g transition metal, kg ($C_6+C_8$)/g transition metal/hr, or kg ($C_6+C_8$)/g Al) is from 10% to 500% greater, or from 25% to 200% greater, etc., than that of a similar process wherein a catalyst system is prepared by contacting the chemically-treated solid oxide and the heteroatomic ligand transition metal compound complex to form an mixture, and then contacting the first mixture with the organoaluminum compound; or simultaneously contacting the chemically-treated solid oxide, the heteroatomic ligand transition metal compound complex, and the organoaluminum compound.

Embodiment 42

The process in any one of embodiments 38-41, wherein the oligomer product is formed at an oligomerization temperature in any oligomerization temperature range disclosed herein, e.g., from 0° C. to 165° C., from 20° C. to 160° C., from 40° C. to 160° C., from 50° C. to 150° C., from 50° C. to 140° C., from 50° C. to 130° C., from 45° C. to 100° C., from 45° C. to 90° C., etc.

Embodiment 43

The process in any one of embodiments 38-42, wherein the oligomer product is formed at a reaction pressure (or ethylene partial pressure) in any range disclosed herein, e.g., from 50 psig (344 kPa) to 4,000 psig (27.6 MPa), from 100 psig (689 kPa) to 3,000 psig (20.9 MPa), from 200 psig (1.4 MPa) to 2,000 psig (13.8 MPa), from 250 psig (1.5 MPa) to 1,500 psig (10.3 MPa), etc.

Embodiment 44

The process in any one of embodiments 38-43, wherein the oligomer product is formed in the substantial absence of hydrogen (e.g., no added hydrogen).

Embodiment 45

The process in any one of embodiments 38-43, wherein the oligomer product is formed in the presence of hydrogen.

Embodiment 46

The process in embodiment 45, wherein the oligomer product is formed at a hydrogen partial pressure in any range disclosed herein, e.g., from 1 psig (6.9 kPa) to 2000 psig (13.8 MPa), from 5 psig (34 kPa) to 1500 psig (10.3 MPa), from 10 psig (69 kPa) to 1000 psig (6.9 MPa), from 10 psig (69 kPa) to 500 psig (3.5 MPa), from 25 psig (172 kPa) to 500 psig (3.4 MPa), etc.

Embodiment 47

The process in any one of embodiments 38-46, wherein a productivity of the catalyst system is in any range disclosed herein, e.g., greater than 25,000 grams, greater than 50,000 grams, greater than 100,000 grams, greater than 150,000 grams, etc., of $C_6+C_8$ per gram of transition metal, under oligomerization conditions, with a triethylaluminum co-catalyst, using cyclohexane as a diluent and 50 psig hydrogen pressure, and with an oligomerization temperature of 70° C. and an ethylene pressure of 875 psig.

Embodiment 48

The process in any one of embodiments 38-47, wherein a productivity of the catalyst system is in any range disclosed herein, e.g., greater than 1,000 grams, greater than 2,500 grams, greater than 10,000 grams, greater than 50,000 grams, etc., of ethylene polymer per gram of transition metal, under oligomerization conditions, with a triethylaluminum co-catalyst, using cyclohexane as a diluent and 50 psig hydrogen pressure, and with an oligomerization temperature of 70° C. and an ethylene pressure of 875 psig.

Embodiment 49

The process in any one of embodiments 38-48, wherein the oligomer product is formed in the substantial absence of aluminoxanes.

Embodiment 50

The process in any one of embodiments 38-49, wherein the oligomer product is formed in the presence of an organic reaction medium, e.g., any organic reaction medium disclosed herein, e.g., a hydrocarbon (for instance, cyclohexane or methylcyclohexane), a halogenated hydrocarbon, or any combination thereof.

Embodiment 51

The process in any one of embodiments 38-50, wherein the oligomer product is formed in a reaction system comprising a stirred tank reactor, a plug flow reactor, or any combination thereof; alternatively, a fixed bed reactor, a

Embodiment 52

The process in any one of embodiments 38-51, wherein the process further comprises a step of deactivating the catalyst system using any suitable technique or any technique disclosed herein.

Embodiment 53

The process in any one of embodiments 38-52, wherein the oligomer product comprises a liquid oligomer product (liquid at standard temperature and pressure) and a solid polymer product (solid at standard temperature and pressure).

Embodiment 54

The process in embodiment 53, wherein the weight percentage of the solid polymer product, based on the total weight of the oligomer product, is in any range disclosed herein, e.g., from 2 wt. % to 80 wt. %, from 2 wt. % to 65 wt. %, from 2 wt. % to 30 wt. %, from 5 wt. % to 65 wt. %, from 5 wt. % to 30 wt. %, from 10 wt. % to 40 wt. %, etc.

Embodiment 55

The process in any one of embodiments 53-54, wherein the liquid oligomer product comprises $C_6$ and $C_8$ olefins.

Embodiment 56

The process in any one of embodiments 53-55, wherein the liquid oligomer product comprises an amount of $C_6$ and $C_8$ olefins (total) in any range disclosed herein, e.g., from 70 to 99.9 wt. %, from 80 to 99.9 wt. %, from 90 to 99.9 wt. %, from 92 to 99.9 wt. %, from 96 to 99.9 wt. %, etc.

Embodiment 57

The process in any one of embodiments 53-56, wherein the liquid oligomer product comprises an amount of $C_6$ olefins in any range disclosed herein, e.g., from 70 to 99.9 wt. %, from 80 to 99.9 wt. %, from 90 to 99.9 wt. %, from 92 to 99.9 wt. %, from 95 to 99.9 wt. %, etc.

Embodiment 58

The process in any one of embodiments 53-57, wherein the oligomer product and the liquid oligomer product comprise a $C_6$ oligomer product comprising an amount of 1-hexene in any range disclosed herein, e.g., from 90 to 99.99 mol %, from 95 to 99.99 mol %, from 98 to 99.99 mol %, from 99 to 99.99 mol %, etc.

Embodiment 59

The process in any one of embodiments 53-58, wherein the oligomer product and the liquid oligomer product comprise a $C_8$ oligomer product comprising an amount of 1-octene in any range disclosed herein, e.g., from 90 to 99.99 mol %, from 95 to 99.99 mol %, from 97 to 99.99 mol %, from 98 to 99.99 mol %, etc.

Embodiment 60

The process in any one of embodiments 53-59, wherein the solid polymer product comprises an ethylene polymer (e.g., an ethylene homopolymer).

Embodiment 61

The process in any one of embodiments 53-60, wherein the solid polymer product has a Mn in any range of Mn's disclosed herein, e.g., from 5,000 to 25,000 g/mol, from 5,000 to 20,000 g/mol, from 8,000 to 25,000 g/mol, from 8,000 to 20,000 g/mol, etc.

Embodiment 62

The process in any one of embodiments 53-61, wherein the solid polymer product has a Mp in any range of Mp's disclosed herein, e.g., from 30,000 to 200,000 g/mol, from 30,000 to 170,000 g/mol, from 35,000 to 170,000 g/mol, from 40,000 to 160,000 g/mol, etc.

Embodiment 63

The process in any one of embodiments 53-62, wherein the solid polymer product is insoluble in the organic reaction medium, e.g., a hydrocarbon (for instance, cyclohexane or methylcyclohexane), a halogenated hydrocarbon, or any combination thereof.

Embodiment 64

The process in any one of embodiments 53-63, wherein at least a portion of the solid polymer product comprises chemically-treated solid oxide particles.

Embodiment 65

The process in any one of embodiments 53-64, wherein the process further comprises a step of isolating the liquid oligomer product, e.g., from the solid polymer product, from the organic reaction medium, etc., using any suitable technique or any technique disclosed herein, e.g., a filtration process, an evaporation process, a distillation process, as well as combinations thereof.

Embodiment 66

The process in any one of embodiments 53-65, wherein the process further comprises a step of isolating the solid polymer product, e.g., from the liquid oligomer product, from the organic reaction medium, etc., using any suitable technique or any technique disclosed herein, e.g., a filtration process, an evaporation process, a distillation process, as well as combinations thereof.

Embodiment 67

The process in any one of embodiments 53-66, wherein the process further comprises a step of separating solid polymer product comprising at least a portion of the catalyst system (or deactivated catalyst system), e.g., from the liquid oligomer product, from the organic reaction medium, etc., using any suitable liquid-solid separation technique or any technique disclosed herein, e.g., a filtration process, an evaporation process, a distillation process, as well as combinations thereof.

Embodiment 68

The process in any one of embodiments 38-67, wherein the process is performed without reactor fouling, e.g., no reactor fouling (without substantial reactor fouling, substantially no reactor fouling) in any reactor or multi-reactor system disclosed herein, e.g., a stirred tank reactor, a plug flow reactor, or any combination thereof; or alternatively, a fixed bed reactor, a continuous stirred tank reactor, a loop slurry reactor, a solution reactor, a tubular reactor, a recycle reactor, or any combination thereof.

Embodiment 69

A liquid oligomer product (liquid at standard temperature and pressure) produced by the process in any one of embodiments 38-68.

Embodiment 70

A solid polymer product (solid at standard temperature and pressure) produced by the process in any one of embodiments 38-68.

Embodiment 71

An article comprising (or formed from) the solid polymer product in embodiment 70.

Embodiment 72

The article in embodiment 71, wherein the article is an agricultural film, an automobile part, a bottle, a drum, a fiber or fabric, a food packaging film or container, a food service article, a fuel tank, a geomembrane, a household container, a liner, a molded product, a medical device or material, a pipe, a sheet or tape, or a toy.

We claim:

1. A process comprising:
   a) contacting
      i) ethylene;
      ii) a catalyst system comprising:
         a) a heteroatomic ligand transition metal compound complex;
         b) a chemically-treated solid oxide; and
         c) an organoaluminum compound; and
      iii) optionally, an organic reaction medium; and
   b) forming an oligomer product comprising a liquid oligomer product and a solid polymer product; wherein:
   the weight percentage of the solid polymer product, based on the total weight of the liquid oligomer product and the solid polymer product, is in a range from 5 wt. % to 65 wt. %.

2. The process of claim 1, wherein:
   the liquid oligomer product comprises $C_6$ and $C_8$ olefins; and
   the solid polymer product comprises an ethylene polymer.

3. The process of claim 2, wherein a productivity of the catalyst system is greater than 50,000 grams of $C_6+C_8$ per gram of transition metal, under oligomerization conditions, with triethylaluminum as the organoaluminum compound, cyclohexane as the organic reaction medium, and with a hydrogen pressure of 50 psig, an ethylene pressure of 875 psig, and an oligomerization temperature of 70° C.

4. The process of claim 2, wherein a productivity of the catalyst system is greater than 10,000 grams of the solid polymer product per gram of transition metal, under oligomerization conditions, with triethylaluminum as the organoaluminum compound, cyclohexane as the organic reaction medium, and with a hydrogen pressure of 50 psig, an ethylene pressure of 875 psig, and an oligomerization temperature of 70° C.

5. A The process of claim 2, wherein the weight percentage of the solid polymer product, based on the total weight of the liquid oligomer product and the solid polymer product, is in a range from 10 wt. % to 60 wt. %.

6. The process of claim 2, wherein:
   the weight percentage of the solid polymer product, based on the total weight of the liquid oligomer product and the solid polymer product, is in a range from 10 wt. % to 60 wt. %;
   the liquid oligomer product comprises from 92 to 99.9 wt. % $C_6+C_8$ olefins; and
   the solid polymer product has a Mn in a range from 5,000 to 25,000 g/mol and a Mp in a range from 30,000 to 200,000 g/mol.

7. The process of claim 2, wherein at least a portion of the solid polymer product comprises chemically-treated solid oxide particles.

8. The process of claim 2, wherein the process further comprises a step of isolating the solid polymer product from the liquid oligomer product and/or from the organic reaction medium using one or more separation techniques.

9. The process of claim 8, wherein the one or more separation techniques comprises a filtration process, an evaporation process, a distillation process, or combinations thereof.

10. The process of claim 1, wherein the oligomer product is formed in an oligomerization reactor without reactor fouling.

11. The process of claim 1, wherein the catalyst system is produced by a process comprising:
    (i) contacting the chemically-treated solid oxide and the organoaluminum compound for a first period of time to form a precontacted mixture; and
    (ii) contacting the precontacted mixture with the heteroatomic ligand transition metal compound complex for a second period of time to form the catalyst system.

12. The process of claim 1, wherein the catalyst system is produced by a process comprising:
    (i) contacting the heteroatomic ligand transition metal compound complex and the organoaluminum compound for a first period of time to form a precontacted mixture; and
    (ii) contacting the precontacted mixture with the chemically-treated solid oxide for a second period of time to form the catalyst system.

13. A process comprising:
    (a) contacting, in any order, a heteroatomic ligand transition metal compound complex, an organoaluminum compound, and a chemically-treated solid oxide to form a catalyst system;
    (b) contacting ethylene, the catalyst system, and an organic reaction medium; and
    (c) forming an oligomer product comprising a liquid oligomer product and a solid polymer product; wherein:
    the weight percentage of the solid polymer product, based on the total weight of the liquid oligomer product and the solid polymer product, is in a range from 5 wt. % to 65 wt. %.

14. The process of claim 1, wherein the chemically-treated solid oxide comprises a solid oxide treated with an electron-withdrawing anion, and wherein:

the solid oxide comprises silica, alumina, silica-alumina, silica-coated alumina, or any combination thereof; and the electron-withdrawing anion comprises sulfate, fluoride, chloride, or any combination thereof.

15. The process of claim 1, wherein:

the heteroatomic ligand transition metal compound complex comprises a diphosphino amine chromium compound complex, an $N^2$-phosphinyl amidine chromium compound complex, an $N^2$-phosphinyl formamidine chromium compound complex, an $N^2$-phosphinyl guanidine chromium compound complex, or any combination thereof;

the chemically-treated solid oxide comprises fluorided alumina, sulfated alumina, fluorided silica-alumina, sulfated silica-alumina, fluorided silica-coated alumina, fluorided-chlorided silica-coated alumina, sulfated silica-coated alumina, or any combination thereof; and the organoaluminum compound comprises trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, or any combination thereof.

16. The process of claim 15, wherein:

the weight percentage of the solid polymer product, based on the total weight of the liquid oligomer product and the solid polymer product, is in a range from 15 wt. % to 55 wt. %;

the liquid oligomer product comprises from 92 to 99.9 wt. % $C_6+C_8$ olefins; and the solid polymer product has a Mn in a range from 5,000 to 25,000 g/mol and a Mp in a range from 30,000 to 200,000 g/mol, and at least a portion of the solid polymer product comprises chemically-treated solid oxide particles.

17. The process of claim 2, wherein the chemically-treated solid oxide comprises a fluorided solid oxide, a sulfated solid oxide, or a combination thereof.

18. The process of claim 17, wherein the catalyst system is substantially free of aluminoxane compounds.

19. The process of claim 2, wherein:

the heteroatomic ligand transition metal compound complex comprises a diphosphino amine chromium compound complex, an $N^2$-phosphinyl amidine chromium compound complex, an $N^2$-phosphinyl formamidine chromium compound complex, an $N^2$-phosphinyl guanidine chromium compound complex, or any combination thereof;

the chemically-treated solid oxide comprises fluorided alumina, sulfated alumina, fluorided silica-alumina, sulfated silica-alumina, fluorided silica-coated alumina, fluorided-chlorided silica-coated alumina, sulfated silica-coated alumina, or any combination thereof; and the organoaluminum compound comprises trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, or any combination thereof.

20. The process of claim 19, wherein:

the liquid oligomer product comprises from 92 to 99.9 wt. % $C_6+C_8$ olefins; and the solid polymer product has a Mn in a range from 5,000 to 25,000 g/mol and a Mp in a range from 30,000 to 200,000 g/mol, and at least a portion of the solid polymer product comprises chemically-treated solid oxide particles.

* * * * *

UNITED STATES PATENT AND TRADEMARK OFFICE
CERTIFICATE OF CORRECTION

PATENT NO. : 9,707,549 B1
APPLICATION NO. : 15/165267
DATED : July 18, 2017
INVENTOR(S) : Uriah J. Kilgore et al.

Page 1 of 1

It is certified that error appears in the above-identified patent and that said Letters Patent is hereby corrected as shown below:

Column 96, Line 7: "5. A The process of claim 2" should be changed to --5. The process of claim 2--

Signed and Sealed this
Seventeenth Day of April, 2018

Andrei Iancu
*Director of the United States Patent and Trademark Office*